United States Patent [19]

Liao et al.

[11] Patent Number: 5,605,929
[45] Date of Patent: Feb. 25, 1997

[54] METHODS AND COMPOSITIONS FOR INHIBITING 5α-REDUCTASE ACTIVITY

[75] Inventors: Shutsung Liao, Chicago, Ill.; Tehming Liang, Centerville, Ohio

[73] Assignee: Arch Development Corp., Chicago, Ill.

[21] Appl. No.: 442,055

[22] Filed: May 16, 1995

Related U.S. Application Data

[63] Continuation-in-part of Ser. No. 904,443, Jul. 1, 1992, Pat. No. 5,422,371, which is a continuation-in-part of Ser. No. 889,589, May 27, 1992, abandoned.

[51] Int. Cl.⁶ .......................... A61K 31/35; C07D 311/04
[52] U.S. Cl. .......................... 514/456; 514/544; 560/70; 549/406
[58] Field of Search .................... 514/456, 544; 560/70; 549/406

[56] References Cited

U.S. PATENT DOCUMENTS

| | | | |
|---|---|---|---|
| 4,191,759 | 3/1980 | Johnston et al. | 424/242 |
| 4,220,775 | 9/1980 | Rasmusson et al. | 221/18 |
| 4,268,517 | 5/1981 | Niebes et al. | 514/456 |
| 4,394,389 | 7/1983 | Van't Riet et al. | 514/544 |
| 4,840,966 | 6/1989 | Hara et al. | 514/456 |
| 5,032,514 | 7/1991 | Anderson et al. | |
| 5,126,129 | 6/1992 | Wiltrout et al. | 514/456 |
| 5,318,986 | 6/1994 | Hara et al. | 514/456 |

FOREIGN PATENT DOCUMENTS 0004949  12/1979  European Pat. Off. .

OTHER PUBLICATIONS

Hashimoto et al. Chem. Pharm. Bull. (Japan) 37(1), 77–85, 1989 (English).
Anderson and Liao, Nature 219:277, (1968).
Baba, et al., J. Neurochem. 42:192 (1984).
Beato, Cell 56:335 (1989).
Begin, Proc. Nutrition Soc. 49:261–267 (1990).
Bingham and Shaw, J. Endocr. 57:111 (1973).
Bjorneboe, et al., Brit. J. Dermatol. 118:77–83 (1988).
Blohm et al., Endocrinology 119:959 (1986).
Blohm et al., Biochem. Biophy. Res. Comun. 95:273 (1989).
Bradnt, et al., J. Steroid Biochem Mol. Biol. 37:575 (1990).
Bruchovsky and Wilson, J. Biol. Chem. 243:2012 (1968).
Brooks, et al., Proc. Soc. Esp. Biol. Med. 169:67 (1982).
Brooks, et al., Endocrinology 109:830 (1981).
Brooks, et al., The Prostate 3:35 (1982).
Carter and Coffrey, The Prostate 16:39–48 (1990).
Chang and Liao, J. Steroid Biochem. 27:123 (1987).
Cooke and Robaire, J. Biol. Chem. 260:7489 (1985).
Cusan, et al., J. Am. Acad. Dermatol. 23:462–469 (1990).
Dell and Severson, Biochem. J. 258:171 (1989).
Diani et al., J. Clin. Endocr. and Metabl. 74:345 (1992).
Dinadiao, May Clin. Proc. 66:1018–1028 (1991).
Downing, et al., J. Am. Acad. Dermo. 14:221–225 (1986).
Ehrmann and Rosenfield, J. Clin. Endocrinol. Metab. 71:1 (1990).
Evans, Science 240:889 (1989).
Fang and Liao, Mol. Pharmacol. 5:428 (1969).
Frost and Gomez, Adv. Biol. Skin. 12:403 (1972).
Gent and ho, Biochemistry 17:3023 (1978).
Gent, et al., J. Biophys. 33:211 (1981).
George, et al., Endocrinology 119:959 (1989).
Gershon and Parmegiani, J. Med. Chem. 10:186 (1967).
Gittes, New England J. Med. 324:236 (1991).
Gormley, et al., J. Clin. Endocrinol. Metab. 70:1136 (1990).
Gorski, et al., Ann. Rev. Physiol. 42:17 (1976).
Halquenset, et al., J. Steroid Biochem. 28:731 (1983).
Hall, New Phytol. 71:855 (1972).
Hamilton, Am. J. Anat. 71:451 (1942).
Hammerstein, et al., J. Steroid Biochem. 19:591 (1983).
Hebborn, et al., Arch Dermatol. 124:387–391 (1988).
Herold and Kinsella, Am. J. Clin. Nutr. 43:566 (1986).
Hiipakka, et al., Endocrine Dependent Tumors, ed. Voight & Knabbe 2:43–61 (1991).
Horrobin, et al., J. Am. Acad. Dermatol. J. Am. Acad. Dermatol. 20:1045–53 (1989).
Horszewicz, et al., Cancer Res. 43:1809 (1983).
Huggins and Hodges, Cancer Res. 1:293 (1940).
Ichihara and Tanaka, Biochem. Biophys. Res. Comm. 149:481 (1981).
Imperato–McGinley, Trend Genet. 2:134 (1986).
Imperato–McGinley et al., J. Clin. Endocr. Metab. 70:77 (1990).
Isaacs, J. Clin. Endocr. Metab. 56:139 (1983).
Jensen, et al., Proc. Nat'l Acad. Sci. (USA) 59:632 (1968).
Kaighn, et al., Invest. Urol. 17:16 (1979).
Karmali, et al., J. Nat'l Cancer Inst. 73:457 (1984).
Kato, J. Steroid Biochem. 34:219 (1989).
Khan, 35 al., Febs Letter 292:98 (1991).
Kwok, et al., J. Am. Chem. Soc. 109:3684 (1987).
Lands, Ann. Rev. Biochem. 34:313 (1965).
Liang, et al., Endocrinology 112:1460 (1983).
Liang, et al., Endocrinology 115:2311 (1984).
Liang and Heiss, J. Biol. Chem. 256:7998 (1981).
Liang, et al., J. Steroid Chem. 19:385 (1983).
Liang and Liao, Clin. Research 39:720A.
Liao and Fang, Vitamins and Hormones 27:17 (1974).
Liao, et al., Endocrinology 94:1205 (1974).
Liao, et al., J. Biol. Chem. 248:6154 (1973).
Liao, Int. Rev. Cytology 41:87 (1975).
Liao, et al., J. Steroid Biochem. 34:41–51 (1989).
Mock, et al., J. Pediatrics 106:762 (1985).
Moguilewsky and Bouton, J. Steroid Biochem. 31:699 (1988).
Mooradian et al., Endocrine Rev. 8:1 (1987).

(List continued on next page.)

*Primary Examiner*—Mukund J. Shah
*Assistant Examiner*—Pavanaram K. Sripada

[57] ABSTRACT

Disclosed are a novel class of antiandrogenic compounds including saturated and unsaturated fatty acids, catechin gallates, their derivatives, and synthetic analogs, their method of synthesis, and their use in treating disorders associated with androgenic activities. Also disclosed is the use of known compounds not previously known for their antiandrogenic activity in treating disorders related to androgenic activities and cancers.

8 Claims, 37 Drawing Sheets

OTHER PUBLICATIONS

Morello, et al., Invest. Derm. 66:319 (1976).
Morse, et al., Brit. J. Dermatol. (1989) 121:75–90.
Munnich, et al., Lancet 2:1080 (1980).
Nalboone, et al., Lipids 25:301 (1990).
Needleman, et al., Ann. Rev. Biochem. 55:69 (1986).
Newman, Proc. Nat'l Acad. Sci. 87:5543–5547 (1990).
O'Malley, Mol. Endocrinol. 4:363 (1990).
Pattison and Buchanan, Biochem. J. 92:100 (1964).
Phillipson, et al., Eng. J. Med. 312–1210 (1985).
Pochi, Ann. Rev. Med. 41:187 (1990).
Rasmusson, et al., J. Med. Chem. 29:2298 (1986).
Rittmaster, et al., J. Androl. 10:259 (1989).
Rittmaster, et al., J. Clin. Endocr. Metab. 65:188–193 (1987).
Rose and Connolly, The Prostate 18:243–254 (1991).
Sansone and Reisner, J. Invest. Dermatol. 56:366 (1971).
Schafer and Kragballe, Lipids 26:557–560 (1991).
Schweikert and Wilson, Clin. Endocrinol. Metab. 38:811 (1974).
Serafini and Lobo, Fert. Steril. 43:74 (1985).
Siiteri and Wilson, J. Clinical Invest. 49:1737 (1970).
Strauss and Yesalis, Ann. Rev. Med. 42:499 (1991).
Strong, et al., Brit. J. Clin. Prac. Nov/Dec:444–445 (1985).
Synder, Ann. Rev. MEd. 35:207 (1984).
Szepesi, et al., J. Nutr. 119:161 (1989).
Tesoriere et al., J. Neurochem. 51:704 (1988).
Tosaki and Hearse, Basic Res. Cardiol. 83:158 (1988).
Vallette, et al., J. Steroid Biochem. 263:3639 (1988).
Vermeulen et al., The Prostate 14:45 (1989).
Voigt, et al., J. Biol. Chem. 248:4248 (1973).
Wenderoth and George, Endocrinology, 113:569 (1983).
Wilson, Am. J. Med. 68:745 (1980).
Wright, Prostaglandins, Leukotrienes and Essential Fatty Acids 38:229 (1989).
Ziboh and Miller, Ann. Rev. Nutr. 10:433 (1990).
Ziboh, ARch Dermatol. 125:241–245 (1989).
Zuniga, et al., J. Nutr. 119:152 (1989).
Begin, et al., NJCI, 5:1053–1061 (1986).
Anderson, et al., Prostaglandins, Leukotrienes and Essential Fatty Acids, 40:137–141 (1990).
Liang, et al., J. Biol. Chem. 260:4890–4895 (1985).
International Search Report, PCT/US93/04090.
Andersson and Russell, "Structural and biochemical properties of cloned and expressed human and rat steroid 5α–reductases," *Proc. Natl. Acad. Sci. USA*, 87:3640–3644, May, 1990.
Andersson et al., "Deletion of steroid 5α–reductase 2 gene in male pseudohermaphroditism," *Nature*, 354:159–161, Nov. 1991.
Andersson et al., "Expression Cloning and Regulation of Steroid 5α–Reductase, an Enzyme Essential for Male Sexual Differentiation, " *J. Biol. Chem.*, 264(27):16249–16255, Sep. 1989.
Berman and Rusell, "Cell–type–specific expression of rat steroid 5α–reductase isozymes," *Proc. Natl. Acad. Sci. USA*, 90:9359–9363, Oct. 1993.
Faller et al., "Finasteride: A Slow–Binding 5α–Reductase Inhibitor," *Biochemistry*, 32:5705–5710, 1993.
Giovannucci, "Epidemiologic Characteristics of Prostate Cancer," *Cancer (Suppl.)*, 75(7):1766–1777, Apr. 1995.
Harris et al., "Identification and selective inhibition of an isozyme of steroid 5α–reductase in human scalp," *Proc. Natl. Acad. Sci. USA*, 89:10787–10791, Nov. 1992.
Hilpakka and Liao, "Androgen Receptors and Action," *Endocrinology*, 3rd ed., (DeGroot, L. I., ed.) W. B. Saunders Co., Philadelphia, 2336–2351, 1995.
Hirsch et al., "LY191704: A selective, nonsteroidal inhibitor of human steroid 5α–reductase type 1," *Proc. Natl. Acad. USA*, 90:5277–5281, 1993.
Honda et al., "Inhibition of Saccharide Digestive Enzymes by Tea Polyphenols," In: *Food Phytochemicals for Cancer Prevention II, ACS Symp.* Ser. 547:84–89, American Chemical Society, Washington, D.C., 1994.
Liang and Liao, "Inhibition of steroid 5α–reductase by specific aliphatic unsaturated fatty acids," *Biochem. J.*, 285:557–562, 1992.
Liang et al., "Species Differences in Prostatic Steroid 5α–Reductases of Rat, Dog and Human," *Endocrinology*, 117(2):571–579, 1985.
McConnell et al., "Finasteride, an Inhibitor of 5α–Reductase, Suppresses Prostatic Dihydrotestosterone in Men with Benign Prostatic Hyperplasia," *Journal of Clinical Endocrinology and Metabolism*, 74(3):505–508, 1992.
Moore and Pizza, "Observations on the inhibition of HIV–1 reverse transcriptase by catechins," *Biochem. J.*, 288:717–719, 1992.
Rittmaster, "Finasteride," *The New England Journal of Medicine*, 330(2):120–125, Jan. 1994.
Russell and Wilson, "Steroid 5α–Reductase: Two Genes/Two Enzymes," *Annu. Rev. Biochem.*, 63:25–61, 1994.
Wynder et al., "Nutrition and Prostate Cancer: A Proposal for Dietary Intervention," *Nutrition and Cancer*, 22(1):1–10, 1994.
Yang and Wang, "Tea and Cancer," *Journal of the National Cancer Institute*, 85(13):1038–1049, Jul. 1993.

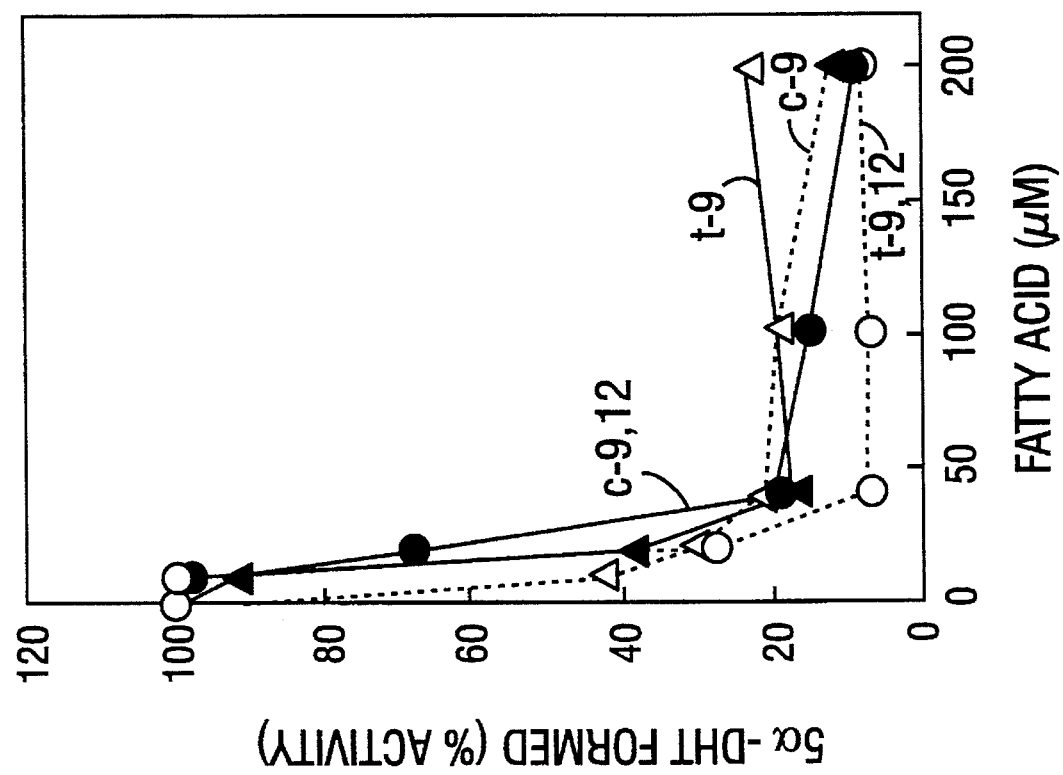
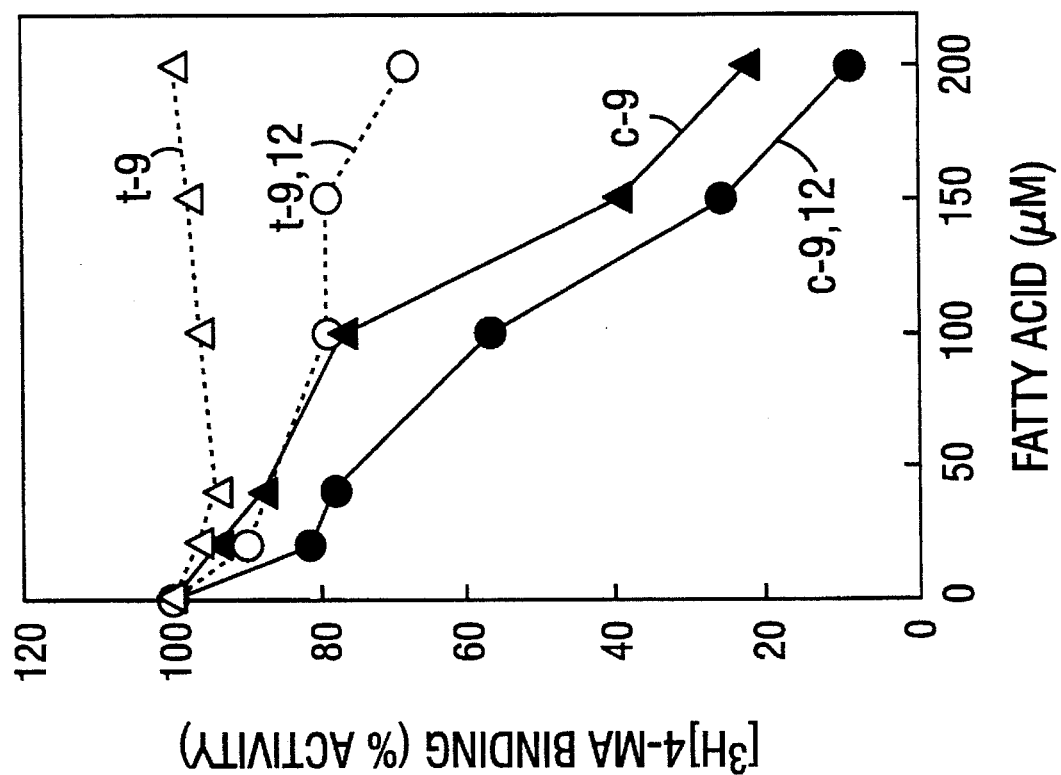
FIG. 13B
FIG. 13A $CH_3(CH_2)_nCH(F)COOH$ (n=0~17)

Gershon & Parmegliani,
J. Med.Chem.10:186(1967)

$F(CH_2)_nCOOH$ (n=1~19)

Pattison et
al. J. Org.Chem.21:883(1956)

$FCH_2(CH_2)_{7-n}CH=CH(CH_2)_{7+n}COOH$ (n=0~7)

Peters & Hall,
Biochem. Pharmacol.2:25(1959)

$F(CH_2)_nCH(R)(CH_2)_mCOOH$
(n=5~8; m=0~8; R=$CH_3$, $C_2H_5$, $C_3H_7$)

Pattison & Peters,
Biochem. J. 98:680(1966);
Pattison & Buchanan,
Biochem. J. 92:100(1964)

$CF_3(CH_2)_{14}CF_2CF_2COOH$

Stoll et al., J. Lipid
Res.32:843(1991)

$CH_3(CH_2)_{13-m}CF_2(CH_2)_{m-2}COOH$ (m=0~13)

Gent & Ho, Biochemistry
17:3023(1978)

FIG. 18

(+)catechin (-)catechin (+)epicatechin (-)epicatechin (+)gallocatechin (-)gallocatechin (+)epigallocatechin (-)epigallocatechin (+)epicatechingallate (−)epicatechingallate (+)gallocatechingallate (−)gallocatechingallate (+)epigallocatechingallate (−)epigallocatechingallate

METHODS AND COMPOSITIONS FOR INHIBITING 5α-REDUCTASE ACTIVITY

The U.S. government owns certain rights in the present invention pursuant to grant DK41670 from the National Institutes of Health.

The present invention is a continuation-in-part of U.S. Ser. No. 07/904,443, filed Jul. 1, 1992, now U.S. Pat. No. 5,422,371, which is a continuation-in-part application of U.S. Ser. No. 07/889,589 filed May 27, 1992, now abandoned; the entire text and figures of which disclosures are specifically incorporated herein by reference without disclaimer.

BACKGROUND OF THE INVENTION

1. Field of the Invention

The present invention relates generally to compounds, compositions and methods regulating the actions of androgens and other steroid hormones by modulating the activity of 5α-reductase. More particularly, the present invention relates to the use of these compounds to treat disorders that are caused by abnormal androgen action in cells or organs. This invention also deals with the use of natural and synthetic fatty acids and catechins, especially polyunsaturated fatty acids and their derivatives and epigallocatechin gallates, as 5α-reductase inhibitors and as therapeutic agents.

2. Description of the Related Art

Uses of androgens known to the medical arts include, for example, treatment of hypogonadism and anemia (Synder, 1984; Mooradian et al., 1987). The abuse of androgen among athletes to enhance performance is well known (Strauss and Yesalis, 1991). Androgens are also known to promote the development of benign prostatic hyperplasia (BPH) (Wilson, 1980), prostate cancer (Huggins and Hodges, 1940), baldness (Hamilton, 1942), acne (Pochi, 1990), hirsutism, and seborrhea (Hammerstein et al., 1983; Moguilewslcy and Bouton, 1988). Approximately 70% of males in the U.S. over the age of 50 have pathological evidence of BPH (Carter and Coffey, 1990). Prostate cancer is the second leading cause of cancer death in males in the U.S. (Silverberg and Lubera, 1990; Gittes, 1991). Male-patterned baldness can start as early as the teens in genetically susceptible males, and it has been estimated to be present in 30% of Caucasian males at age 30, 40% of Caucasian males at age 40, and 50% of Caucasian males at age 50. Acne is the most common skin disorder treated by physicians (Pochi, 1990) and affects at least 85% of teen-agers. In women, hirsutism is one of the hallmarks of excessive androgen action (Ehrmann and Rosenfield, 1990). The ovaries and the adrenals are the major sources of androgen in women.

1. Differential Actions of Testosterone and 5α-Dihydrotestosterone (5α-DHT)

In men, the major androgen circulating in the blood is testosterone. About 98% of the testosterone in blood is bound to serum proteins (high affinity binding to sex-steroid binding globulin and low affinity binding to albumin), with only 1–2% in free form (Liao and Fang, 1969). The albumin-bound testosterone, the binding of which is readily reversible, and the free form are considered to be bioavailable, and account for about 50% of total testosterone. Testosterone enters target cells apparently by diffusion. In the prostate, seminal vesicles, skin, and some other target organs it is converted by a NADPH-dependent 5α-reductase to a more active metabolite, 5α-DHT. 5α-DHT then binds to androgen receptor (AR) in target organs (Anderson and Liao, 1968; Bruchovsky and Wilson, 1968; Liao, 1975). The 5α-DHT-receptor complexes interact with specific portions of the genome to regulate gene activities (Liao et al., 1989). Testosterone appears to bind to the same AR, but it has a lower affinity than 5α-DHT. In tissues such as muscle and testes, where 5α-reductase activity is low, testosterone may be the more active androgen.

The difference between testosterone and 5α-DHT activity in different androgen-responsive tissues is further suggested by findings in patients with 5α-reductase deficiency. Males with 5α-reductase deficiency are born with female-like external genitalia. When they reach puberty, their plasma levels of testosterone are normal or slightly elevated. Their muscle growth accelerates, the penis enlarges, voice deepens, and libido toward females develops. However, their prostates remain non-palpable, they have reduced body hair, and they do not develop acne or baldness. Females with 5α-reductase deficiency do not have clinical symptoms (Imperato-McGinley, 1986).

The findings in 5α-reductase deficient patients suggest that inhibitors of 5α-reductase would be useful for the treatment of prostatic cancer, BPH, acne, baldness, and female hirsutism. Clinical observations and animal experiments have indicated that spermatogenesis, maintenance of libido, sexual behavior, and feed-back inhibition of gonadotropin secretion do not require the conversion of testosterone to 5α-DHT (Brooks et al., 1982; Blohm et al., 1986; George et al., 1989). This is in contrast to other hormonal therapies which abolish the actions of both testosterone and 5α-DHT.

Treatments of androgen-dependent skin and prostatic diseases by 5α-reductase inhibitors would be expected to produce fewer side effects than the presently available hormonal therapies. These include castration, estrogen therapy, high doses of superactive gonadotropin-releasing hormone such as Luprolide, and the use of competitive antiandrogens which inhibit AR binding of testosterone and 5α-DHT, such as flutamide, cyproterone acetate and spironolactone. The long term efficacy of 'competitive antiandrogens' is also compromised by their block of the androgenic feedback inhibition of gonadotropin secretion. This results in elevated gonadotropin secretion, which in turn increases testicular secretion of testosterone. The higher level of testosterone eventually overcomes the action of the antiandrogen.

2. Biological Importance of 5α-Reductase

Excessive 5α-DHT is implicated in certain androgen-dependent pathological conditions including BPH, acne, male-pattern baldness, and female idiopathic hirsutism. It has been shown that 5α-reductase activity and the 5α-DHT level are higher in the presence of BPH prostates than that of the patients with normal prostates (Isaacs, 1983; Siiteri and Wilson, 1970). 5α-reductase activity is reported to be higher in hair follicles from the scalp of balding men than that of nonbalding men (Schweikert and Wilson, 1974).

3. Steroidal 5α-Reductase Inhibitors

The most potent inhibitors of 5α-reductase developed so far are steroids or their derivatives. Among these the 4-aza-steroidal compounds (Merck Co.) are the most extensively studied (Liang et al., 1983; Rasmusson et al., 1986). These inhibitors are 3-oxo-4-aza-5α-steroids with a bulky functional group at the 17β-position, and act by reversibly competing with testosterone for the binding site on the enzyme.

The A-ring conformation of these compounds is thought to be similar to the presumed 3-enol transition state of the 5α-reduction of 3-oxo-Δ⁴-steroids. A prototype for 5α-reductase inhibitors is 17β-N,N-diethylcarbamoyl-4-methyl-4-aza-5α-androstan-3-one (4-MA), which behaves as an inhibitor of 5α-reductase in vivo, decreasing the prostatic concentration of 5α-DHT in intact male rats or in castrated male rats given testosterone propionate. 4-MA attenuated the growth of the prostate of castrated rats induced by testosterone, but had much less of an effect in rats given 5α-DHT (Brooks et al., 1981).

When dogs are treated with 4-MA, the prostate size decreases (Brooks et al., 1982; Wenderoth and George, 1983). Topical applications of 4-MA to the scalp of the stamptail macaque, a primate model of human male pattern baldness, also prevented the baldness which normally occurs at puberty in these monkeys (Rittmaster et al., 1987). These results also suggest that the growth of the prostate in rats and dogs, and baldness in the stamptail macaque depend on 5α-DHT. On the other hand, studies in rat pituitary cultures showed that complete inhibition of testosterone conversion to 5α-DHT by 4-MA did not affect testosterone inhibition of LH release, indicating direct action of testosterone in this system (Liang et al., 1984).

Another potent inhibitor is Proscar™ (Merck Co.) (Finasteride, MK-906, or 17β-N-t-butylcarbamoyl-4-aza-5α-androst-1-en-3-one). The inhibitor has no significant affinity for the rat prostate AR. In clinical trials, Proscar™ decreases the plasma level of 5α-DHT and the size of the prostate and also improves urinary flow in patients with benign prostatic hyperplasia (Vermeulen et at., 1989; Rittmaster et al., 1989; Gormley et al., 1990; Imperato-McGinley et al., 1990). In stamptail macaque monkeys, Proscar™ administered orally at 0.5 mg/day, alone or in combination with topical 2% Minoxidil™, reduced serum 5α-DHT level, and reversed the balding process by enhancing hair regrowth by topical Minoxidil™ (Diani et al., 1992). The effects of Minoxidil™ and Proscar™ were additive.

Among other steroidal compounds shown to inhibit 5α-reductase are 4-androstane-3-one-17β-carboxylic acid (Voigt et al., 1985), 4-diazo-21-hydroxymethyl-pregnane-3-one (Blohm et al., 1989), and 3-carboxy A-ring aryl steroids (Brandt et at., 1990).

4. Biological and Biochemical Effects of Fatty Acids and Lipids

Since treatments of androgen-dependent skin and prostatic diseases by 5α-reductase inhibitors can produce fewer side effects than the hormonal therapies which indiscriminately inhibit all androgen actions, it is desirable to provide different types of 5α-reductase inhibitors.

Several membrane-associated enzymes (e.g., 5'-nucleotidase, acetyl CoA carboxylase) have been shown to be affected by the polyunsaturated fatty acid content of dietary fat, and to alter the physicochemical properties of cellular membranes (Zuniga et al., 1989; Szepsesi et al., 1989). Various types of phospholipases in rat ventricular myocytes are modulated differentially by different unsaturated fatty acids in the culture media (Nalboone et al., 1990). In addition, treatment of cerebral cortical slices (Baba et al., 1984) or intact retina (Tesoriere et al., 1988) with unsaturated fatty acids can enhance adenyl cyclase activities.

Few studies have been directed to the elucidation of the mode of action of free fatty acids on enzymes in cell-free systems. Certain cis-unsaturated fatty acids, at 50 μM, were shown to stimulate protein kinase C activity (Dell and Severson, 1989; Khan et al., 1991) and to inhibit steroid binding to receptors for androgens, estrogens, glucocorticoids, and progestins (Vallette et al., 1988; Kato, 1989). It has not been shown that unsaturated fatty acids can affect steroid receptor binding of steroid hormones in vivo in an animal or human.

SUMMARY OF THE INVENTION

The present invention relates generally to the utilization of certain long chain fatty acids and catechins including derivatives of these classes of compounds for the control of androgen activity in target organs and cells through the modulation of 5α-reductase activity. In certain aspects, particular fatty acids and catechin compounds are employed to repress androgenic activity by inhibiting the formation and availability of active androgen in target cells. Consequently, the invention is useful for the treatment of a wide variety of conditions including, but not limited to, the treatment of prostatic hyperplasia, prostatic cancer, hirsutism, acne, male pattern baldness, seborrhea, and other diseases related to androgen hyperactivity. Several of these compounds have been shown to effectively decrease body weight and, in some cases, to decrease the weight of an androgen-dependent body organ, such as the prostate and other organs. The effectiveness of these compounds may be dependent also on their action on other mechanisms involved in angiogenesis, cell-cell interaction, and on their interaction with various components of organs or cells.

Compounds useful in the practice of the present invention include various isomers of saturated and unsaturated fatty acids, natural and synthetic analogues, and derivatives from which these fatty acids can be generated as well as the metabolite and oxidation products of these fatty acids. The use of these and other fatty acids and their derivatives is also contemplated. Also useful are catechin compounds, particularly, catechins that are structurally similar to epicatechin gallate (ECG) and epigallocatechin gallate (EGCG). EGCG has an additional hydroxyl group on the epicatechin gallate molecule which has been found to be surprisingly active in modulating several 5α-reductase mediated processes. EGCG derivatives having such an additional OH group on the ECG molecule were shown to be active in inducing body weight loss and particularly in reducing the size of androgen sensitive organs such as preputial glands, ventral prostate, dorsolateral prostate, coagulating glands, seminal vesicles, human prostate tumors, and breast tumors in nude mice.

The inventors have discovered the importance of certain structural features of some catechin compounds which appear to contribute to activity toward 5α-reductase. The presence of an additional hydroxyl group in gallocatechin gallate as compared with catechin gallate has a significant effect on activity as reflected in the ability to reduce body and organ weight and tumor growth in animals. The structural requirements for activity therefore are EGCG which has one extra —OH group on the ECG molecule was considerably more active than ECG in inducing body weight loss, and in reducing the sizes of preputial gland, ventral prostate, dorsolateral prostate, coagulating glands, seminal vesicles, and tumors of the prostate and breast.

The general formula for 5α-reductase inhibitors is as shown:

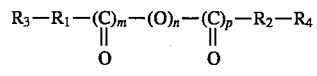

or

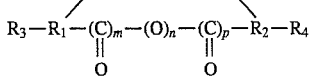

m, n, and p can be 0 or 1. $R_1$, $R_2$, and $R_5$, can have 0 to 6 atom chain consisting of C, N, S or O.

Each of the atoms in the chain can have a substitution of —H, —OH, —$CH_3$, —$OCH_3$, —$OC_2H_5$, —$CF_3$, —$CHF_2$, —SH, —$NH_2$, halogen, =O, —$CH(CH_3)_2$ or —$C(CH_3)_3$.

Atoms in $R_5$ is connected to atoms in $R_1$ and $R_2$. $R_3$ or $R_4$ can be: —H, —OH, —$CH_3$, —$OCH_3$, —$OC_2H_5$, —$CF_3$, —$CHF_2$, —SH, —$NH_2$, halogen, =O, —$CH(CH_3)_2$, or —$C(CH_3)_3$, or the following groups:

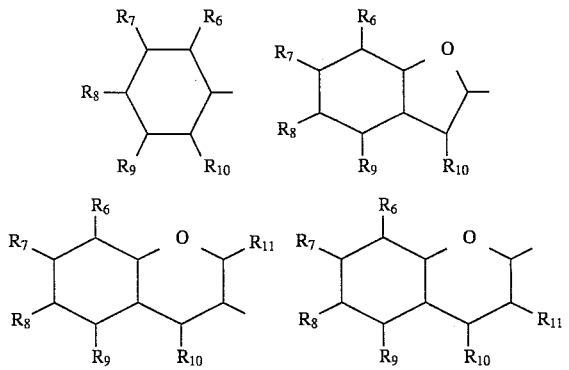

$R_6$ to $R_{10}$ can be: —H, —OH, —$CH_3$, —$OC_2H_5$, —$CF_3$, —$CHF_2$, —SH, —$NH_2$, halogen, =O, —$CH(CH_3)_2$, —$C(CH_3)_3$, galloyl, or gallolyl groups.

Carbon-carbon linkages in $R_1$ to $R_{11}$ may be saturated or have double bonds.

For example, the following compound has been found to be potent inhibitor of 5α-reductase:

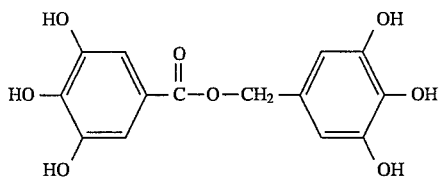

The active compounds may include ester linkages that may be hydrolyzed to the active unsaturated fatty acids, catechins, or the structure shown. In addition, R1 and R2 need not be individual substituents, but may represent together aromatic or heterocyclic moieties and containing halogen or alkyl substituents. Alternatively, R1/R2 may represent alicyclic moieties with one or more isolated double bonds. Combining all of the information obtained, the structures shown above comprise a group of novel 5α-reductase inhibitors.

For catechin gallates and their derivatives, the following general structure is noted:

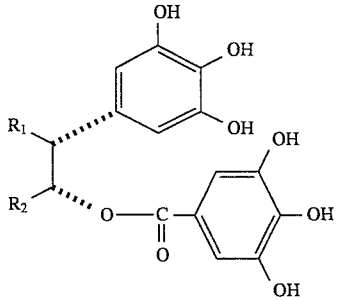

The fatty acid and catechin compounds are believed to effect the transformation of androgens by inhibition of 5α-reductase and, as a result, (a) limit the supply of dihydroxytesterone (5α-DHT) to target organs and suppress the 5α-DHT dependent androgen actions, and/or (b) prevent the metabolic loss of testosterone or other androgenic precursors of 5α-DHT and promote or maintain hormone actions that are dependent on testosterone or other 5α-DHT precursors. These compounds may act by controlling organogenesis, angiogenesis and/or cellular interaction with other chemical agents.

Steroids other than testosterone or dihydroxytestosterone are also substrates of 5α-reductase. It is expected, therefore, that the fatty acid and catechin compounds disclosed herein will also regulate the transformation and activation of other 3-oxodelta[4]-steroids and therefore control the biological functions of other steroid hormones through the same mechanism. An advantage to the use of fatty acid and catechin compounds of the present invention, and particularly some of their derivatives, is their relative stability in vivo and in vitro. In general, one may prepare derivatives that are not easily metabolized, degraded or incorporated into lipid structures or other derivatives. Stability may, for example, be increased by alkylation, cyclization, fluorination, etc. One will of course not wish to prepare derivatives that interfere with the functional aspects of the fatty acid or catechin. Certain of the fatty acid and catechin compounds are particularly effective in exhibiting organ specificity without significant side effects and in such cases one would choose to prepare derivatives that would not significantly increase side effects.

As discussed, there are certain structural features of the catechins that contribute to their utility and effectiveness in particular uses, such as inhibition of sebum production. This appears also to be true for the selection of fatty acids that are active inhibitors of 5α-reductase. As shown in Tables 1 and 2, a relatively large number of polyunsaturated fatty acids inhibit 5α-reductase activity. While the glycerides, esters, nitriles and chlorides showed little activity in the cell binding assays, some of these compounds are likely to be hydrolyzed outside the cells, or hydrolyzed after entering cells, to form the free fatty acid. In comparison with free fatty acids, it may be desirable to administer free fatty acids as glycerides or other derivatives that are relatively more stable to oxidation and/or are less readily metabolized than the free acids. Such derivatives are, of course, considered to be therapeutically active compounds.

In general, the inventors have observed that where fatty acid compounds are employed for inhibition of 5α-reductase activity, the length of the fatty acid carbon chain, as well as the position and number of double bonds in the molecules, appear to relate to activity. The highest activities are observed with 14 or more carbon atoms and at least one, preferable two or more, double bonds. The effectiveness of the unsaturated fatty acids is dependent on the positions of double bonds in the carbon chains.

In addition to certain fatty acids, it has been shown that gallates of catechins and gallocatechins are effective 5α-reductase inhibitors. This class of inhibitors includes a relatively large group of related compounds, some of which have been isolated and identified. These compounds are found in several types of plant bark and leaves, particularly tea and, most particularly, in green tea. Catechins with galloyl substitution showed surprising activity as inhibitors of 5α-reductase. These compounds include catechin gallate (CG), epicatechin gallate (ECG), epigallocatechin gallate (EGCG), the optical isomers, and conjugated substances such as theaflavins and theaflavin mono- (or di-) gallates. The latter compounds are components of fermented teas including black tea.

The inventors determined that active catechin gallates have three distinct groups in their molecules: (a) a 3-flavonol substituent; (b) a 3',4',5'-trihydroxybenzen (gallolyl) group attached to the 2-position of the flavonol; and (c) a gallic acid that forms an ester linkage (galloyl) with the 3-OH of the flavonol. The three groups may independently contribute to the inhibitory action, but the effect on 5α-reductase appears to be synergistic. Certain synthetic gallate derivatives (such as methyl gallate and n-propyl gallate, 3,4,5-trihydroxybenzamide, gallic acid and pyrogallol) were not as active as catechin gallate, indicating that the gallolyl or galloyl structure alone was not sufficient for high inhibitory activity. A low inhibitory activity was found within octyl gallate indicating that for the inhibitory activity, the flavonol group of catechin gallates may be replaced by other groups having similar geometric structures. Based on the lower activities of catechin or epicatechin compared with their gallate derivatives, it appears that the essential structural feature required for high 5α-reductase inhibition is an acyl (galloyl) or a trihydroxybenzen group that forms an ester or ether linkage with the flavonol.

By analogy with the fatty acid compounds, the inventors expect that certain active catechin gallates may not enter target cells easily. However, esterification of hydroxyl groups on the inhibitory compounds should enhance the ability of these compounds to enter the target cells. Once inside the cells, esters would be readily hydrolyzed by esterases to alcohols (e.g., epigallocatechin gallate) that can inhibit 5α-reductases (Williams, 1985).

In another aspect of the invention, γ-linolenic acid was found to be a particularly potent 5α-reductase inhibitor. The ability of γ-linolenic acid to inhibit 5α-reductase in solubilized microsomes indicates that the γ-linolenic acid inhibition may not be rigidly dependent on the native source of endoplasmic reticulum membranes. The fatty acid inhibitor may act by interacting with the reductase and/or other components that are vital for reductase activity. The inhibitory fatty acids may also interact with and potentiate other endogenous inhibitors or interfere with lipids which may potentiate the reductase. A proposed mechanism (Brandt et al., 1990) for the 5α-reductase (E) reaction includes the following steps:

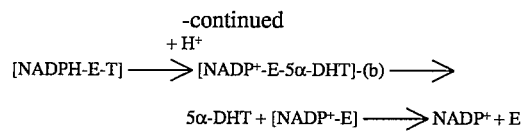

$$5\alpha\text{-DHT} + [\text{NADP}^+\text{-E}] \longrightarrow \text{NADP}^+ + E$$

It was surprising that two trans isomers of fatty acids, i.e., elaidic acid and linolelaidic acid, had little inhibitory activity in the [³H]4-MA binding assay, yet were as potent as their cis-isomers, oleic and linoleic acid, in the enzymatic assay. The cis-unsaturated fatty acids may inhibit the formation of [NADPH-E-T] (step a); whereas the trans isomers act at points after the formation of the ternary complex (step b).

In certain embodiments the disclosed methods are useful for reducing weight in an androgen dependent organ. The inventors have demonstrated that certain fatty acids and catechins are effective in reducing the weight of androgen dependent organs, including the preputial gland, ventral prostate, dorsolateral prostate, seminal vesicles, coagulating gland, and at high doses, also the testes. This effect was observed with several fatty acids. The most effective correlated with those that showed the most inhibitory activity toward 5α-reductase. In a preferred embodiment, γ-linolenic acid was shown to be particularly effective in reducing the weight of androgen dependent organs; in particular, the ventral, prostate and preputial organ. It is evident that a relatively broad range of long chain polyunsaturated fatty acids will have the desired effect in reducing the weight of androgen dependent organs. One will select such fatty acids based on, for example, in vivo stability, ease of administration, and release in active form. Certain ester or ether derivatives are expected to be hydrolyzed by cell esterases to an active form; for example, glycerides. A particularly preferred long chain polyunsaturated fatty acid is γ-linolenic acid. This fatty acid, as well as related derivatives and compounds, are particularly effective. Contemplated derivatives are esters, particularly hydrolyzable esters.

The invention also includes the inhibition of 5α-reductase in cells by contacting the cells with a composition comprising at least one catechin compound. Several catechins including (−)epicatechin gallate (ECG) and (−)epigallocatechin gallate (EGCG) reduced the weight of the androgen dependent organs, ventral prostate and preputial organ; however, EGCG also reduced body weight by as much as 35% in some case, suggesting a potential use of this compound and related species as weight loss agents. EGCG would be ideal for weight loss programs because of its lack of toxicity or apparent side effects. EGCG and related catechins occur naturally in several types of plants, including tea, and thus have a long history of safety as a component of a food item.

EGCG, EGC and γ-linolenic acid are particular examples of catechins and fatty acids that reduce weight of androgen-sensitive organs. The inventors believe that these compounds reduce lipid or sebum production in male hormone sensitive organs, for example, in ventral and dorsal lateral prostate glands, coagulating glands, and seminal vesicles. EGCG and ECG are structurally similar in that EGCG has eight hydroxyl groups compared with the seven hydroxyl groups in EGC, yet EGCGC is significantly more effective than ECG in promoting weight reduction. The effect of EGCG on lipid production or organ weights may be dependent on a specific EGCG interaction with a macromolecule that is specific for EGCG on the modulation of cell-cell or protein-protein interactions, or regulation of enzyme activity or gene expression. Regulation or modulation of the interaction or the function of the EGCG receptor or protein complex by natural or synthetic compounds would be expected to offer a means to control the lipid synthesis or the growth and function of androgen-sensitive organs.

In more particular aspects of the invention, the inventors have discovered that certain catechins, particularly EGCG, can be administered to promote body weight loss that differentially affects overall body weight and prostate weight loss. In particular examples, it was shown that for a certain percentage of overall body weight loss, prostate weight loss was percentage-wise more than three times as much. The loss in body weight and the organ weight are likely due to EGCG interference of a common step in the pathway controlling body and organ weight gain. EGCG and related compounds may interact and interfere with a receptor macromolecule (probably containing a protein) that modulates specific lipid synthesis or accumulation. Lipids can modulate gene expression, cell development and differentiation, and organ growth. Specific interference of lipid metabolism in the cells and organs may control the growth of the organs, in particular, prostate sebaceus organs, preputial organs and other secretory organs. In certain applications, it is expected that benign or abnormal growth or cancer of these organs may be treated or even prevented by administration of catechin related compounds.

It has been demonstrated that catechin compounds will arrest or reduce human prostate and breast cancer cell growth. The effectiveness of catechin compounds was shown by the inventors to be dependent on the methods these compounds were administered to the experimental animals. The inventors found that intraperitoneal application was much more effective than oral route. It is expected that direct application to the prostate having tumor will be very effective. The inventors demonstrated that EGCG was surprisingly effective in suppressing and even reducing the size of human prostate and breast tumors in animal models. The effect was illustrated with EGCG; however, structurally similar catechin compounds should also be effective, particularly those that are structurally similar to EGCG in having at least one additional hydroxyl group as compared with EGC. Thus, the EGCG species that contains eight hydroxyl groups is significantly more effective in reducing body weight than is EGC, which contains seven hydroxyl groups. Compounds of this general structure are expected to be particularly effective in chemoprevention and chemotherapy of human prostate cancer. Compounds having a part of structure similar to a part of structure of EGCG are also expected to be effective also.

A useful animal model for skin is the rat model. In rat sebaceous glands, as in human, sebum lipids are synthesized in the intermediate cells by the smooth endoplasmic reticulum (SER). The volume density of SER, as seen under electron microscopic examination, depends on androgen (Moguilewsky and Bouton, 1988). Since repression of androgen action can cause reduction of this density, the effectiveness of test compounds, systemically or topically administered to rats, can be evaluated by measuring their ability to reduce the volume density of SER.

Polyunsaturated fatty acids can be used as antiandrogenic agents through topical or systemic application. A preparation for this purpose can include a carrier, a protectant, an antioxidant (such as vitamin C or E and various catechins and polyphenols), and other pharmaceutical and pharmacological agents. It is also expected that such fatty acids can be used in a delivery system involving molecular recognition through which the said fatty acids are delivered to target sites. Such a delivery system may involve, among other methods, liposome techniques or immunological devices.

Natural or synthetic chemicals that can modulate the production or cellular action of receptors and macromolecules may be useful in the treatment of abnormalities such as obesity, BPH, prostate cancer, skin diseases, baldness, breast tumors, and hirsutism, which are related to lipid synthesis, body weight, and/or androgen function.

The inventors contemplate that animal models may be used to demonstrate the effectiveness of EGCG and related compounds on a variety of cancers. For example, Shionogi tumor and other tumor induced tumors may be studied in male rats. Human breast and prostate cancer cell growth may be studied in nude mice. Alternatively, rodent breast tumors induced by carcinogens and other cancers induced in transgenic mice or Dunning tumors in rats may be similarly analyzed for their chemotherapy by EGCG and related compounds.

Other aspects of the invention include methods for screening inhibitors of sebum production. While other animal models may be used, the inventors have found it convenient to use humans for screening. The method basically involves applying a compound suspected of inhibiting sebum production to some portion of the human body on the skin area that has sebaceus glands. These areas include the human forehead, as well as other areas of faces and hands. Ideally, the applications will cover two bilaterally similar areas, with one area designated a control area and the other a test area. One will then measure sebum production in each of these areas. Several ways of measuring sebum production may be employed; however, a convenient means is to use a clear tape over each area for a specified length of time. This length of time is conveniently 30–40 minutes, but could be shorter or longer; e.g. 10 minutes or 2–3 or more hours. Longer periods of time, however, will result in generally more sebum production and would be employed only in cases where sebum production is low or difficult to obtain. The use of a clear tape is particularly convenient because each tape may then be removed from the subject and the amount of sebum deposited on the tape measured or determined by such means as light scattering, decrease in light transmission, etc.

The inventors have found that regardless of the measurement means employed, it is rapid and convenient to assign a relative and arbitrary value for sebum production to each measurement. Use of arbitrary values avoids the necessity of absolute measurements and outside control samples because the control area tape may be used as a relative control. It has been found that when the ratio of the value for the test area to that of control is lower than the ratio before the application of the test compound to the control area, the test compound is a suitable candidate for use in sebum suppression. When identified by this method of screening, compounds that exhibit a lower ratio will be useful as topical agents.

The use of the fatty acid and catechin compounds disclosed in the present invention, in therapeutically effective amounts of pharmaceutical compositions containing one or more of the compounds of the invention, in some cases in combination with other therapeutic agents and carriers, or in natural or synthetic products, is appropriate in the treatment of various disorders. These disorders include, but not necessarily limited to, those conditions wherein excessive androgenic activities have been implicated, for example, male pattern baldness, female hirsutism, acne, BPH, and cancers of prostate, breast, skin and other organs.

These pharmaceutical compositions, comprising certain fatty acids, catechins or compounds of the invention, can be administered by topical or internal routes, including oral, injection, or other means, such as topical creams, lotions, hair tonics, scalp care products, or transdermic patch applications, alone or in combination with other compounds of the invention and or with other drugs, drug additives, or pharmaceutical compounds. Combination of unsaturated fatty acids and catechins will be beneficial for clinical or cosmetic treatments because they individually may selectively control the activities of different enzymes or isozymes, and they may act to stabilize each other or protect active compound from degradation or alteration by chemical, biological or environmental condition during the preparation, application or storage of the compounds or products. It has been demonstrated that some of these compounds appear to regulate steroid metabolism, and may thereby affect the function of normal or mutated hormone receptors. Therefore, these compositions are useful in the treatment of androgen and other hormone-sensitive or insensitive disorders or tumors. The compounds of the invention are also important in the studies of the mechanism of action of hormones and anti-hormones.

As used herein the terms "contact", "contacted", and "contacting", are used to describe the process by which an effective amount of a pharmacological agent, e.g., an inhibitor of 5α-reductase, comes in direct juxtaposition with the target cell. As used herein the term "cell" refers to cells capable of fatty acid synthesis. What is meant by an effective amount is the amount of drug necessary to give the therapeutically desired level of 5α-reductase inhibition.

Although the present invention has been described primarily in terms of its clinical usefulness, as indicated by the art accepted model of inhibition of sebum production used in the practice of the present invention, the methods and compositions herein will also be useful in methods for screening a candidate substance for 5α-reductase stimulatory properties in combination with compositions of the present invention. Such a method would comprise preparation of different isozyme of 5α reductase including isozymes genetically engineered and expressed in cells; obtaining a candidate substance; contacting a culture of sebaceous cells with said candidate substance; simultaneously contacting said culture with a composition of the present invention having 5α-reductase inhibitory activity; and determining the extent of 5α-reductase inhibition. 5α-reductase inhibition using compositions of the present invention may also be utilized in such methods to provide a baseline control for determining the efficacy of a candidate substance, as well as to test such a candidate substance for synergistically enhancing the 5α-reductase inhibitory activity of the compositions disclosed herein. As used herein, a "candidate substance" is defined as any substance or compound, either naturally occurring or synthetic that is suspected to affect 5α-reductase activity.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 13A. Effects of oleic acid (C18:1, cis-9) (c-9), linoleic acid (C18:2, cis-9,12) (c-9,12), elaidic acid (C18:1, trans-9) (t-9), and linolelaidic acid (C18:2, trans-9,12) (t-9, 12) on rat liver microsomal 5α-reductase activity as determined by [$^3$H]4-MA binding assay. The abbreviations in parentheses indicate: the number of carbon atoms in the carbon chain, the number and the position of cis or trans double bonds and abbreviation shown in the figures. The amount of rat liver microsomes was 10 μg protein. In the absence of lipid, the control value for the [$^3$H]4-MA binding assay was 30618±975 dpm. This value was taken as 100% activity.

FIG. 13B. Effects of oleic acid (C18:1, cis-9) (c-9), linoleic acid (C18:2, cis-9,12) (c-9,12), elaidic acid (C18:1, trans-9) (t-9), and linolelaidic acid (C18:2, trans-9,12) (t-9, 12) on rat liver microsomal 5α-reductase activity as determined by enzymatic assay. The abbreviations in parentheses are defined in FIG. 13A. The amount of rat liver microsomes was 2 μg protein. In the absence of lipid, the control value was 9.0±0.9 nmol 5α-DHT formed/15 min using 0.5 μM testosterone as substrate. This value was taken as 100% activity.

FIG. 18. Fatty acids which can be used to regulate 5α-reductase activity.

DETAILED DESCRIPTION OF THE PREFERRED EMBODIMENTS

A. Steroid Hormones and 5α-Reductase Activity

1. Androgens

Figure 1:
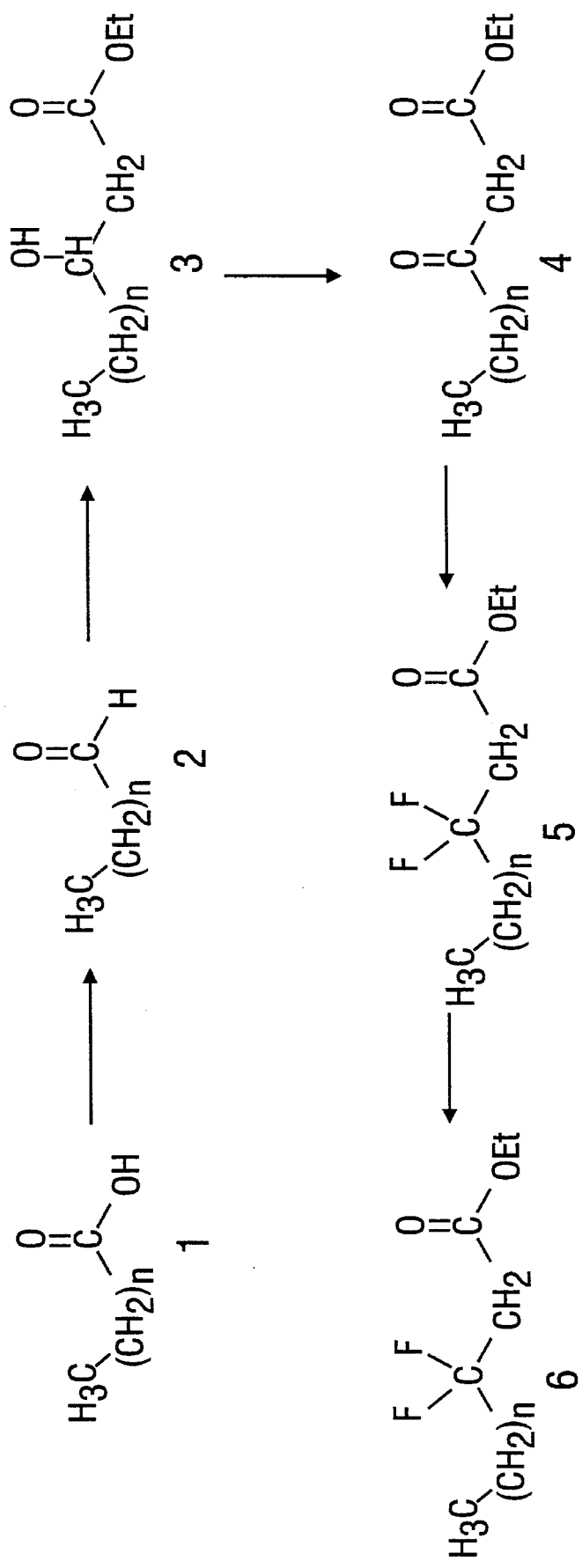
FIG. 1. Schematic representation of the synthesis of compounds 2 to 6 of Example 1.

Androgens are one of the six major classes of steroid hormones. Steroid hormones form complexes with specific receptor proteins in selective cells of target organs (Jensen et at., 1968; Liao, 1975; Gorski, et al., 1976). Steroid receptors are members of a superfamily of transcription factors that can regulate gene expression, and this function is dependent on the binding of a specific hormonal ligand to an appropriate receptor (Evans, 1989; Beato, 1989; O'Malley, 1990).

Studies of the specificity and affinity of steroid hormones for their receptors have contributed greatly to the understanding of the relationships among steroid and receptor structures and biological activity, target organ specificity, and the mechanism of action of many antihormones, including "competitive antiandrogens". "Competitive antiandrogens" are defined herein as those antiandrogens that interact with receptors and competitively prevent receptor binding of active androgens (Fang and Liao, 1969; Liao et al., 1973; Liao et al., 1974; Chang and Liao, 1987; Liao et al. 1989), although it should be noted that some compounds with an antiandrogenic activity may act by a different mechanism.

Androgens, produced in the testis, stimulate the differentiation of the male reproductive organs, including the penis, scrotum, prostate, seminal vesicles, epididymis, and vas deferens. With the onset of puberty, an increase in the production of androgen promotes the growth of these tissues. Androgen is required for spermatogenesis and accelerates skeletal muscular growth and bone formation. In the central nervous system, it stimulates libido and produces feedback inhibition of gonadotropin secretion. In skin, androgen increases the size of sebaceous glands and apocrine glands and converts villus hairs in the axillae, pubic region, and the beard to form coarser and longer terminal hairs. Androgen causes thickened vocal cords and lowers the pitch of the voice. Androgen also stimulates hematopoiesis.

Androgen action in many organs, such as prostate is dependent on the conversion of testosterone by a NADPH-dependent 5α-reductase to 5α-dihydrotestosterone (5α-DHT), which then binds to AR to exert its biological function (Liao et al., 1989). The inhibition of 5α-reductase limits the availability of 5α-DHT but not testosterone, therefore, 5α-reductase inhibitors are useful in selective treatment of 5α-DHT-dependent abnormalities, such as benign prostate hyperplasia, prostate cancer, hirsutism, male pattern alopecia and acne, without affecting testosterone-dependent testicular function, sexual behavior, and muscle growth (Russell and Wilson, 1994; Hipakka and Liao, 1995). Most 5α-reductase inhibitors are steroids or compounds with steroid-like structures. The present invention, however, also has identified specific fatty acids and catechins, including γ-linolenic acid and epigallocatechin-3-gallate, which are potent 5α-reductase inhibitors.

It is known that polyunsaturated fatty acids can correct the effects of fatty acid deficiencies that manifest as dermatitis, kidney necrosis, infertility, and cardiovascular diseases (Herold and Kinsella, 1986; Phillipson et al., 1985; Ziboh and Miller, 1990) and also can exhibit anti-tumor activities (Begin, 1990; Karmali et al., 1984). Many unsaturated fatty acids are essential components of mammalian membranes, typically in the acylated form of triglycerides and phospholipids (Lands, 1965).

Arachidonic acid serves as a specific precursor in the biosynthesis of prostaglandins and leukotrienes (Needleman et al., 1986). These metabolites of unsaturated fatty acids are mediators of inflammation. Unsaturated essential fatty acids have been implicated as dietary factors that influence acne. However, no firm support for this view has developed, and no successful treatment based on this idea has appeared (Downing et al., 1986). Synthetic retinoids and AR binding competitive antiandrogens have been used to obtain therapeutic improvement of acne in some individuals. These anti-acne agents increase the proportion of linoleic acid in sebum in parallel with clinical improvement (Wright, 1989).

2. 5α-reductase

Selective inhibitors of the different types of 5α-reductase, therefore, are desirable for studies of androgen action and for therapy for androgen-dependent tumors and other abnormalities.

Two 5α-reductase isozymes have been demonstrated in rats and humans. In the human, type 1 and 2 isozymes have only 50% amino acid sequence homology (Anderson et al., 1991). Type 1 isozyme has a neutral to basic pH optimum and is rather insensitive to the 5α-reductase inhibitor finasteride. Type 2 isozyme has an acidic pH optimum and is 30 times more sensitive to finasteride inhibition than type 1 isozyme. In the prostate, type 2 isozyme is the major form (Anderson et al., 1991), whereas, in the scalp, type 1 isozyme predominates (Harris et al., 1992). In the rat, it has been shown that the liver contains mainly type 1 isozyme (Berman and Russell, 1993); however, the prostate contains both type 1 (60%) and type 2 (40%) isozymes (Normington and Russell, 1992). γ-LA was found to inhibit 5α-reductase activity in both the liver and prostate (Liang and Liao, 1992). γ-LA therefore, is an inhibitor of both type 1 and type 2 isozymes. 5α-reductase isozymes in the hamster flank organ have not been characterized at the molecular level. However, 5α-reductase activity in hamster flank has an optimum of pH 8 (Takayasu and Adachi, 1972), indicating that the major 5α-reductase isozyme in the flank organ may be type 1, rather than the type 2 isozyme.

In a given individual, 5α-reductase activity is found to be higher in balding skin than from hairy skin (Bingham and Shaw, 1973). Some idiopathic hirsute women have a normal circulating level of testosterone, but their affected skin has a higher 5α-reductase activity than that of nonhirsute women (Serafini and Lobo, 1985). An increased 5α-reductase activity has also been reported for skin with acne (Sansone and Reisner, 1971).

Genetic evidence also supports the suggestion that 5α-DHT plays an important role in the development of BPH and the above skin conditions. In males with hereditary 5α-reductase deficiency, their prostates remain small or nonpalpable after puberty. They do not develop acne, temporal hairline recession, or baldness. Compared to their fathers and brothers, they have scanty beards and reduced body hair.

B. FATTY ACID METABOLISM

Fatty acids fluorinated at α, β, and ω positions (Gershan and Parmegiani, 1967; Pattison and Buchanan, 1964; Gent and Ho, 1978) and ω-oleic acids (Tosaki and Hearse, 1988) have been identified in plants and microorganisms, and have been chemically synthesized. Many of these fluorinated acids are toxic. Degradation of some fluorinated fatty acids can yield fluoro-acetic acid, which can be incorporated into fluorocitrate and can then block aconitase action. This can cause inhibition of the citric acid cycle and cellular energy production (Hall, 1972). Fluorinated fatty acids are often useful in the studies of fatty acid degradation, metabolism and transport in biological systems (Stoll et al., 1991), and biophysical studies of protein-lipid interaction and membranes functions (Gent et al., 1981).

Biotin is a cofactor of major carboxylases which are necessary for orderly production and metabolism of fatty acids. Alopecia caused by biotin-deficiency can be completely treated by biotin administration to patients. Oral administration and cutaneous application of unsaturated fatty acids can also improve biotin-dependent dermatological conditions including scalp hair growth (Munnich et al., 1980; Mock et al., 1985). The fatty acid effect is apparently due to supplementation of the deficient fatty acids and not related to regulation of androgen action involved in male pattern-alopecia.

C. PHARMACEUTICAL COMPOSITIONS

Aqueous compositions of the present invention comprise an effective amount of the 5α-reductase inhibitory agent dissolved or dispersed in a pharmaceutically acceptable aqueous medium. The phrase "pharmaceutically acceptable" refers to molecular entities and compositions that do not produce an allergic or similar untoward reaction when administered to a human.

The preparation of an aqueous composition that contains such an inhibitory compound as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The pharmaceutical compositions disclosed herein may be orally administered, for example, with an inert diluent or with an assimilable edible carrier, or they may be enclosed in hard or soft shell gelatin capsule, or they may be compressed into tablets, or they may be formulated for control release, such as transdermic and osmotic pressure devices, injectable devices and implantable devices, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. The percentage of the compositions and preparations may, of course, be varied and may conveniently be 100% (application of pure compounds). The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the composition may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

In other embodiments, one may desire a topical application of compositions disclosed herein. Such compositions may be formulated in creams, lotions, solutions, or in solid form depending upon the particular application. The formulation of pharmaceutically acceptable vehicles for topical administration is well known of skill in the art (see i.e., "Remington's Pharmaceuticals Sciences" 15th edition). Variation of the dosage of the compositions disclosed herein, will necessarily depend upon the particular subject, and the nature of the condition(s) being treated.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

D. ASSAYS FOR CANDIDATE SUBSTANCES

In still further embodiments, the present invention concerns a method for identifying new agents that act to inhibit the activity of 5α-reductase. Those new agents may be termed as "candidate substances." Different types of 5α-reductase isozymes have been found to be present in different combinations in different cells of various organs (Russel and Wilson, 1994). Therefore, it is desirable to have isozyme-selective inhibitors for therapeutic purposes. For the sources of type 1 and type 2 5α-reductase Rat 1A cells were genetically engineered to certain only type 1 or type 2 isozyme. Rat 1A cells or microsomes were used for the screening of isozyme-selective inhibitors. It is contemplated that this screening technique will prove useful in the general identification of any compound that will serve the purpose of inhibiting the activity of 5α-reductase or specific types of 5α-reductase. It is further contemplated that useful compounds in this regard will in no way be limited to the specific compositions disclosed herein, but any analogs, derivatives, synthetic modifications, or substitutions of constituents of those compositions which can effectively inhibit this activity either in vitro or in vivo.

Accordingly, in screening assays to identify pharmaceutical agents which inhibit 5α-reductase activity, it is proposed that compounds isolated from natural sources such as plants, animals or even sources such as marine, forest or soil samples, may be assayed for the presence of potentially useful pharmaceutical agents. It will be understood that the pharmaceutical agents to be screened could also be derived from chemical compositions or man-made compounds.

The active compounds may include fragments or parts of naturally-occurring compounds or may be only found as active combinations of known compounds which are otherwise inactive.

E. METHODS OF INHIBITING 5α-REDUCTASE ACTIVITY

In still further embodiments, the present invention is concerned with a method of inhibiting 5α-reductase which includes subjecting a cell to an effective concentration of a 5α-reductase inhibitor such as one of the family of fatty acid or ECGC compounds disclosed herein, or with a candidate substance identified in accordance with the candidate screening assay embodiments. This is, of course, an important aspect of the invention in that it is believed that by inhibiting the activity of 5α-reductase, one will be enabled to treat various aspects of disease and cancers, such as prostate-related cancers and diseases caused by abnormal androgen actions. It is believed that the use of such inhibitors to block abnormal androgen action will serve to treat cancers and diseases and may be useful by themselves or in conjunction with other anti-cancer therapies, including chemotherapy, resection, radiation therapy, and the like. The compounds of this invention, besides acting as 5α-reductase inhibitor, may have other effects that can lead to antitumor activity or to suppress abnormal growth of prostate or other organs.

The following examples illustrate the rationale and practice of the invention. Although many of the examples are based on the actions of androgens and ARs, they may also apply to the function of other steroid hormones which is dependent on or regulated by 5α-reductase or their isozymes. They are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of Fatty Acid Analogs and Related Molecules

1. Synthesis of β-Fluoro Fatty Acids

The synthesis of β-fluoro acid analogs of linolenic acid is a relatively straightforward process. Starting with the appropriate 16-carbon acid 1 (FIG. 1), aldehyde 2 can be obtained through reduction using isopentyl boron hydride β-Hydroxy acetate 3 can be made from 2 using zinc and ethyl bromoacetate in a Reformatski-type reaction. The β-keto ester 4 can be made from 3 using pyridinium dichromate in dichloromethane at room temperature. The difluoro ester 5 can be made from 4 using diethylaminosulfur trifluoride (DAST) in methylene chloride at room temperature. DAST is a fluorination reagent which is very selective for aldehydes, ketones and alcohols at room temperature. The free acid 6 is obtained via base hydrolysis of the ester group.

Figure 2:
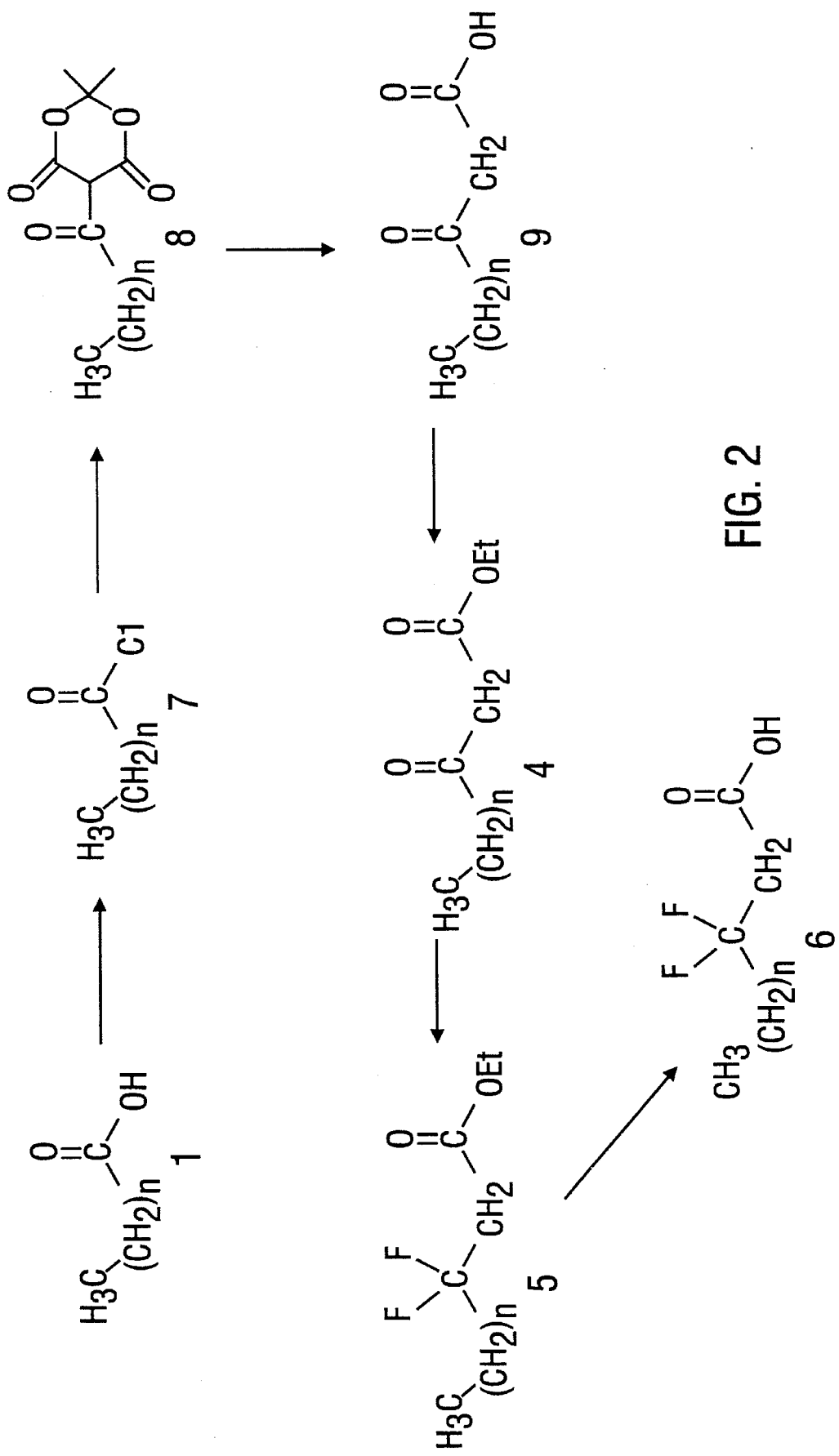
FIG. 2. Schematic representation of the synthesis of compounds 4 to 9 of Example 1.

Alternatively, one could produce the acid chloride 7 from 1 by reaction with thionyl chloride (FIG. 2). Compound 8 can be made by reaction of 7 with Meldrum's acid, which is the product from the reaction of malonic acid with acetone. Compound 8 undergoes ring opening and decarboxylation to form β-keto acid 9. From the β-keto acid 9 the sequence continues to produce compounds 4, 5, and the target compound 6 as previously described above.

2. Synthesis of 6-Membered Ring Linolenic Acid Mimetics

Figure 3:
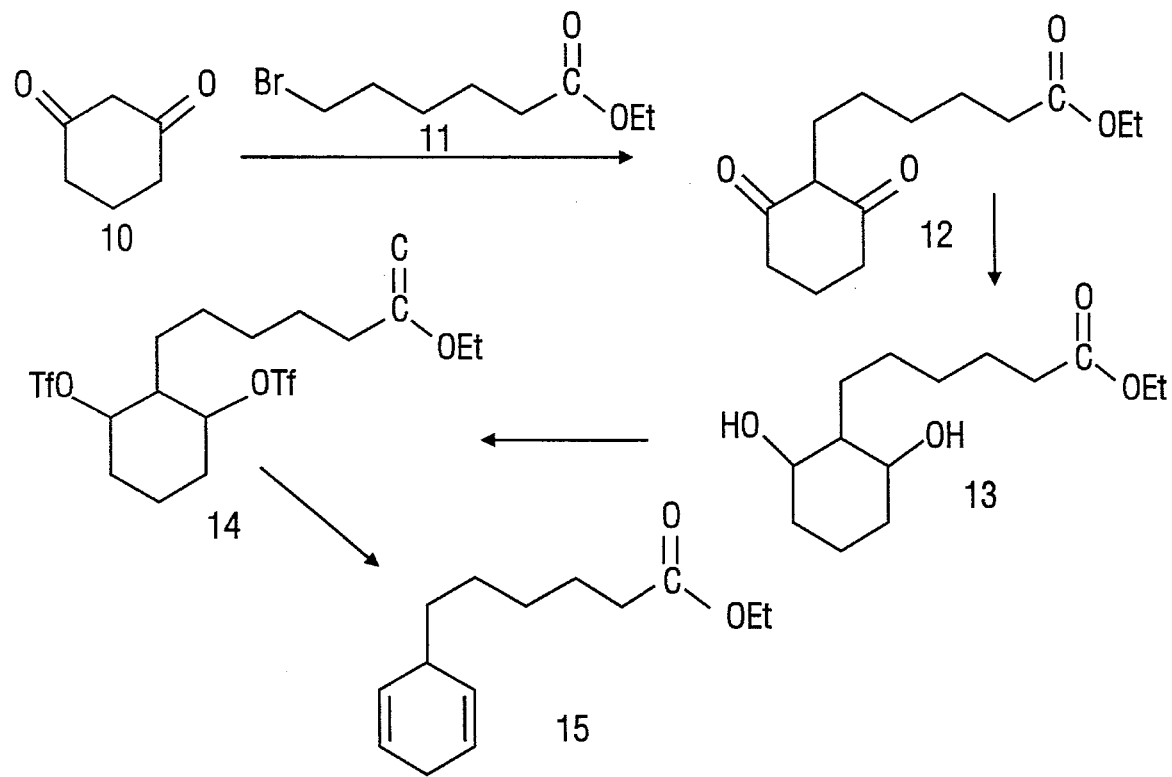
FIG. 3. Schematic representation of the synthesis of compounds 12 to 15 of Example 1.

Since the two key groups present in linolenic acid are 1) three cis double bonds and 2) the carboxylic acid group, a molecule can be designed that possess the same key groups and retains the activity of linolenic acid. Examples of such compounds are 15 and 21, the synthetic routes to which are shown in FIG. 3 and FIG. 4.

Starting from 1,3-hexanedione 10 one can produce compound 12 by forming the enolate anion of 10 followed by reaction with ethyl 6-bromocaproate 11. Reduction using sodium borohydride then gives compound 13. Reaction of 13 with trifluoromethylsulfonic anhydride gives the ditrifluoromethylsufonate (ditriflate) 14. Compound 14 can be trans/brined into the target linolenic acid mimic 15 by double elimination of triflate using 1,5-diazabicyclo[5.4.0]undec-5-ene (DBU). The free acid can be obtained or it can be formed in vivo by enzymatic hydrolysis of the ester group.

Figure 4:
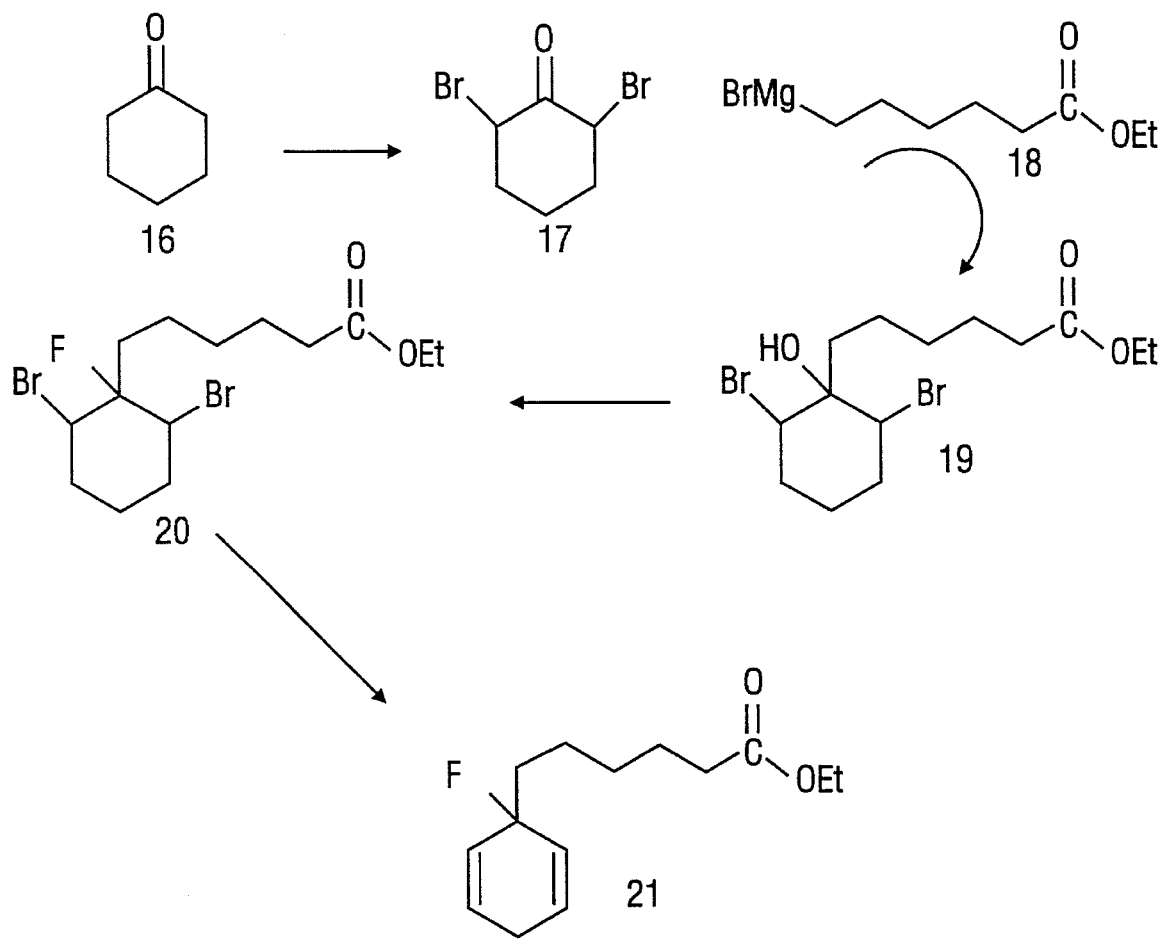
FIG. 4. Schematic representation of the synthesis of compounds 17, and 19 to 21 of Example 1.

Another linolenic acid mimetic is compound 21, the synthesis of which is shown in FIG. 4. Starting from cyclohexanone 16, one can obtain the dibromoketone 17 through reaction with pyridinium bromide perbromide. Reaction of 17 with the Grignard reagent 18 gives the dibromohydroxyl ester 19. Fluorination of 19 at room temperature using DAST gives compound 20, which when stirred with DBU at room temperature undergoes double elimination of HBr to give the target linolenic acid mimetic 21. Again the free acid can be obtained by chemically removing the ester function or by enzymatic hydrolysis in vivo.

3. Synthesis of $C_{17}$-Ring Linolenic Acid Analogs

Figure 5:
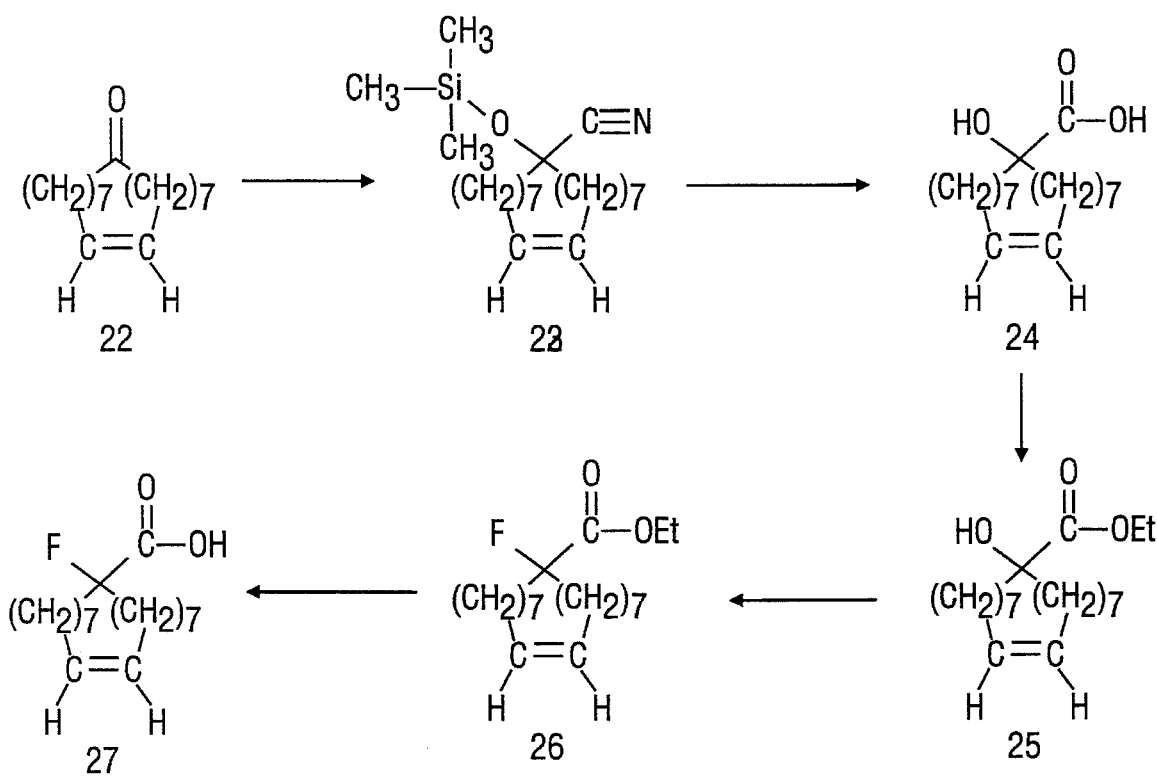
FIG. 5. Schematic representation of the synthesis of compounds 23 to 27 of Example 1.

Cyclic analogs of linolenic acid should be more stable in vivo than linolenic acid itself, due to greater resistance to β-oxidative cleavage. An example of one class of cyclic compounds is compound 27, which is a 17-membered hydrocarbon ring possessing a double bond and the required carboxylic acid group. The synthetic route to compound 27 is depicted in FIG. 5. Starting from civetone 22, the silated cyanohydrin 23 can be formed by reaction with trimethylsilyl cyanide. The cyanohydrin can be converted to the α-hydroxy acid 24 via reduction with stannous chloride and hydrochloric acid. Esterification of 24 gives compound 25, which can be converted to the α-fluoro ester 26 through reaction with DAST. Cleavage of the ester group then gives the free acid 27.

Figure 6:
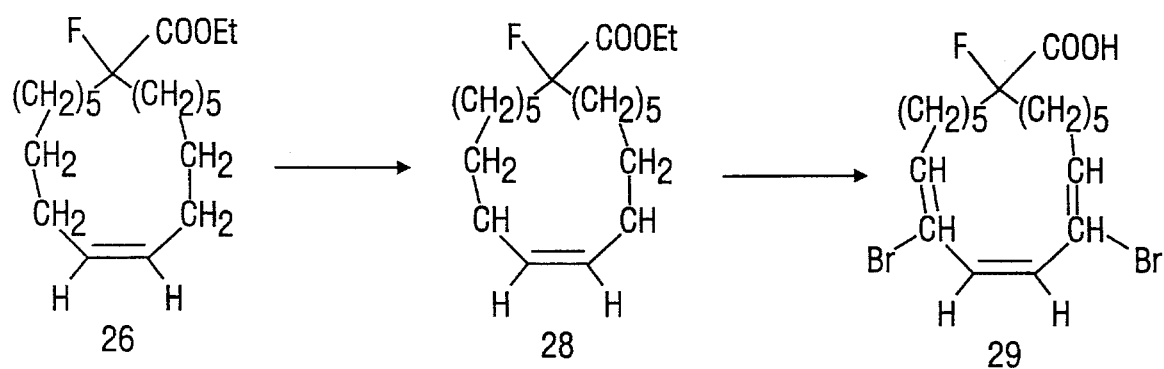
FIG. 6. Schematic representation of the synthesis of compounds 28 and 29 of Example 1.

Fluoro ester 26 can also undergo allelic bromination to give compound 28 (FIG. 6), which undergoes double elimination by reaction with DBU to give the tri-ene 29, most likely as a mixture of cis and trans isomers. Fluoro ester 26 can also be catalytically hydrogenated to give the C17-saturated ring compound as well.

Figure 7:
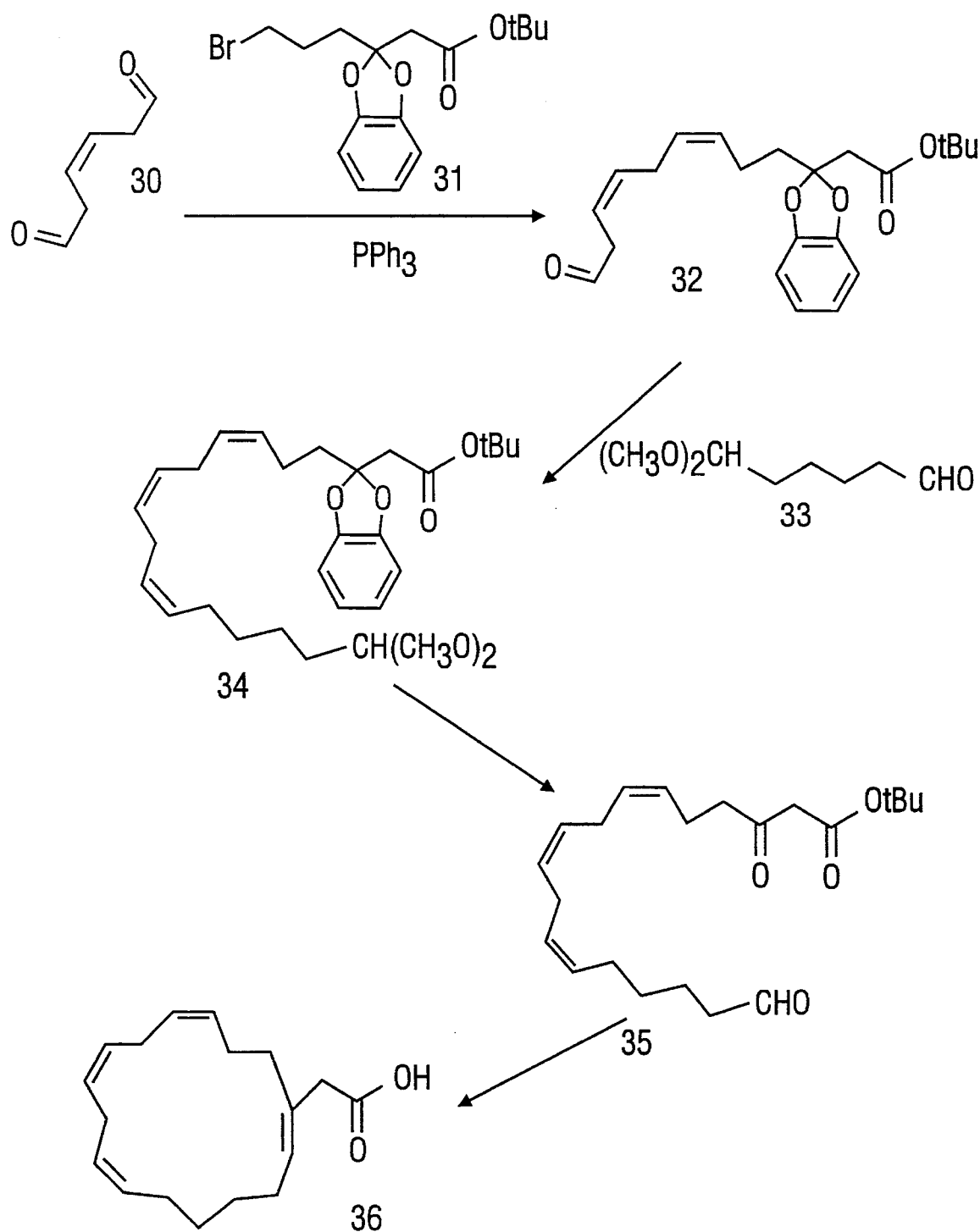
FIG. 7. Schematic representation of the synthesis of compounds 32 and 34 to 36 of Example 1.

4. Synthesis of $C_{16}$-Ring and 16-Membered Hetero Atom-Substituted Ring Linolenic Acid Analogs The synthesis of this class of compounds begins with 3-hexenedial 30 (FIG. 7). Reaction of 30 with compound 31 (prepared in six steps from butyrolactone) and triphenylphosphine gives the Wittig product 32. Reaction of 32 with aldehyde 33 (prepared in four steps from cyclohexene) gives compound 34, which leads to compound 35 after removal of the ketal protecting groups. Compound 36 is obtained from the carbonyl coupling of 35 via titanium (III) chloride and lithium in dry dimethyoxyethane.

Insertion of heteroatoms into the ring system is accomplished by the procedure described in FIG. 7 using compounds with appropriate modification of compound 31. For example, compound 37 can be made from precursors to 31. Compound 37, after reacting with compound 30, yields compound 38 which, after several steps, yields compound 41. Compound 41, stirred in the presence of DBU, can undergo cyclization. After hydrolysis of the ester group, the acid 42 is formed (FIG. 8).

Figure 9:
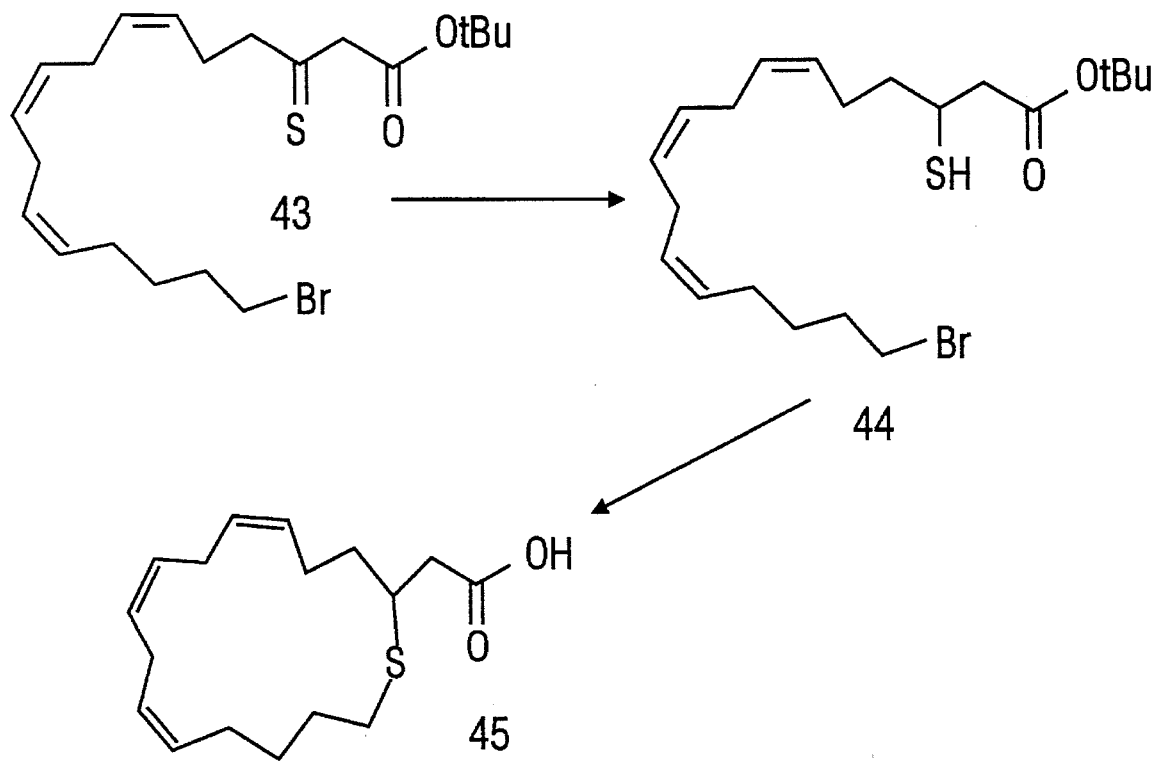
FIG. 9. Schematic representation of the synthesis of compounds 44 and 45 of Example 1 from compound 43 of Example 1.
Figure 10:
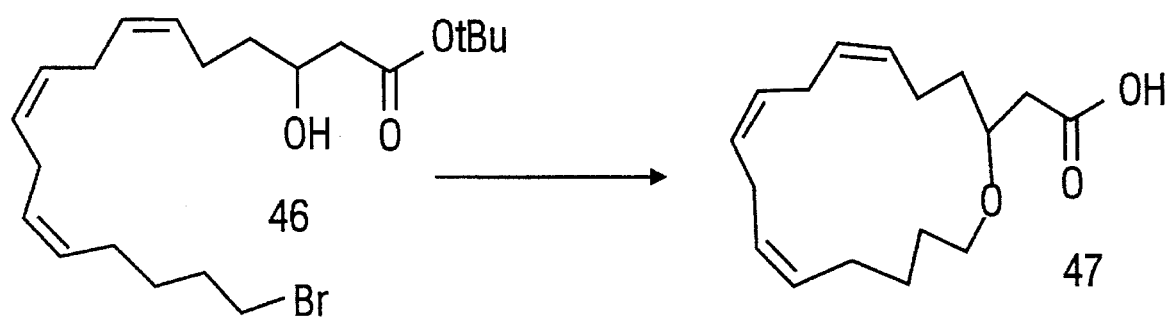
FIG. 10. Schematic representation of the synthesis of compound 47 of Example 1 from compound 46 of Example 1.

The sulfur and oxygen-substituted ring compounds 45 and 47 can be made in an analogous fashion (FIG. 9 and FIG. 10).

5. Synthesis of 17-Membered Hetero Atom-Substituted Ring Linolenic Acid Analogs

Figure 8:
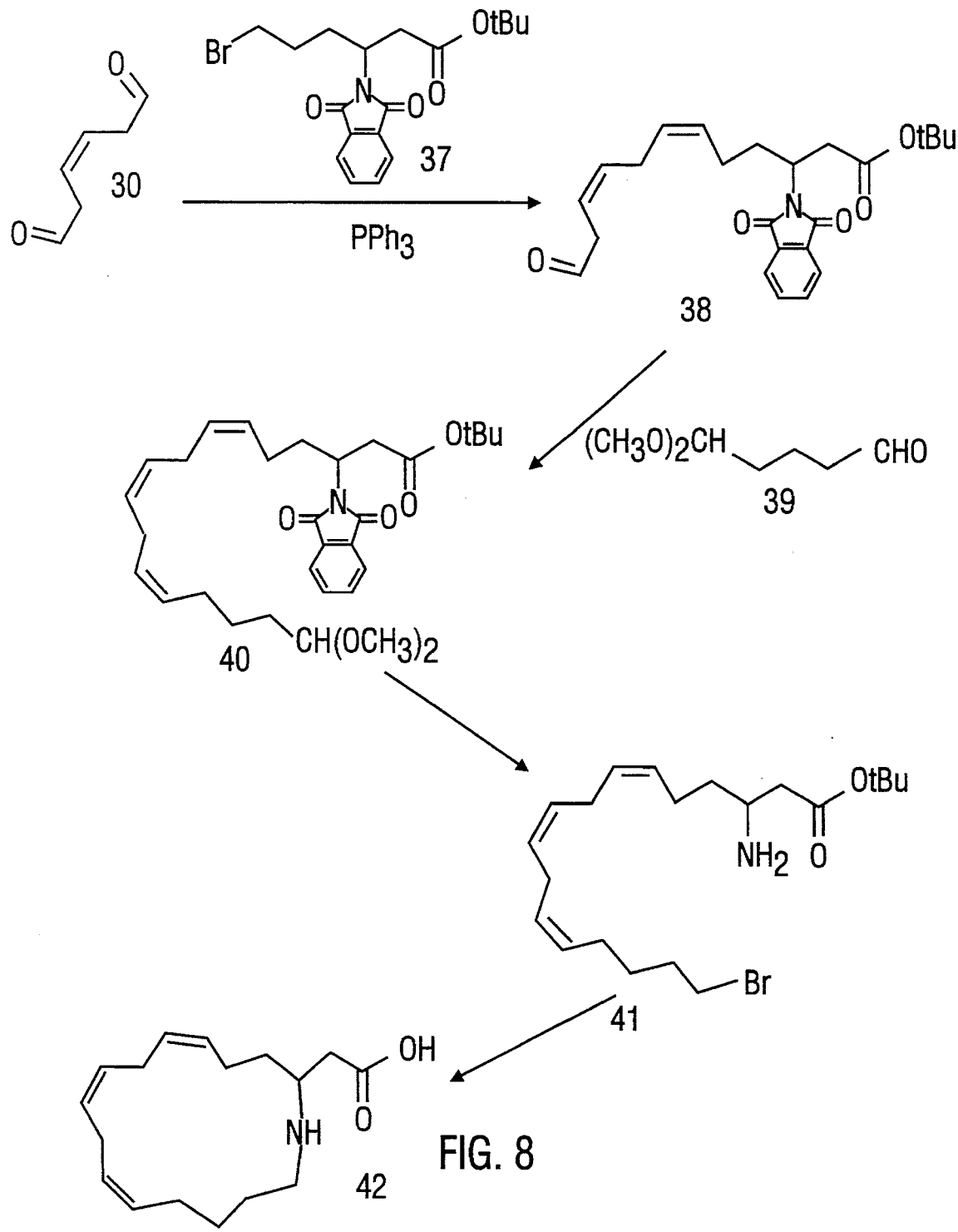
FIG. 8. Schematic representation of the synthesis of compounds 38 and 40 to 42 of Example 1.
Figure 11:
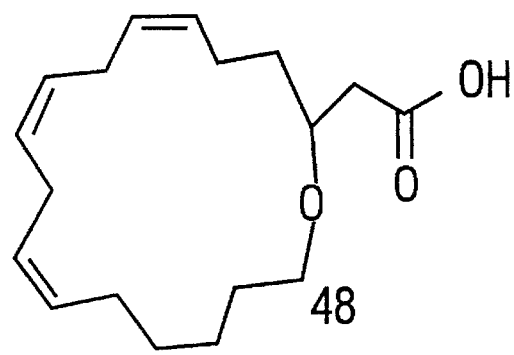
FIG. 11. Structures for compounds 48 to 50 of Example 1 which can be made using the scheme shown in FIG. 8.
Figure 11:
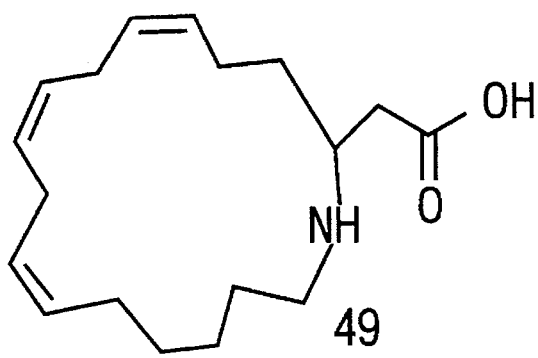
Figure 11:
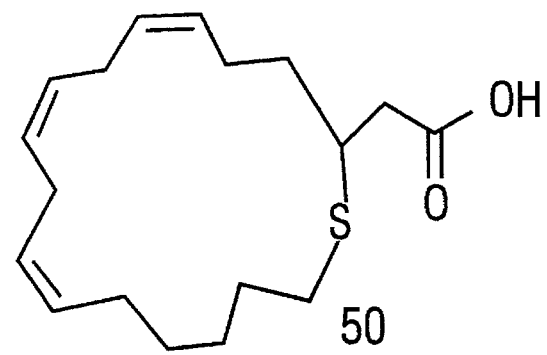
Figure 11:
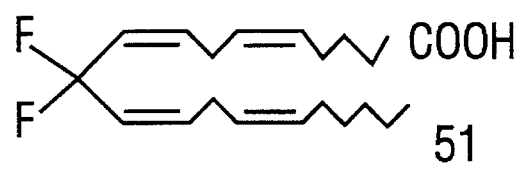
Figure 11:
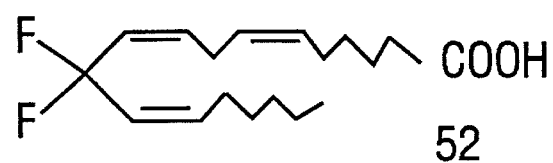

Compounds 48, 49, and 50 (FIG. 11) can be made using the chemistry outlined in FIG. 8 by merely replacing the 5-carbon aldehyde 39 with its 6-carbon homologue 33.

6. Synthesis of Polyunsaturated Fatty Acids With $CF_2$ Group(s) in Between cis Double Bonds A general methodology for the synthesis of unsaturated fatty acids, in which one of the methylene group between cis double bonds is replaced by a $CF_2$ group is available (Kwok et al., 1987). This is exemplified by the preparation of 10, 10-difluoroarachidonic acids (compound 51) and 11, 11-difluoro-γ-linoleic acid (compound 52 in FIG. 11).

7. Chemical Names of Compounds in FIG. 1 to FIG. 11

1. Any acid.
2. The corresponding aldehyde.
3. Ethyl 3-hydroxyacid ester.
4. Ethyl 3-ketoacid ester.
5. Ethyl 3,3-difluoroacid ester.
6. 3,3-Difluoro acid.
7. Any acid chloride.
8. Meldrum's acid adduct.
9. 3-Keto acid.
10. 1,3-Cyclohexanedione.
11. Ethyl 6-bromohexanoate.
12. Ethyl 6-(2,6-cyclohexanedion-yl)hexanoate.
13. Ethyl 6-(2,6-dihydroxycyclo-hexanyl)hexanoate.
14. Ethyl 6-[2,6-bis(trifluoromethane sulfonyl)cyclohexanyl]heaxanoate.
15. Ethyl 6-(cyclohex-2,5-dienyl)hexanoate.
16. Cyclohexanone.
17. 2,6-Dibromocyclohexanone.
18. Ethyl 6-magnesiumbromo-hexanoate.
19. Ethyl 6-(1-hydroxy-2,6-dibromo-cyclohexyl)hexanoate.
20. Ethyl 6-(1-fluoro-2,6-dibromo-cyclohexyl)hexanoate.
21. Ethyl 6-(1-fluoro-cyclohex-2,5-dienyl)hexanoate.
22. Civetone.
23. Civetone trimethylsilyl-cyanohydrin.
24. 1-Hydroxycyclohept-9-ene-1-carboxylic acid.
25. Ethyl 1-hydroxycyclohept-9-ene-1-carboxylate.
26. Ethyl 1-fluorocyclohept-9-ene-1-carboxylate.
27. Ethyl 1-fluorocyclohept-9-ene-1-carboxylic acid.
28. Ethyl 1-fluoro-8,11-dibromocyclohept-9-ene-1-carboxylate.
29. Ethyl 1-fluorocyclohept-7,9,11-triene-1-carboxylic acid.
30. 3-Hexenedial.
31. Tert-butyl 6-bromo-3-ketohex-anoate resorcinol ketal.
32. Tert-butyl 3-keto-dodec-6,9-diene-12-carboxaldehydoate resorcinol ketal.
33. 6,6- Dimethoxyhexanal.
34. Tert-butyl 3-keto-18,18-dimethoxyoctadec-6,9,12-trienoate resorcinol ketal.
35. Tert-butyl 3-ketooctadeca-6,9,12-triene-18-carbox-aldehydoate.
36. 2-(1-Cyclohexadec-1,7,10,13-tetraenyl)acetic acid.
37. Tert-butyl 6-bromo-3-N-phthal-amidohexanoate.
38. Tert-butyl 3-N-phthalamido-dodec-6,9-diene-12-carbox-aldehydoate.
39. 5,5-Dimethoxypentanal.
40. Tert-butyl 3-N-phthalamido-18,18-dimethoxyoctadec-6,9,12-trienoate.
41. Tert-butyl 3-keto-18-bromo-octadeca-6,9,12-trienoate.
42. 2-(2-Azacyclohexadec-7,10,13-trienyl)acetic acid.
43. Tert-butyl 3-thio-18-bromo-octadeca-6,9,12-trienoate.

44. Tert-butyl 3-sulfhydryl-18-bromooctadeca-6,9,12-trienoate.
45. 2-(2-Thiacyclohexadec-7,10,13-trienyl)acetic acid.
46. Tert-butyl 3-hydroxy-18-bromo-octadeca-6,9,12-trienoate.
47. 2-(2-Oxacyclohexadec-7,10,13-trienyl)acetic acid.
48. 2-(2-Oxacycloheptadec-8,11,14-trienyl)acetic acid.
49. 2-(2-Azacycloheptadec-8,11,14-trienyl)acetic acid.
50. 2-(2-Thiacycloheptadec-8,11,14-trienyl)acetic acid.
51. 10,10-Difluoro-arachidonic acid.
52. 11,11-Difluoro-γ-linolenic acid.

EXAMPLE 2

Inhibition of 5α-Reductase Activity

A. ASSAYS

In mammalian cells, 5α-reductase is very tightly associated with intracellular membranes, including the membrane of the endoplasmic reticulum and contiguous nuclear membranes. Attempts to solubilize and purify active 5α-reductase have not been very successful. The assay of 5α-reductase activity, therefore, has been performed by measuring the rate of conversion of testosterone to 5α-DHT by whole cells or by microsomal and nuclear preparations in the presence of NADPH (enzymatic assay). Alternatively, the 5α-reductase activity can be reliably assayed by following NADPH-dependent noncovalent binding of a potent radioactive inhibitor, such as [$^3$H]4-MA ([$^3$H]4-MA-binding assay), which strongly competes with testosterone for binding to the reductase. The results of the two assays correlate very well when microsomal preparations from different organs or animals are used for comparison (Liang et at., 1983).

1. [$^3$H]4-MA Binding Assay for 5α-Reductase

The procedure was described in detail previously (Liang et al., 1983, 1990). Briefly, the binding assay solution, in a final volume of 0.15 ml, contained microsomes (2–20 μg of protein), 0.08 μCi of [$^3$H]4-MA, 0.1 mM-NADPH, 1 mM-dithiothreitol and 50 mM-potassium phosphate, pH 7.0, with or without the indicated amount of a lipid or an inhibitor preparation. Lipids were dissolved in ethanol and added in 1–5 μl volumes. Control tubes received the same amount of ethanol. After incubation at 0° C. for 1 h, the [$^3$H]4-MA bound to microsomes was determined by collecting microsomes on a Whatman GF/1F glass fibre filter and washing with 10 ml of 20 mM-potassium phosphate, pH 7.0, containing 0.01% CHAPS to remove unbound [$^3$H]4-MA.

2. Assay of the Enzymatic Activity of Microsomal 5α-Reductase

The standard reaction mixture, in a final volume of 0.15 ml, contained microsomes (1 μCi of [$^3$H]testosterone, 0.5–3.0 μM non-radioactive testosterone, 0.1 mM-NADPH, 1 mM-dithiothreitol and 50 mM-potassium phosphate, pH 7.0, with or without the indicated amount of a lipid or an inhibitor preparation. The reaction was started by the addition of microsomes and the incubation was carried out at 37° C. for 15 min. Steroids were extracted and separated by t.l.c. as described previously (liang & Heiss, 1981; Liang et al., 1984a, 1985a). Radioactive steroids were located by fluorography and the amount of radioactivity present was determined by scintillation counting. The 5α-reductase activity was measured by analyzing the extent of the conversion of [$^3$H]testosterone to [$^3$H]5α-DHT.

B. SOURCES OF 5α-REDUCTASE ACTIVITY

Microsomes were prepared at 4° C. from a buffered 0.32M-sucrose homogenate of human liver and from the livers of adult Sprague-Dawley female rats by differential centrifugation as described previously (Liang et al., 1990), and were used in the assay of 5α-reductase activity. In some experiments, microsomes were solubilized with 0.1% polyoxyethylene ether W-1 as described previously (Liang et al., 1990), except for the substitution of polyoxyethylene ether W-1 for Lubrol-WX.

Cells genetically engineered to express specific types of 5α-reductase isozymes may also be used as sources of 5α-reductase activity. Intact cells containing 5α-reductase, their microsomes, or nuclear preparation may also be used to screen 5α-reductase inhibitors.

C. INHIBITORS OF 5α-REDUCTASE ACTIVITY

Animal and plant sources were tested for the presence of compounds affecting 5α-reductase activity. Inhibitory activities were found in extracts of rat and beef liver microsomes, beef kidney, human placenta, rat and human prostate as well as in yeast and vegetable plant oils, e.g., corn, peanut and olive oils, indicating the presence of 5α-reductase inhibitors in a wide range of sources including animal, plant and microorganisms.

1. Rat Liver Microsomes

Figure 12:
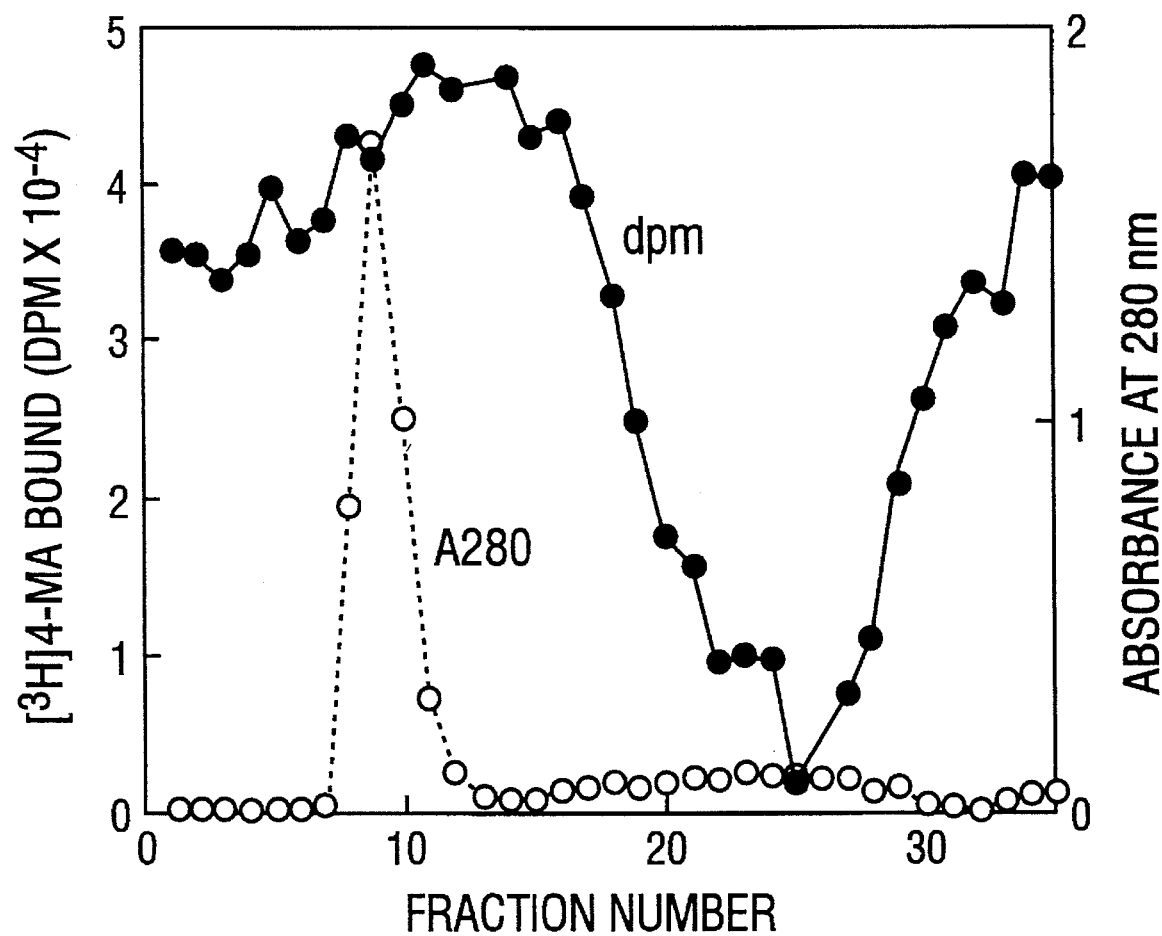
FIG. 12. Fractionation of 5α-reductase inhibitors in the microsomal extract of rat liver by Sephadex® G-50 column chromatography. 5α-reductase was assayed by the [$^3$H]4-MA-binding assay (closed circles). The absorbance at 280 nm for each fraction is also shown (open circles). Most of the inhibitory activity was associated with the fractions No. 19 to No. 29.

When the microsomal fraction of rat liver was solubilized with acetic acid and then mixed with methanol, more than 80% of microsomal proteins were removed as precipitates. This procedure inactivated the 5α-reductase activity completely. The soluble fraction, but not the precipitated fraction, contained compounds that inhibited 5α-reductase activity (determined by the enzymatic assay or [$^3$H]4-MA-binding assay) of rat liver microsomes. As shown in FIG. 12, Sephadex® G-50 column chromatography of the methanol soluble fraction showed separation of the inhibitory activity from the majority of the protein peak which eluted in the void volume. The inhibitory activity was also found in methylene chloride extracts of rat liver microsomes, suggesting that some of the inhibitors were lipids.

2. Plants and Fungi

Preparations were also obtained and specific compounds were isolated from various plant materials. Some of these were able to regulate both the type 1 and type 2 5α-reductase isozymes of rat and human. While some of these agents were inhibitory, other agents stimulated 5α-reductase activities.

Each plant material (1 to 2 g) was extracted by 2 to 10 ml of water, ethanol, isopropyl alcohol, ether, chloroform, or ethyl acetate. Organic solvents can contain 0–90% of water and the extraction can be carried out at 0°–100° C. for 30 minutes to 20 hours.

When 1 g of the plant material was extracted with 4 ml of ethanol or water, and 3 μl of the extract was tested in the liver microsomal 5α-reductase assay system (the final volume of the reaction mixture was 0.15 ml), a significant inhibitory activity (over 20% inhibition) was observed with extracts from various brands of green tea, Yunnan tea, special gunpowder tea, oolong tea, black tea, chlorella, black shiitake mushroom, basil leaves, parsley leaves, and Chinese herbs, including *Angelica sinensis, Anisi stellati fructus, Codonopsis pilosula, Ligustici rhizoma, Salvia mitiorrhiza*, and Golden Lilly flower, seeds of borage, evening primose, black current, sesame, pumpkin, sunflower, and wheat germ.

The inhibitory substances in basil, oolong tea, green tea, and *Angelica sinensis*, could be separated from other inactive substances by one or two dimensional silica gel thin-layer chromatography or by Sephadex™ gel column chromatography. The chemical structures of some purified compounds were determined by comparing their chemical properties with that of standard compounds, including chromatographic mobility, melting point, ultra-violet and visible-light spectra and NMR. Commercially-available standard compounds were also used in 5α-reductase assays to show that some of them were indeed 5α-reductase inhibitors that inhibit the formation of 5α-DHT.

3. Fatty Acids

Certain long chain fatty acids were found to inhibit 5α-reductase activity. The assay procedures and active compounds are described in Example 3. In general, it was found that long chain polyunsaturated fatty acids were most effective, particularly those with at least two double bonds and with a chain length of at least 12.

4. Catechins and Epicatechin Gallates

Figure 20A:
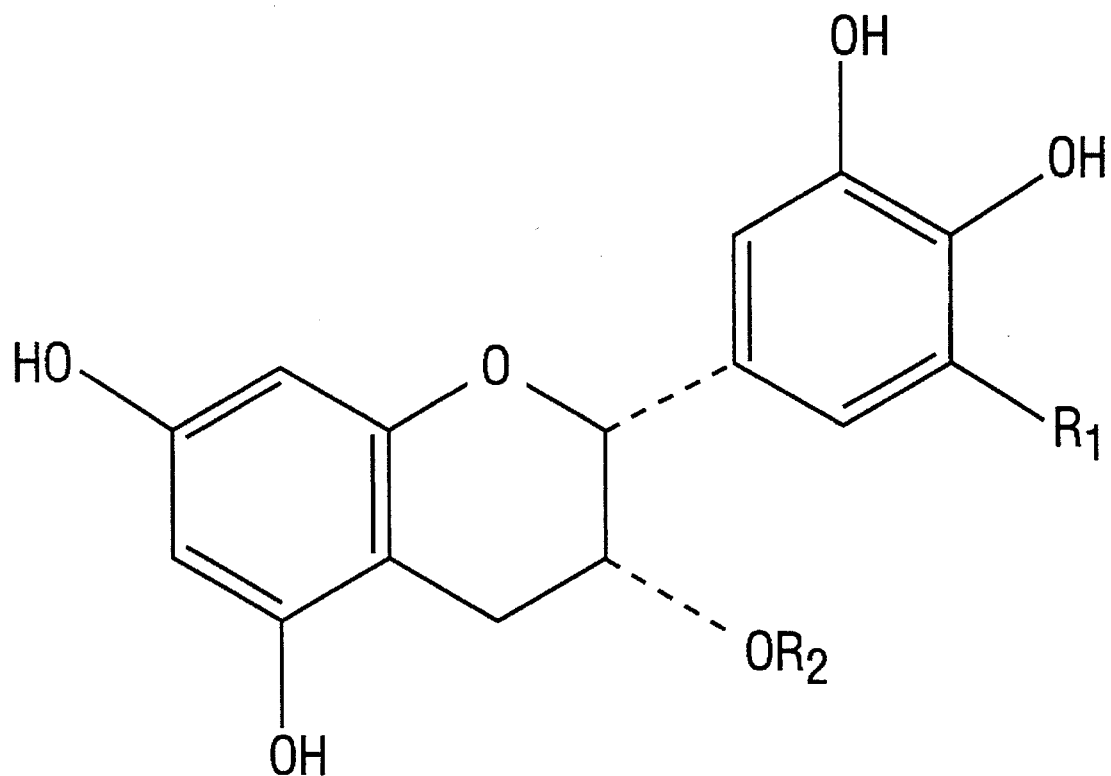
FIG. 20A. General structure of catechin derivatives.
Figure 20B:
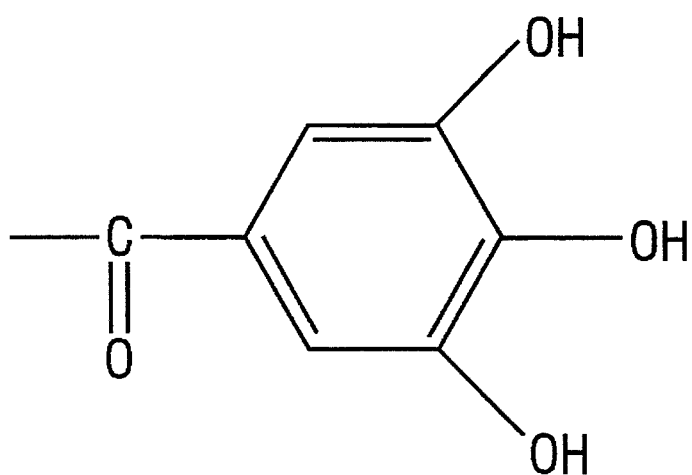
FIG. 20B. Structure of galloyl moiety.
Figure 21:
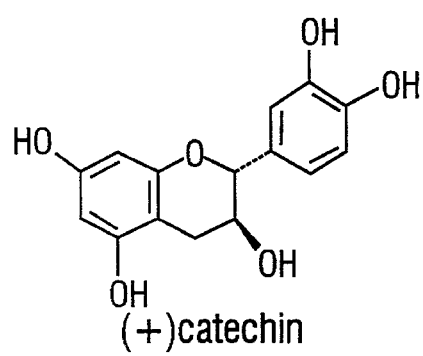
FIG. 21. Structure of important catechins.
Figure 21:
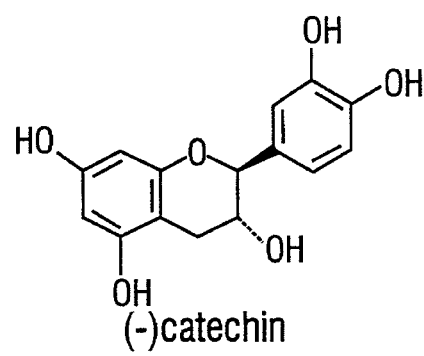
Figure 21:
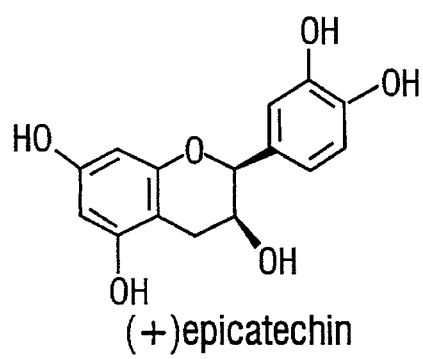
Figure 21:
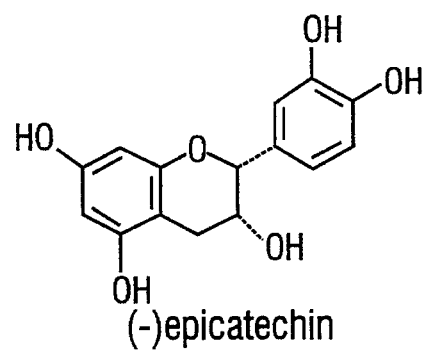
Figure 21:
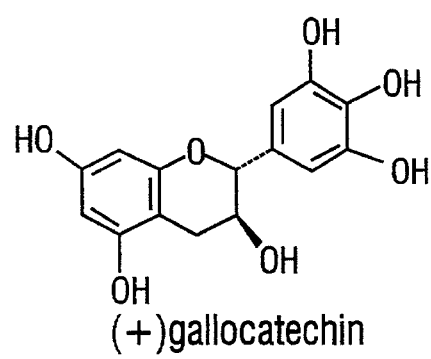
Figure 21:
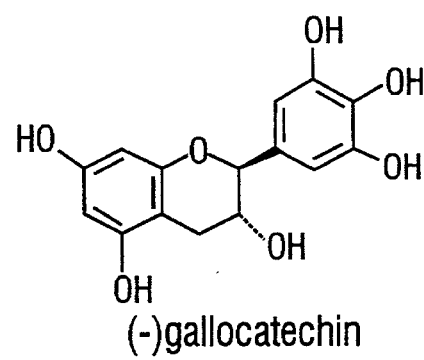
Figure 21:
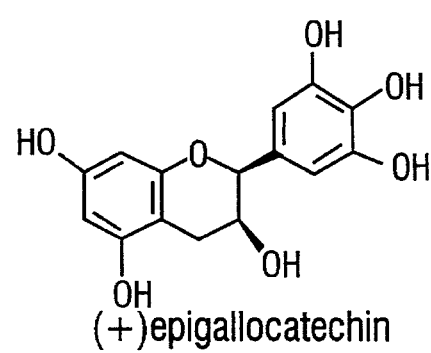
Figure 21:
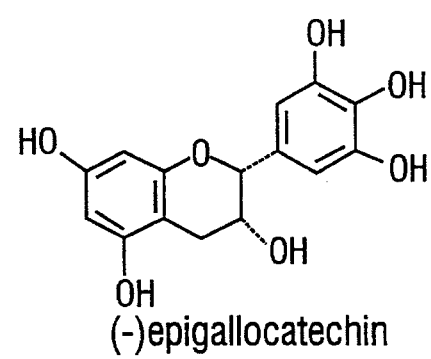
Figure 22:
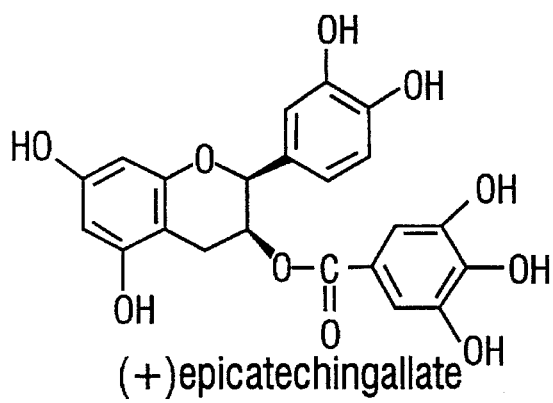
FIG. 22. Structure of important catechin gallates.
Figure 22:
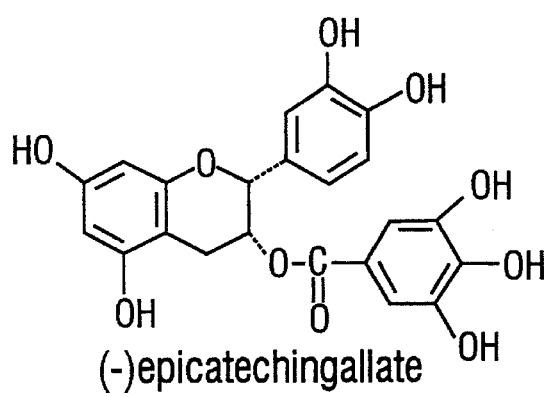
Figure 22:
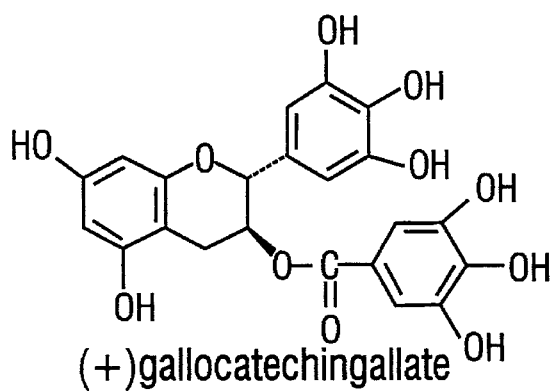
Figure 22:
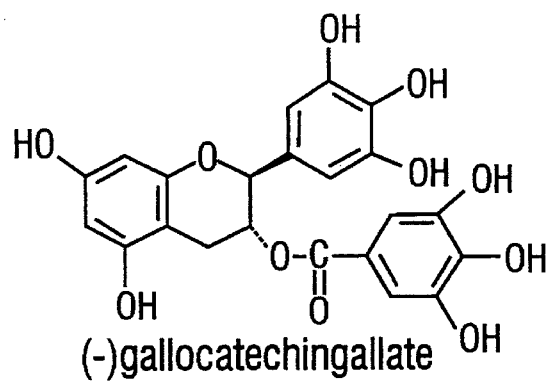
Figure 22:
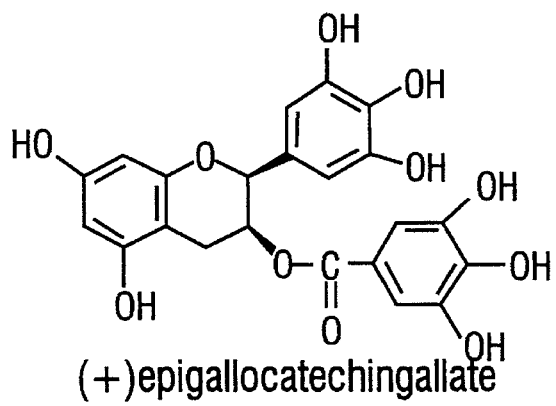
Figure 22:
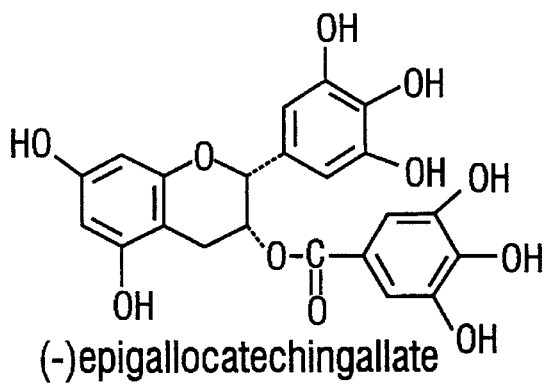

The major inhibitory substances in various brands of tea preparations, especially in green tea, were found to be catechin derivatives (FIG. 20A). Catechins without a galloyl (FIG. 20B) substitution (FIG. 21) were much less active than catechin gallate, epicatechin gallate, epigallocatechin gallate, and their optical isomers (FIG. 22) or their conjugated substances such as theaflavins and theaflavin mono- (or di-) gallates. These gallates showed significant inhibitory activities (30 to 90% inhibition) at concentrations of 0.5 to 40 µM in the assay systems containing (a) rat liver microsomal preparations or (b) cells infected with retrovirus containing genes for type 1 or type 2 5α-reductases and expressing specific type of the reductases. Catechin and epicatechin (FIG. 21) were much less active (less than 25% inhibition at 40 µM).

Although these inhibitory polyphenolic substances are antioxidants, they did not significantly oxidize NADPH under the assay conditions (in the presence of liver microsomal preparation and in the absence of testosterone or 4-MA, indicating that the inhibitory activity was due to the inhibition of 5α-reductases and not due to a nonspecific oxidation of NADPH by these polyphenols.

Various synthetic gallate derivatives (methyl gallate, n-propyl gallate, 3,4,5-trihydroxybenzamide), gallic acid, and pyrogallol were not as active as catechin gallate. This indicated that the gallol or galloyl structure alone was not sufficient for the high inhibitory activity. A low inhibitory activity was found with n-octyl gallate, indicating that, for the inhibitory activity, the flavonol group of catechin gallates may be replaced by other alcoholic group having similar geometric structures.

Figure 23:
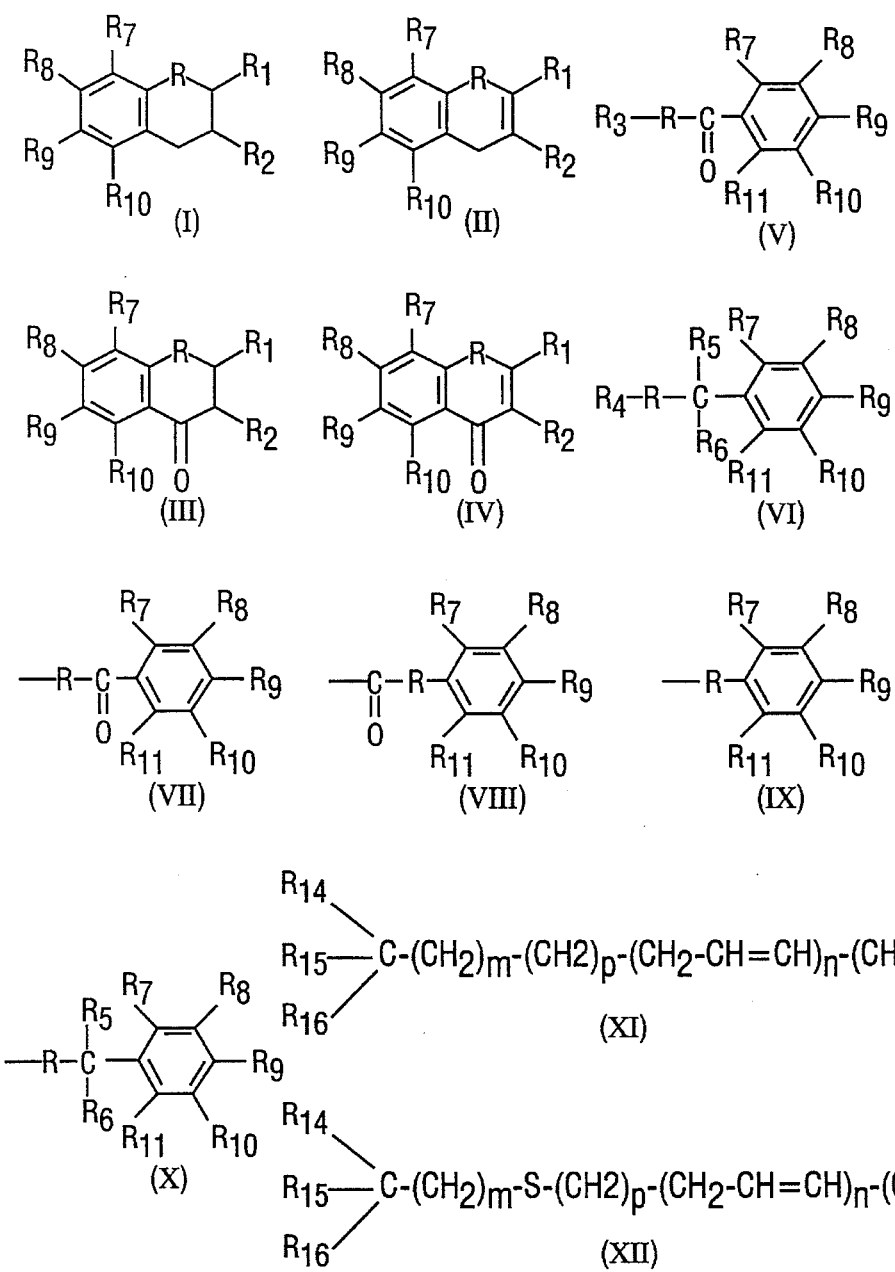
FIG. 23. Novel classes of 5α-reductase inhibitors. R1 and R2 are alkyl, allyl, or groups having general structures of VII, VIII, IX, X, XI, XII. R3 and R4 are groups having general structures of XI or XII. R5 and R6 are hydrogen or halogen atoms. R7, R8, R9, R10, R11, R12, R13, R14, R15, and R16 are hydrogen, halogen, hydroxyl, methyl, ethyl, methoxyl, acetyl, or acetoxyl group. R is oxygen, nitrogen, or sulfur atom.

The results indicated that the gallate moiety incorporating an acyl (galloyl) or alcoholic (trihydroxybenzyl) group may be required for inhibition of 5α-reductase. These groups may form an ester or ether linkage with the flavonol (FIG. 23).

EXAMPLE 3

Fatty Acid Inhibition of 5α-Reductase Activity

Identification of compounds that inhibited 5α-reductase utilized two types of assays; an enzymatic assay and a binding assay as described in Example 2. Both assays identified similar activities for the active fatty acids.

When various lipids were tested for their ability to affect binding of [$^3$H]4-MA to rat liver microsomes, only certain unsaturated fatty acids were inhibitory, as shown in Tables 1 and 2. Among the lipids tested, the highly inhibitory fatty acids have 14 to 22 carbon chains and one to six double bonds. The presence of a double bond was required for higher inhibitory activity; saturated fatty acids were generally not as active as corresponding unsaturated fatty acids. With the [$^3$H]4-MA binding assay, only compounds with double bonds in the cis configuration were active at low concentrations (<10 µM), whereas the trans isomers were inactive even at high concentrations (>0.2 mM). However, as is shown in Example 4, the trans isomers were active inhibitors when the reductase activity was analyzed using the enzyme assay. The difference in the effect of cis and trans isomers of fatty acids in the [$^3$H]4-MA binding assay is obvious when the following sets of fatty acids are compared: oleic acid (C18:1, cis-9) vs. elaidic acid (C18:1, trans-9) and linoleic acid (C18:2, cis-9,12) vs. linolelaidic acid (C18:2, trans-9,12). The results presented in Tables 1 and 2 also demonstrate that the number and the position of the double bonds also affected the potency. When the [$^3$H]4-MA binding assay was used, the inhibitory potency for the C18 fatty acids were, in decreasing order: γ-linolenic acid (cis-6,9,12)>cis-6,9,12,15-octadecatetraenoic acid>α-linolenic acid (cis-9,12,15)>linoleic acid (cis-9,12)>oleic acid (cis-9)>petroselinic acid (cis-6). Erucidic acid (C22:1, cis-13) was inactive; whereas cis-4,7,10,13,16,19-docosahexaenoic acid was a potent inhibitor. Undecylenic acid (C11:1,10) and nervonic acid (C24:1, cis-15) were also inactive.

A free carboxyl group is important since the methyl ester and alcohol analogs of these inhibitory unsaturated fatty acids were either inactive or only slightly active. Prostaglandin E2, F2a and 12 were not active; whereas the prostaglandin A1, A2, B1, B2, D2, E1, and F1a were somewhat active at 0.2 mM. Carotenes, retinals, and retinoic acid were also inactive. Phosphatidylcholine, phosphatidyl ethanolamine, 3-diolein, retinol, 13-cis-retinoic acid, and 13-cis-retinol were slightly stimulatory.

When the inhibitory effects of fatty acids were tested by the enzymatic assay, the relative potency of saturated and cis-unsaturated fatty acids were in agreement with that obtained by the [$^3$H]4-MA-binding assay (Tables 1 and 2), regardless of whether rat liver microsomes or prostate microsomes were used as the source of the enzyme. The trans isomers, elaidic acid (C18:1, trans-9) and linolelaidic acid (C18:2, trans-9,12) were much less inhibitory than their cis isomers, oleic acid (C18:1, cis-9) and linoleic acid (C18:2, cis 9,12), in the [$^3$H]4-MA binding assay (Tables 1 and 2, and FIG. 13A); however, they were as potent as their cis isomers in the enzymatic assay using either prostate microsomes or liver microsomes (FIG. 13B). The results suggested that the trans isomers inhibited 5α-reductase through a different mechanism.

TABLE 1

Inhibition of [$^3$H]4-MA Binding to 5α-Reductase of Rat Liver Microsomes by Lipids

| Test compounds | Numeric symbol # | % Inhibition of [$^3$H]4-MA binding* Concentration of test compounds | | |
|---|---|---|---|---|
| | | 10 µM | 40 µM | 200 µM |
| Control (no addition) | | | | |
| Undecylenic acid | C11:1 (10) | | NA | 13 ± 2 |
| Myristoleic acid | C14:1 (cis-9) | NA | 25 ± 4 | 43 ± 1 |
| Palmitic acid | C16:0 | | | NA |
| Palmitoleic acid | C16:1 (cis-9) | NA | 16 ± 5 | 73 ± 7 |
| Palmitoleic acid methyl ester | | | NA | NA |
| Palmitoleyl alcohol | | | NA | 16 ± 4 |
| Stearic acid | C18:0 | NA | NA | NA |
| Petroselinic acid | C18:1 (cis-6) | | NA | 52 ± 9 |
| Oleic acid | C18:1 (cis-9) | NA | 16 ± 6 | 63 ± 12 |
| Elaidic acid | C18:1 (trans-9) | NA | NA | NA |
| Oleic acid methyl ester | | | NA | NA |
| Oleyl alcohol | | | NA | NA |
| Linoleic acid | C18:2 (cis- | NA | 12 ± 3 | 86 ± 4 |

TABLE 1-continued

Inhibition of [³H]4-MA Binding to 5α-Reductase
of Rat Liver Microsomes by Lipids

| Test compounds | Numeric symbol # | % Inhibition of [³H]4-MA binding* Concentration of test compounds | | |
|---|---|---|---|---|
| | | 10 μM | 40 μM | 200 μM |
| Linolelaidic acid | C18:2 (trans-9,12) | | NA | 19 ± 5 |
| Linoleic acid methyl ester | | | NA | NA |
| Linoleyl alcohol | | NA | NA | 25 ± 5 |
| α-Linolenic acid | C18:3 (cis-9,12,15) | 19 ± 3 | 27 ± 7 | 84 ± 6 |
| α-Linolenic acid methyl ester | | NA | NA | NA |
| α-Linolenyl alcohol | | NA | NA | 24 ± 1 |
| γ-Linolenic acid | C18:3 (cis-6,9,12) | 50 ± 2 | 83 ± 12 | 96 ± 2 |
| Octadecatetraenoic acid | C18:4 (cis-6,9,12,15) | NA | 40 ± 6 | 88 ± 2 |
| Arachidonic acid | C20:4 (cis-5,8,11,14) | NA | 30 ± 10 | 88 ± 5 |
| Docosahexaenoic acid | C22:6 (cis-4,7,10,13,16,19) | NA | 27 ± 1 | 87 ± 6 |
| Erucic acid | C22:1 (cis-13) | | NA | NA |
| Nervonic acid | C24:1 (cis-15) | | NA | NA |

Lipids were tested at concentrations ranged from 0.01 to 0.2 mM. Each study was carried out in duplicates and several experiments were performed to assure that the results shown are representative. Compounds that showed less than 10% inhibition were considered not active (NA). At 200 μM, no significant effect was observed with
(a) saturated aliphatic fatty acids including caproic acid, heptanoic acid, caprylic acid, nonanoic acid, capric acid, undecanoic acid, lauric acid, tridecanoic acid, myristic acid, pentadecanoic acid, nonadecanoic acid, arachidic acid, heneicosanoic acid, behenic acid, tricosanoic acid, and lignoceric acid,
(b) fatty acyl esters and alcohols including stearic acid methyl ester, S-stearoyl CoA, palmitic acid methyl ester, S-palmitoyl CoA, cis-9-tetradecenol, and arachidonyl alcohol, and
(c) vitamin A related compounds including α- and β-carotenes, retinoic acid, 9-cis-retinal, retinal, and 13-cis-retinal. At this high concentration, some aliphatic lipids showed inhibitory activities that were significantly lower than the corresponding unsaturated fatty acids (percent inhibition in the parentheses): myristoleic acid methyl ester (27%), γ-linolenic acid methyl ester (32%), and cis-4,7,10,13,,16,19- docosahexenol (51%). Retinal, 13-cis retinoic acid, and 13-cis-retinol showed 58% stimulation at 200 μM but no stimulation or inhibition at 40 μM. IC50 (the concentrations needed to show 50% inhibition) for potent fatty acids were: γ-linolenic acid (10 μM), octadecatetraenoic acid (57 μM), γ-linolenic acid (60 μM), arachidonic acid (65 μM), palmitoleic acid (108 μM), linoleic acid (117 μM), and oleic acid (128 μM).
The numeric symbol indicates the number of carbon atoms and double bondS in the molecule. The numbers in parentheses indicate the position of double bonds (numbered from the carboxyl end) in cis- or trans-forms.

In addition to the compounds shown in Table 1, the fatty acids, their methyl esters and glycerides shown in Table 2 were tested. The carbon chain length of these fatty acids ranged from 11 to 24 carbons with one to 6 double bonds. Some of the inhibitory compounds and the concentrations required for 50% inhibition (shown in parenthesis; NA indicates not inhibitory at 200 μM or lower concentrations) are: 10-pentadecenoic acid (100 μM), 10-heptadecenoic acid (28 μM), 10-trans-heptadecenoic acid (NA), methyl 10-heptadecenoate (NA), 13-octadecenoic acid (93 μM), 12-octadecenoic acid (NA), 11-octadecenoic acid (26 μM), monogamma linolenin (86 μM), γ-linolenyl alcohol (NA), γ-linolenyl acetate (NA), methyl γ-linolenate (NA), cholesteryl γ-linolenate (NA), di-γ-linolenin (NA), γ-linolenoyl chloride (NA), tri-γ-linolenin (NA), 6,9,12,15-octadecatetraenoic acid (74 μM), nonadecane nitrile (NA), 12-nonadecenoic acid (90 μM), 10-nonadecenoic acid (130 μM), 10-trans nonadecenoic acid (NA), 10,13-nonadecadienoic acid (86 μM), linoleyl cyanide nitrile (NA), linolelaidyl cyanide nitrile (NA), 11 eicosenoic acid (146 μM), 8-eicosenoic acid (48 μM), 5-eicosenoic acid (NA), 11,14 eicosadienoic acid (131 μM), trans 11,14-eicosadienoic acid (NA), methyl 11,14 eicosadienoate (NA), 11,14-eicosadienoyl chloride (NA), 11,14,17-eicosatrienoic acid (29 μM), 11,14, 17-eicosatrienoyl chloride (NA), 8,11,14-eicosatrienoic acid (15 μM), homo-γ-linolenoyl chloride (NA), methyl homo-γ-linolenate (NA), 5,8,11-eicosatrienoic acid (50 μM), archidoyl chloride (NA), heneicosenoic acid (154 μM), heneicosene nitrile (NA), erucic acid (NA), 13,16-docosadienoic acid (118 μM), 13,16,19-docosatrienoic acid (163 μM), methyl 13,16,19-docosatrienoate (NA), 7,10,13,16-docosatetraenoic acid (46 μM), methyl docosatetraenoate (NA), 4,7,10,13,16,19-docosahexaenoic acid (47 μM), 14 tricosenoic acid (NA), 15-tetracosanoic acid (NA).

TABLE 2

Inhibition of [³H]4-MA Binding to 5α-Reductase
of Rat Liver Microsomes by Lipids

| Test compounds | Numeric symbol # | % Inhibition of [³H]4-MA binding* Concentration of test compounds | | | |
|---|---|---|---|---|---|
| | | 5 μM | 10 μM | 40 μM | 200 μM |
| Control (no addition) | | | | | |
| Undecylenic Acid | C11:1 (cis-10) | | NA | NA | 13 |
| Myristoleic Acid | C14:1 (cis-9) | NA | NA | 25 | 43 |
| 10-Pentadecenoic Acid | C15:1 (cis-10) | NA | NA | NA | 71 |
| Palmitic Acid | C16:0 | | | | NA |
| Palmitoleic Acid | C16:1 (cis-9) | | NA | 16 | 73 |
| Palmitelaidic Acid | C16:1 (trans-9) | | | | NA |
| 10-cis-Heptadecenoic Acid | C17:1 (cis-10) | | NA | 83 | 84 |
| 10-trans-Heptadecenoic Acid | C17:1 (trans-10) | NA | NA | NA | 40 |
| Stearic Acid | C18:0 | | NA | NA | NA |
| 11-Octadecenoic Acid | C18:1 (cis-11) | NA | 14 | 55 | 81 |
| 12-Octadecenoic Acid | C18:1 (cis-12) | NA | NA | NA | NA |
| 13-Octadecenoic Acid | C18:1 (cis-13) | NA | NA | NA | 57 |
| trans-Vaccenic Acid | C18:1 (trans-11) | | | | 39 |
| Oleic Acid | C18:1 (cis-9) | NA | NA | 16 | 63 |
| Elaidic Acid | C18:1 (trans-9) | | NA | NA | NA |
| Petroselinic Acid | C18:1 (cis-6) | | | NA | 52 |
| Linoleic Acid | C18:2 (cis-9,12) | | NA | 12 | 86 |
| Linolelaidic Acid | C18:2 (trans-9,12) | | NA | NA | 19 |
| α-Linolenic Acid | C18:3 (cis-9,12,15) | NA | 19 | 27 | 84 |
| Linolenoyl Chloride | chloride | | | | NA |
| γ-Linolenic Acid | C18:3 (cis-6,9,12) | 30 | 50 | 83 | 96 |
| Mono-γ-Linolenin | monoglyceride | NA | NA | 35 | 87 |
| γ-Linolenyl Alcohol | alcohol | NA | NA | NA | 41 |
| γ-Linolenyl Acetate | acetate | NA | NA | NA | 27 |
| Di-γ-Linolenin | Diglyceride | | NA | NA | NA |
| γ-Linolenoyl Chloride | chloride | | NA | NA | NA |
| Tri-γ-Linolenin | triglyceride | NA | NA | NA | NA |
| 6,9,12,15-Octadera-tetraenoic Acid | C18:4 (cis-6,9,12,15) | | NA | 40 | 88 |
| 10-cis-Nonadecenoic Acid | C19:1 (cis-10) | NA | NA | 13 | 79 |
| 10-trans-Nonadecenoic Acid | C19:1 (trans-10) | NA | NA | NA | 32 |
| 12-cis-Nonadecenoic Acid | C19:1 (cis-12) | NA | NA | 32 | 91 |
| 10,13-Nonadecadienoic Acid | C19:2 (cis-10,13) | NA | NA | 37 | 83 |
| 5-Eicosenoic Acid | C20:1 (cis-5) | NA | NA | NA | NA |

TABLE 2-continued

Inhibition of [$^3$H]4-MA Binding to 5α-Reductase
of Rat Liver Microsomes by Lipids

| Test compounds | Numeric symbol # | % Inhibition of [$^3$H]4-MA binding* Concentration of test compounds | | | |
|---|---|---|---|---|---|
| | | 5 μM | 10 μM | 40 μM | 200 μM |
| 8-Eicosenoic Acid | C20:1 (cis-8) | 14 | 41 | 52 | 81 |
| 11-Eicosenoic Acid | C20:1 (cis-11) | NA | NA | 15 | 76 |
| 11,14-cis-Eicosadienoic Acid | C20:2 (cis-11,14) | NA | NA | NA | 89 |
| 11,14-trans-Eicosadienoic Acid | C20:2 (trans-11,14) | NA | NA | NA | NA |
| 11,14-cis-Eicosadienoate | methyl ester | NA | NA | NA | NA |
| 11,14-cis-Eicosaidienoyl Chloride | chloride | NA | NA | NA | NA |
| 11,14,17-cis-Eicosatrienoic Acid | C20:3 (cis-11,14,17) | NA | 1 | 78 | 94 |
| 11,14,17-cis-Eicosatrienoyl Chloride | chloride | NA | NA | NA | NA |
| 8,11,14-cis-Eicosatrienoic Acid | C20:3 (cis-8,11,14) | | 42 | 92 | 82 |
| Arachidonic Acid | C20:4 (cis-5,8,11,14) | | NA | 30 | 88 |
| Arachidoyl Chloride | chloride | | NA | NA | NA |
| Heneicosenoic Acid | C21:1 (cis-12) | NA | 15 | 25 | 60 |
| Erucic Acid | C22:1 (cis-13) | | NA | NA | NA |
| 13,16-Docosadienoic Acid | C22:2 (cis-13,16) | NA | NA | 21 | 93 |
| 13,16,19-Docosatrienoic Acid | C22:3 (cis-13,16,19) | NA | NA | NA | 65 |
| 7,10,13,16-Docosatetraenoic Acid | C22:4 (cis-7,10,13,16) | NA | NA | 41 | 79 |
| 4,7,10,13,16,19-Docosahexenoic Acid | C22:6 (cis-4,7,10,13,16,19) | NA | 18 | 49 | 86 |
| 14-Tricosenoic Acid | C23:1 (cis-14) | NA | NA | NA | 36 |
| 15-Tetracosenoic Acid | C24:1 (cis-15) | | | NA | NA |

EXAMPLE 4

γ-Linolenic Acid Inhibition of 5α-Reductase

γ-LA appeared to be one of the more potent inhibitors of 5α-reductase and was therefore further examined with respect to its 5α-reductase binding characteristics.

1. 5α-reductase Inhibition

Figure 14:
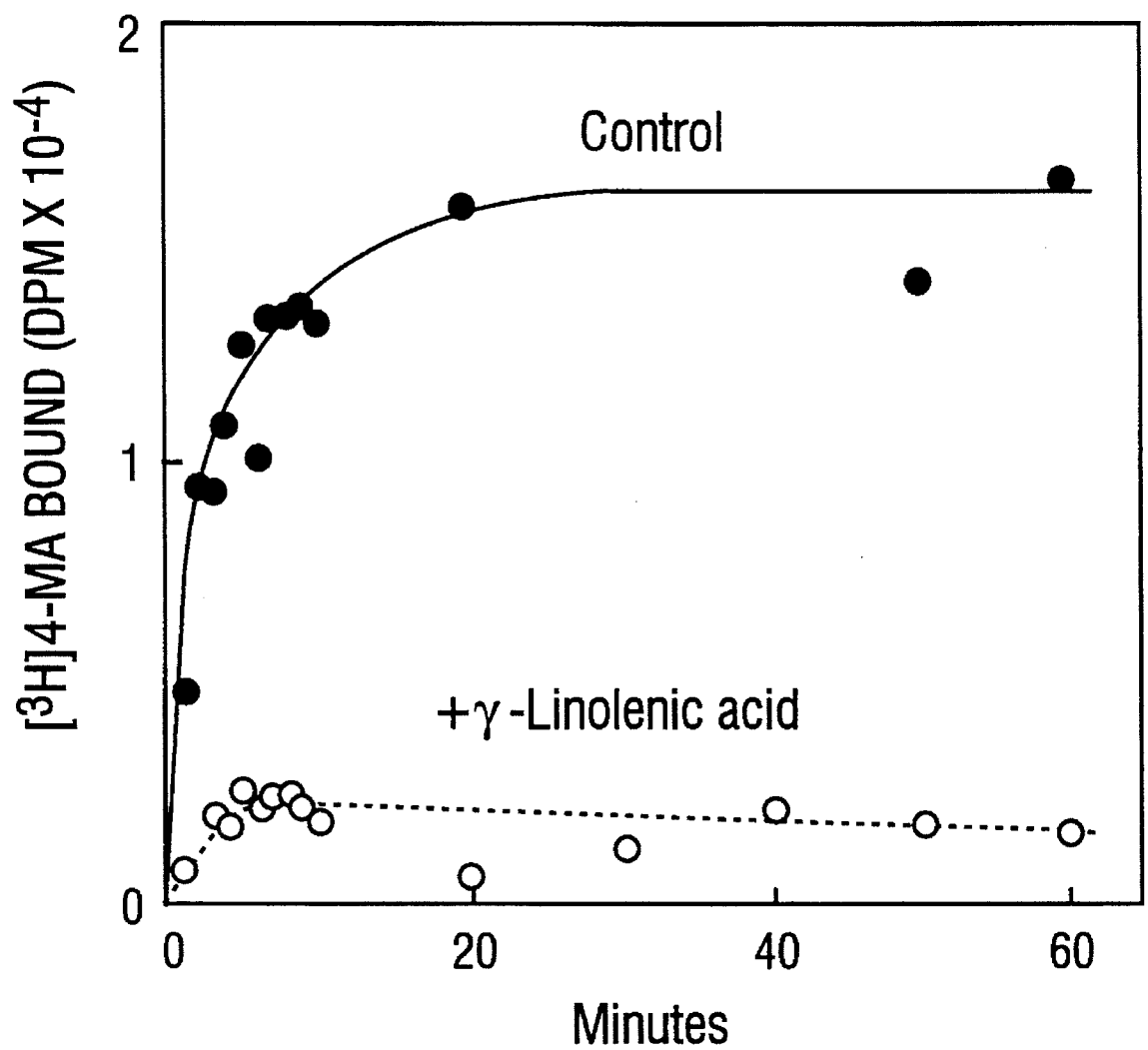
FIG. 14. Time course of γ-linolenic acid inhibition of [$^3$H]4-MA-binding to rat liver microsomes (5 μg protein). The concentration of γ-linolenic acid was 5 μM.
Figure 15B:
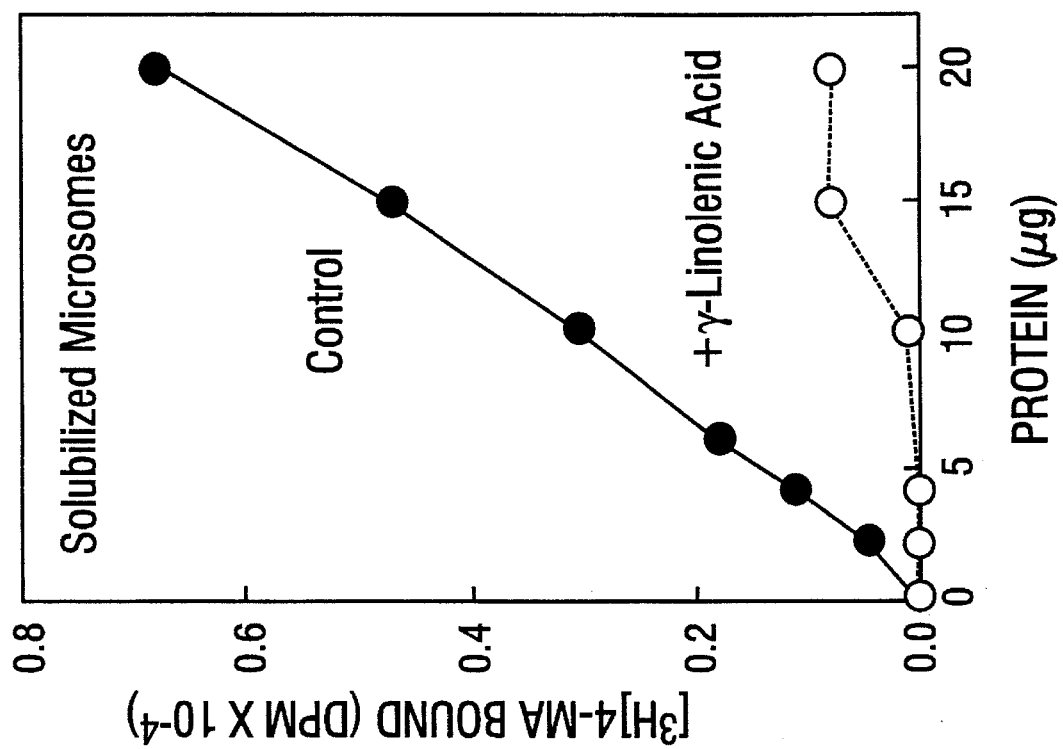
FIG. 15B. Inhibition of [$^3$H]4-MA binding to 5α-reductase in detergent-solubilized rat liver microsomes by γ-linolenic acid. The [$^3$H]4-MA-binding assay was carried out in the absence (control) and presence of 10 μM of γ-linolenic acid and varying amounts of microsomal protein.
Figure 15A:
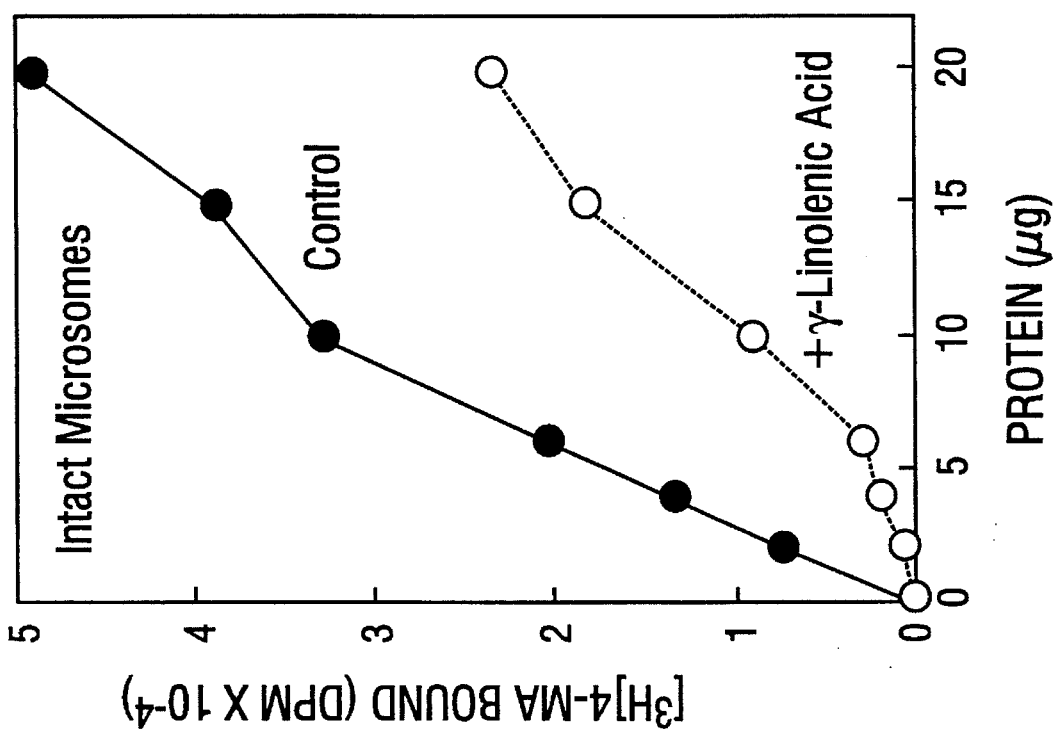
FIG. 15A. Inhibition of [$^3$H]4-MA binding to 5α-reductase in intact rat liver microsomes by γ-linolenic acid. The [$^3$H]4-MA-binding assay was carried out in the absence (control) and presence of 10 μM of γ-linolenic acid and varying amounts of microsomal protein.

With either the enzymatic assay or with the [$^3$H]4-MA binding assay (FIG. 14), inhibition was observed within a minute after γ-LA was mixed with the microsomal enzyme preparation and was observed with both intact (FIG. 15A) and detergent (polyoxyethylene ether) solubilized (FIG. 15B) rat liver microsomes. As the concentration of protein increased from 2 to 20 μg, the extent of inhibition by 10 μM γ-LA decreased from 93% to 52% for intact microsomes and from 96% to 88% for solubilized microsomes.

When [$^3$H]4-MA was allowed to bind to microsomes in the presence of NADPH, followed by addition of γ-LA to a final concentration of 10 μM, about 60% of the microsome-bound [$^3$H]4-MA dissociated from the microsomes within 2 min. The remaining microsome-bound [$^3$H]4-MA dissociated at a much slower rate over the next 60 min. To determine whether γ-LA inhibition is reversible, microsomes were incubated with γ-LA and then reisolated to remove free γ-LA. The results showed that the inhibition was only partially reversed (reduced from 78% to 63% inhibition). It is possible that γ-LA was bound tightly to microsomes and/or irreversibly inactivated components which were essential for the reductase activity.

Figure 16B:
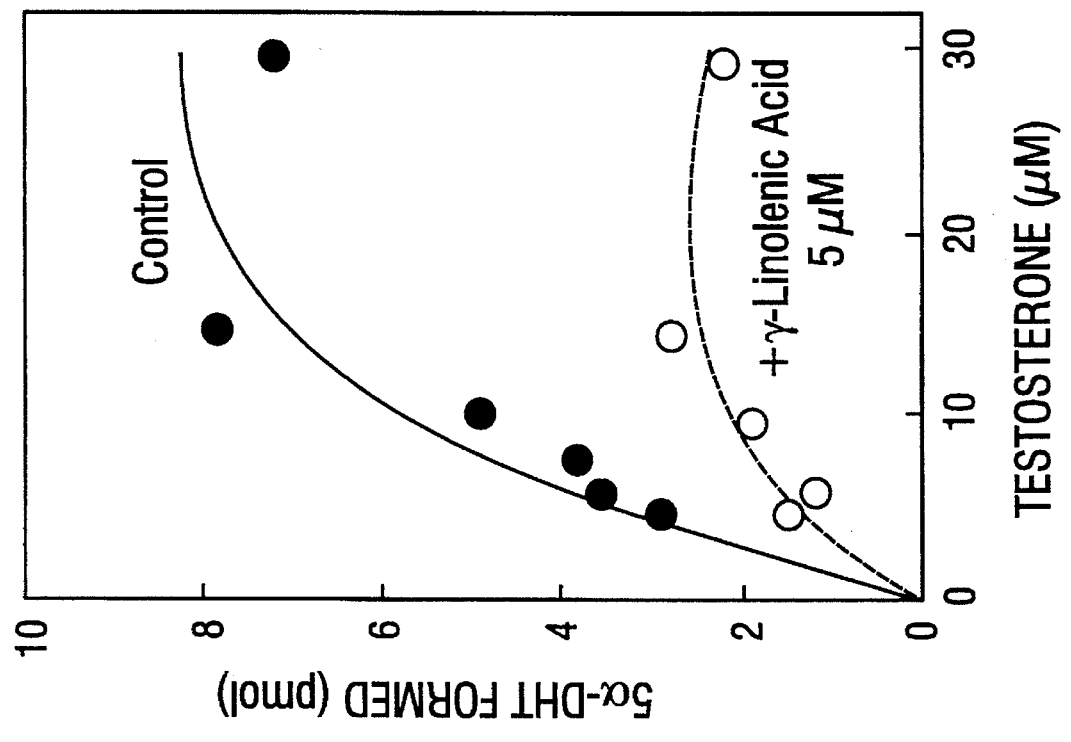
FIG. 16B. Inhibition of 5α-reductase activity by γ-linolenic acid at varying concentrations of testosterone. The concentrations of γ-linolenic acid are shown.
Figure 16A:
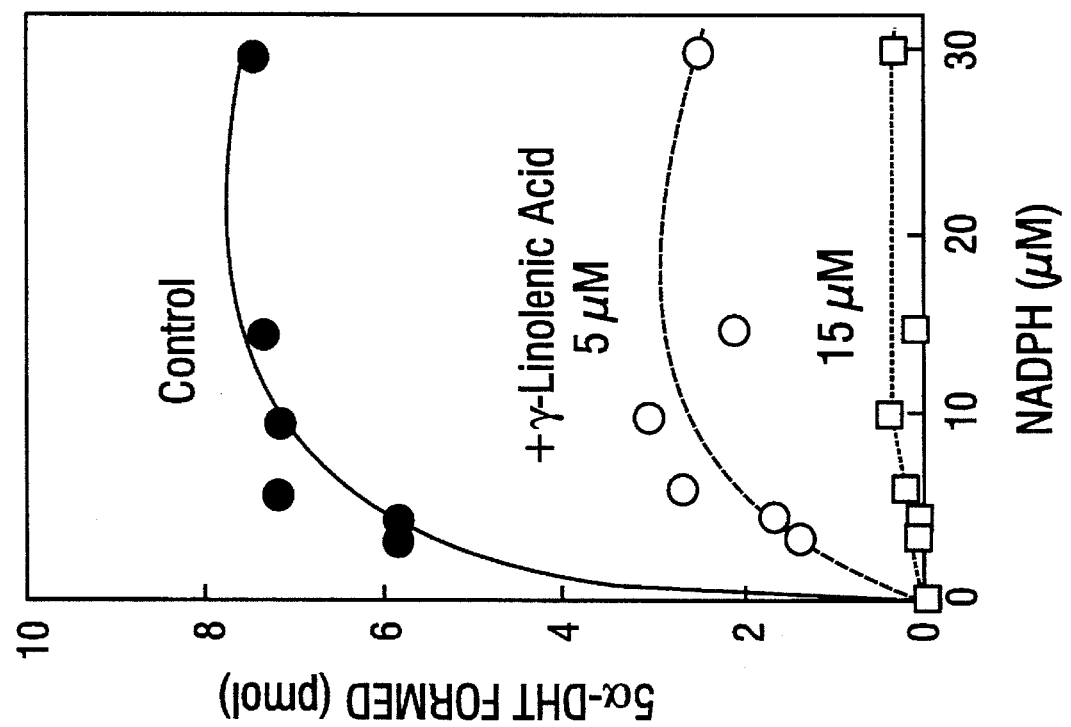
FIG. 16A. Inhibition of 5α-reductase activity by γ-linolenic acid at varying concentrations of NADPH. The concentrations of γ-linolenic acid are shown.
Figure 17:
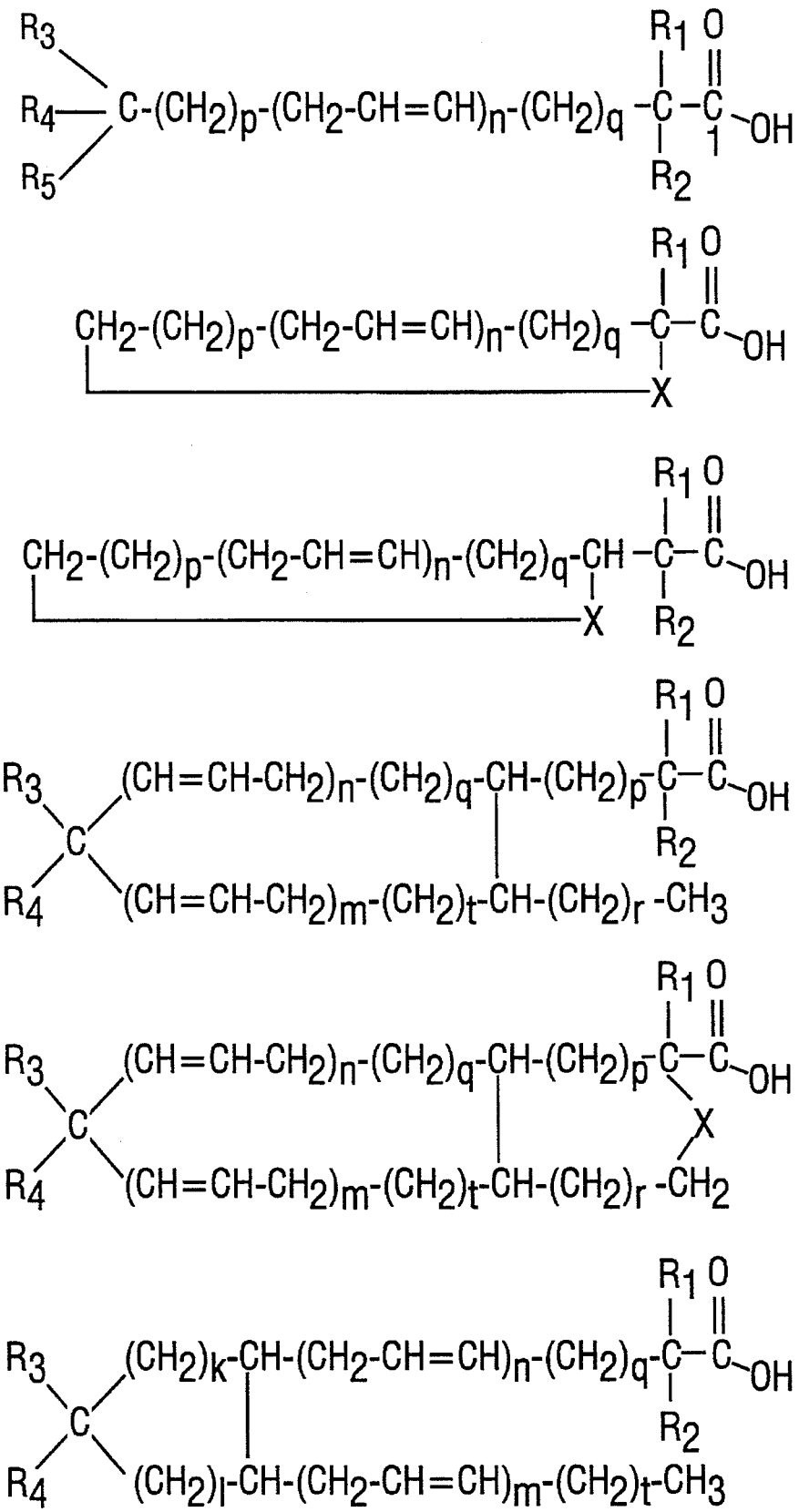
FIG. 17. General formula for compounds that are part of the present disclosure. $R_1$, $R_2$, $R_3$, $R_4$, $R_5$, $R_6$, $R_7$, $R_8$, or $R_9$ may be a hydrogen, a fluorine or other halogen, or a methyl, ethyl, propyl, other alkyl or aryl group; one or two fluorine or other halogen atom(s) may replace hydrogen attached to any carbon atom(s) and 'l', 'm', 'n', 'p', 'q', 'r', and 't' are each independently 0 or an integer from 1 to about 50 and, preferably from 1 to about 30. The alkyl or aryl group and fluorine or other halogens attached to the molecules may protect them from degradation by oxidation of the unsaturated double bonds and $\alpha$, $\beta$ or $\omega$ oxidation. Oxidation products and metabolites of these fatty acids are also included since they are also expected to regulate 5α-reductase activity. Also —CH and the —OH groups can be in a substituted form (—CR and/or —OR) wherein —R represents an alkyl or an aryl group. Also included are acylates and esters that, upon hydrolysis, can form the carboxylic acid shown. 'X' can be a carbon, a sulfur, an oxygen, or a —NH—. This X-linkage is not limited to link carbon 2 and the carbon at the end of the chain; the link can be between any two carbons in the carbon chain. For protection of a fatty acid from oxidative degradation, it may be useful to incorporate one or two sulfur atoms into the backbone carbon chains. The total carbon chain length can be 6 to 28.
Figure 19:
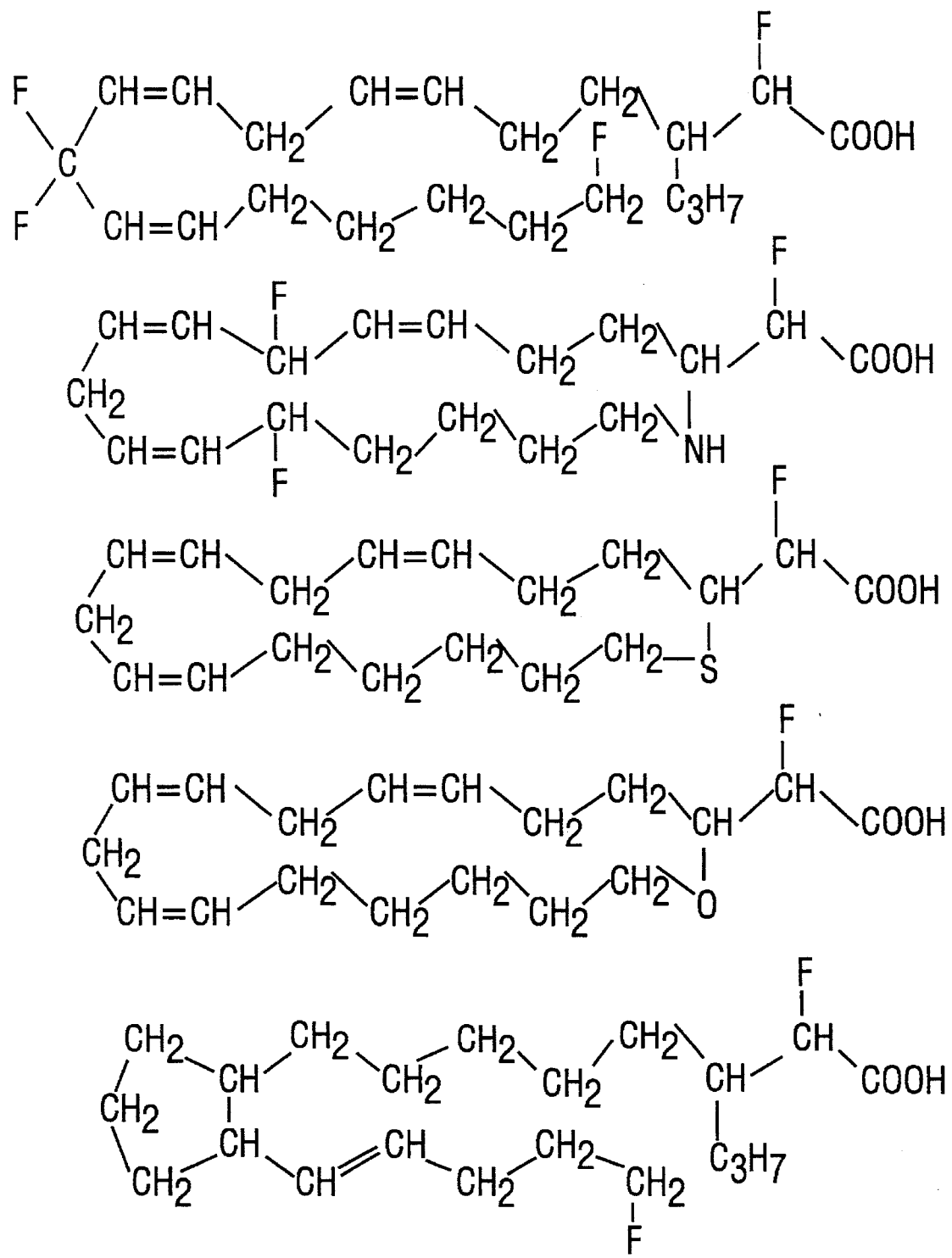
FIG. 19. Examples of fluorinated and cyclic derivatives of fatty acids that are part of the present disclosure.

By either the enzymatic or the [$^3$H]4-MA binding assay, the inhibition could not be overcome by increasing the level of NADPH (FIG. 16A) or testosterone (FIG. 16B). γ-LA did not appear to compete with testosterone or NADPH for their binding to the microsomal reductase. Double reciprocal plots of the data showed that 5 μM of γ-LA increased the apparent $K_m$ value for NADPH (from 2.0 to 3.1 μM) and testosterone (from 2.4 to 4.5 μM), and decreased the $V_{max}$ from 7.5 to 2.8 pmol 5α-DHT formed/mg protein/15 min. γ-LA at 5 and 10 μM increased the apparent $K_i$ values for [$^3$H]4-MA from 13 to 20 and 40 μM, respectively, and decreased the maximal binding from 0.56 to 0.45 and 0.40 pmol/10 μg protein, respectively.

2. NADH:Menadione Reductase and UDP-Glucuronic Acid:5α-DHT Glucuronyl Transferase Inhibition The effect of γ-LA on the activities of another microsomal reductase and a microsomal enzyme that uses asteroid as a substrate was tested to determine the specificity of the effect of γ-LA. Results showed that γ-LA at 10 to 40 μM did not affect the activities of NADH:menadione reductase or UDP-glucuronic acid:5α-DHT glucuronosyl transferase.

Mammalian 5α-reductase is a cellular membrane-bound enzyme. Perturbation of the lipid matrix of the membranes may affect reductase activity nonspecifically. The fact that only unsaturated fatty acids with specific configurations were potent inhibitors of 5α-reductase in a specific assay and that two other microsomal enzymes examined were not affected suggests that the inhibition was selective.

3. Effect of γ-LA on Human Microsomes and Prostate Cancer Cells

γ-LA inhibited NADPH-dependent [$^3$H]4-MA binding to human liver microsomes to the same degree as in experiments with rat liver microsomes. The 5α-reduction of [$^3$H] testosterone by human prostate cancer cells in culture was also selectively affected by γ-LA. Table 3 shows that γ-LA, at 5 to 50 μM, inhibited 5α-reductase reduction of [$^3$H] testosterone in both the androgen-sensitive LNCaP cells (Horszewicz et al., 1983) and the androgen insensitive PC-3 cells (Kaighn et al., 1979). γ-LA, however, did not affect the metabolism of testosterone to 4-androstenedione, suggesting that 17β-steroid dehydrogenase was not sensitive to the unsaturated fatty acid. Stearic acid (5 to 20 μM) did not affect the 5α-reductase reduction or 17β-steroid dehydrogenase of PC-3 cells in culture. The specific 5α-reductase inhibition observed with intact prostate cells in culture indicated that externally added fatty acids were able to enter cells and exert an inhibitory action on the endoplasmic reticulum or nuclear membrane-bound 5α-reductase in situ.

TABLE 3

Inhibition of the Formation of Radioactive 4-Androstenedione and 5α-DHT from [$^3$H]Testosterone by Human Prestatic Cancer Cells by γ-LA

| Prostate cell line | Fatty acid added (μM) | Metabolites formed* | |
|---|---|---|---|
| | | 4-Androstendione (% of control) | 5α-DHT (% of control) |
| PC-3 | None (control) | 100 | 100 |
| | γ-LA 1 | 102 ± 6 | 98 ± 6 |

TABLE 3-continued

Inhibition of the Formation of Radioactive 4-Androstenedione and 5α-DHT from [³H]Testosterone by Human Prostatic Cancer Cells by γ-LA

| Prostate cell line | Fatty acid added (μM) | Metabolites formed* | |
|---|---|---|---|
| | | 4-Androstendione (% of control) | 5α-DHT (% of control) |
| | 5 | 110 ± 1 | 50 ± 3 |
| | 20 | 99 ± 2 | 2 ± 2 |
| | Stearic acid | | |
| | 5 | 103 ± 2 | 123 ± 2 |
| | 20 | 106 ± 5 | 121 ± 5 |
| LNCaP | None (control) | ND | 100 |
| | γ-LA | | |
| | 50 | ND | 27 ± 0 |
| | 100 | ND | 9 ± 4 |

*The control values for the formation of 4-androstenedione and 5α-DHT by PC-3 cells were 400,851 ± 9,507 dpm and 12,183 ± 74 dpm, respectively. The control value for the formation of 5α-DHT by LNCaP was 4,569 ± 505 dpm. No 4-androstenedione formation was detected when LNCaP was used. γ-LA and stearic acid, at the concentrations tested, did not produce any visible change in cell morphology during the 2 hour incubation. $IC_{50}$ values (four studies) for γ-LA with the prostate cancer cells were 10 ± 5 μM.

EXAMPLE 5

Effects of Polyunsaturated Fatty Acids and Other Compounds on Androgen Action in the Hamster Flank Organ Model The inventors sought an inhibitor of 5α-reductase that would be active topically and inactive systemically, as such an agent would be ideal for treatment of androgen-dependent dermatological disorders. Of the aliphatic unsaturated fatty acids tested for inhibition of 5α-reductase activity in liver and prostate from rats and humans, γ-LA was found to be the most potent fatty acid inhibitor when topically applied to hamster flank organs.

In this study, inhibition of androgen action by topical administration of γ-LA in hamster flank organs is investigated. Especially useful in the evaluation of the effects of these compounds on skin cells or sebaceous glands is the hamster flank organ (Frost and Gomez, 1972). The paired flank organs, one on each side of the costovertebral angle, are highly sensitive to androgen stimulation. The androgen sensitive structures in the flank organ include dermal melanocytes, sebaceous glands, and hair follicles (Hamilton and Montagna, 1950). This animal model has been widely used for testing androgenic (Hamilton and Montagna, 1950; Frost et al., 1973) and antiandrogenic compounds (Voigt and Hsia, 1973; Weissmann et al., 1985; Chakrabarty et at., 1980). The unique advantage of this animal model is that a testing compound can be applied topically to only one of the flank organs and the effect observed on both organs. If the test compound has only a local effect then only the treated flank organ is affected. However, if the effect is systemic then both flank organs are affected. Results indicate that γ-LA applied topically inhibits androgen action locally without a systemic effect.

A. MATERIALS AND METHODS

1. Chemicals

Fatty acids were obtained from Sigma Chemical Co., St. Louis, Mo. Testosterone (T) and 5α-DHT were purchased from Steraloid, Wilton, N.H.

2. Treatment of Castrated Animals

Pre-pubertal male Syrian golden hamsters, castrated at 4 weeks old, were obtained from Harlan Sprague-Dawley Co. (Madison, Wisc.). Each animal was maintained individually in a plastic cage on rodent chow (Purina) and water ad libitum on a 12 h light/12 h dark cycle.

One to two weeks after castration, the hair on the lower back of each animal was clipped with an electric hair clipper and then shaved weekly to expose the flank organs. The animals were divided into 5 animals/treatment group. A treatment solution (5 μl) was applied topically to the right flank organ once a day using a Pipetteman and a polypropylene disposable tip. Unless specified the left flank organ was not treated. The treatment solution contained either (a) ethanol alone (vehicle and control), (b) an androgen (T or 5α-DHT), (c) a fatty acid, or (d) a combination of an androgen and a fatty acid. The flank organ was wiped with an alcohol pad to remove residual compound before each treatment. At the end of each experiment (17–25 days), the animals were sacrificed by either suffocation with $CO_2$ gas or with an intraperitoneal injection of an overdose of phenobarbital (64.8 mg/ml/animal). The flank organs, both the treated and untreated sides, were evaluated with methods to be described below to determine the effect of these treatments of the growth of the pigmented macules and the sebaceous glands. The body weight of each animal was recorded before and after treatment.

3. Treatment of Intact Animals

Intact male hamsters, 4 weeks old, were kept on a longer light period (16 h light/8 h dark cycle) to insure maximum stimulation of sexual characteristics (Luderschmidt et al., 1984). Animals were divided into 10/group. The right flank organ was treated daily with 5 μl solution containing vehicle (ethanol) alone or γ-LA (0.5, 1, and 2 mg) for 15–25 days. The left flank organ of all animals received the same volume of vehicle.

4. Determination of the Area of the Pigmented Macule of the Flank Organs

The lengths of the long axis and the short axis of the pigmented spot (pigmented macule) were measured using a caliper with digital display (Digimatic, Mitutoyo Corp., Japan). The product (long axis×short axis, $mm^2$) was used as an index of the surface area (Wuest and Lucky, 1989). The data are presented as mean ± standard deviation.

5. Determination of the Sebaceous Gland Elevation

The flank organ treated with T ± fatty acid became elevated and palpable. The length of the long axis and short axis of the elevated mass were measured with a caliper. The product of the long axis×short axis ($mm^2$) was used as an index of the areas of the sebaceous gland, which correlated with the volume of the sebaceous glands (Weissmann et al., 1984). The data are presented as mean ± standard deviation. The sebaceous glands of the flank organs, which were not treated with T, were not elevated and were not measured.

6. Treatment Solution

Thin layer chromatographic examinations (Whatman LK5DF silica plate using a solvent system consisting of chloroform:methanol, 3:1) of a γ-LA solution in ethanol revealed two additional more polar products, indicating oxidation of γ-LA, after 5 weeks of storage. Therefore special precautions were taken to avoid changes in treatment compounds. To avoid oxidation, all treatment compounds (T, 5α-DHT, fatty acid) were dissolved in ethanol, placed in a vial wrapped with aluminum foil to shield light, and stored at 4° C. The air in the vials were displaced with nitrogen gas by placing one or two drops of liquid nitrogen into each vial before being capped. Nitrogen was replaced each time the vials were opened. Thin layer chromatographic examination of a γ-LA solution refrigerated for 3 weeks revealed no detectable changes of the compound. All treatment solutions were prepared once a week as an additional precaution to avoid changes in the treatment solutions.

7. Statistics

Student's t-test was used to statistically analyze the data. A two sided p value <0.05 was considered statistically significant.

B. RESULTS

Figure 26:
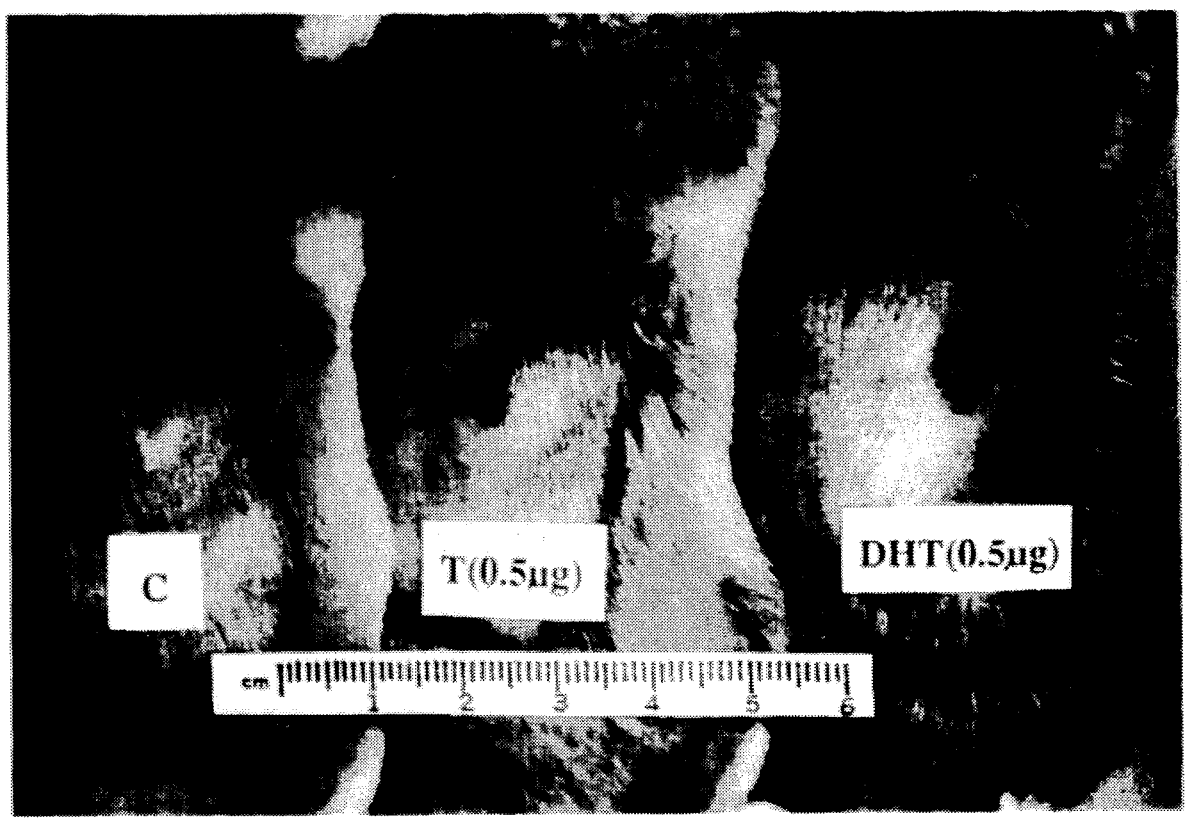
FIG. 26. Stimulation of hamster flank organ by topical application of testosterone (T) and dihydrotestosterone (5α-DHT). The right flank organs of immature castrated male hamsters (5 each group) were treated topically with 5 μl/day of ethanol solution alone (C), or ethanol containing 0.5 μg T or 5α-DHT for 17 days. One representative animal from each group is shown.
Figure 27:
FIG. 27. Effect of testosterone (T) stimulation on the application site (right flank organ) versus the contralateral site (left flank organ). The right flank organ of immature castrated male hamsters was treated with T (0.5 μg/day) for 17 days. The left flank organ was not treated.
Figure 28:
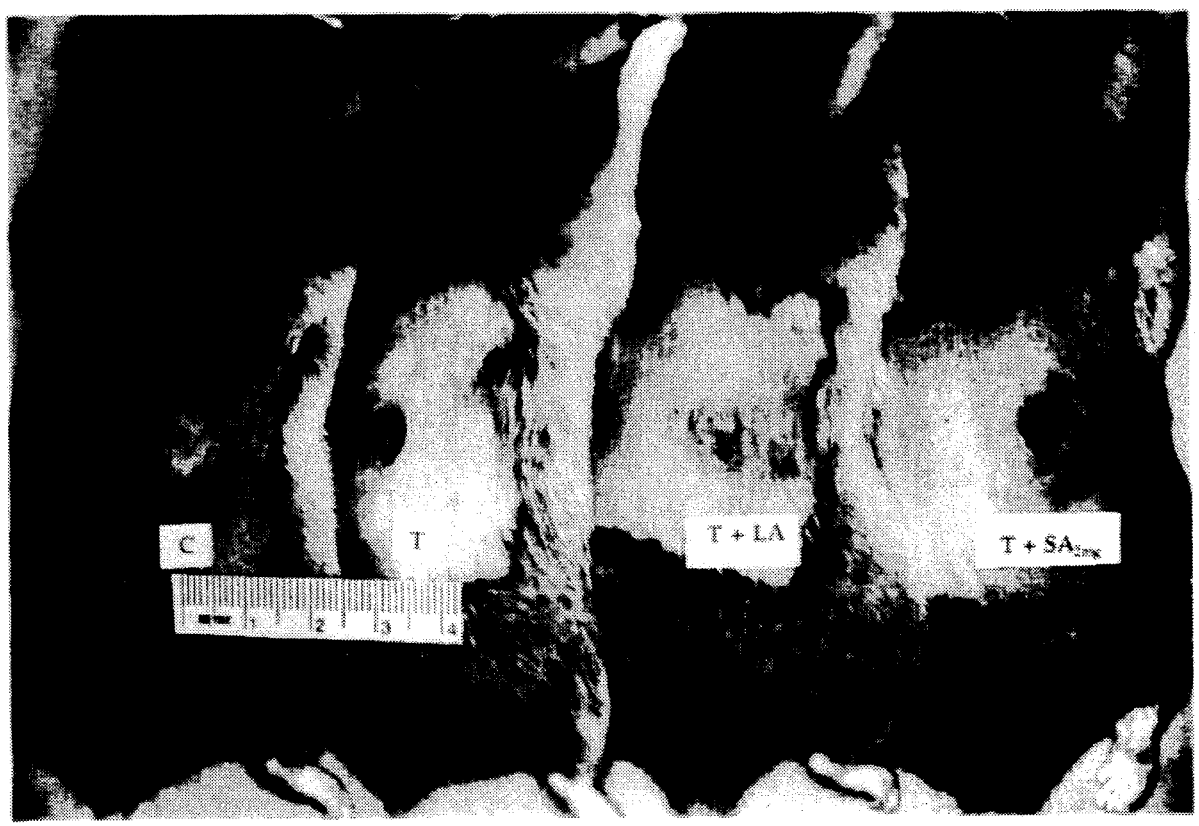
FIG. 28. Inhibition of testosterone-stimulated growth of the pigmented macule of the hamster flank organ by γ-linolenic acid, but not by stearic acid. Male hamsters (4 weeks old) were castrated and treatment was started 2 weeks later for 18 days. The animals were treated with 5 μl of ethanol (C), ethanol containing testosterone (T, 0.5 μg), T (0.5 μg)+γ-linolenic acid (LA, 1 mg), T (0.5 μg)+stearic acid (SA, 1 mg), or T (0.5 μg)+SA (2 mg). Only the right flank organ was treated and shown here. The data collected from these animals are shown in Table 7.

When one of the paired pigmented macules of a prepubertal castrated male hamster was treated with either T or 5α-DHT, it became much darker in color and larger in area compared to pigmented macules treated with vehicle alone. FIG. 26 shows examples from each group of animals. Application of T or 5α-DHT to the right flank organ produced no detectable effect on the contralateral flank organ of the same animal, indicating that the effect of T and 5α-DHT stimulation is local. FIG. 27 shows one of the animals from the T treated group. T was tested at 0.5, 2, and 5 µg/flank organ/day, 5 animals/group, and the control group received vehicle alone. After 24 days of treatment, the index of the area of the pigmented macule was 2.4±1.4 mm$^2$ for the control group, 45.6±8.0 mm$^2$ for 0.5 µg T, 69.4±13.7 mm$^2$ for 2 µg T, and 66.4±4.2 mm$^2$ for 5 µg T. There were no significant differences in the body weight among different treatment groups before and after treatment. A submaximal dose of T (0.5 µg/flank organ/day) was chosen for the following experiments.

γ-LA and SA were tested for their ability to inhibit the growth of the pigmented macule stimulated by T. γ-LA is the most potent fatty acid in vitro and SA was inactive as an inhibitor of 5α-reductase tested in vitro (Liang and Liao, 1992). The results are shown in FIG. 28 and Table 4.

TABLE 4

THE EFFECT OF γ-LA AND STEARIC ACID ON TESTOSTERONE-STIMULATED GROWTH OF THE PIGMENTED MACULE OF THE HAMSTER FLANK ORGAN

| Treatment | Pigmented Macule (mm$^2$) | |
| --- | --- | --- |
| | Untreated (L) | Treated (R) |
| Control (5 µl ethanol) | 5.1 ± 1.9 | 4.2 ± 0.5 |
| γ-LA (1 mg) | 4.2 ± 0.6 | 4.1 ± 0.3 |
| Stearic Acid (SA) (1 mg) | 4.4 ± 0.4 | 4.9 ± 0.9 |
| SA (2 mg) | 4.6 ± 1.4 | 5.0 ± 0.8 |
| T (0.5 µg/ 5 µl ethanol) | 3.6 ± 0.5 | 32.7 ± 9.2 |
| T + γ-LA (1 mg) | 4.1 ± 0.3 | 15.3 ± 3.9 (−53%, p < 0.005)* |
| T + SA (1 mg) | 4.3 ± 0.6 | 27.7 ± 4.4 (N.S.)+ |
| T + SA (2 mg) | 4.2 ± 0.4 | 30.1 ± 7.1 (N.S.)+ |

Each experimental group had 5 castrated immature hamsters. The right flank organs (R) were treated every day with 5 µl ethanol or 5 µl ethanol containing testosterone (T), γ-linolenic acid (γ-LA), stearic acid (SA), T + γ-LA, or T + SA at the doses indicated for 18 days. The left flank organs (L) were not treated.
*T vs. T + γ-LA
+N.S. = not significant; T vs. T + SA T treatment stimulated the growth of the pigmented macule, this effect of T was inhibited by γ-LA. This is indicated by the pigmented macules being lighter in color and smaller in area for animals treated with both γ-LA (1 mg/flank organ/day) and T (0.5 µg/flank organ/day) than those of animals treated with T alone. The pigmented area was reduced by 53% (32.7±9.2 vs. 15.3±3.9 mm$^2$, p<0.005).

In contrast, SA (1 mg and 2 mg) applied with T did not inhibit the ability of T to stimulate the growth of the pigmented macule. There were no significant differences in the pigmented macules among the control group and those treated with either γ-LA or SA alone. The body weights and contralateral flank organs were uniformly not affected. Structurally, both γ-LA and SA are aliphatic fatty acids with a chain length of 18 carbons. They are different in that γ-LA (C18:3,cis-6,9,12) has three cis-double bonds at 6, 9 and 12 positions (counting carboxyl terminal carbon as 1), and that SA (C18:0) is a saturated fatty acid without double bonds.

To further study the structural specificity of the active fatty acids, the ability of various fatty acids to inhibit T-induced growth of the pigmented macules of the flank organs was determined. Table 5 shows that γ-LA (66% inhibition) was more active than all other fatty acids tested for their ability to inhibit T-induced growth of the pigmented macule. α-LA (C18:3,cis-9,12,15) was less active than γ-LA (C18:3,cis-6,9,12), indicating that the positions of the double bonds are important for the inhibitory activity.

Oleic acid (C18:1,cis-9) and linoleic acid (C18:2,cis-9,12) were active, whereas their transisomers, elaidic acid (C18:1, trans-9) and linolelaidic acid (C18:2,trans-9,12) were inactive suggesting that fatty acids with a cis double bond configuration are more active than those with a trans configuration. Weak inhibitions were found with palmitic acid (C16:0), arachidonic acid (C20:4,cis-5,8,11,14), and erucic acid (C22:1,cis-13). There was no significant inhibition by undecylenic acid (C11:1,10) or nervonic acid (C24:1,cis-15). Fatty acid specificities in vivo are, in general, similar to their ability to inhibit the 5α-reductase activity in vitro (Liang and Liao, 1992). In the absence of T, none of the fatty acids tested stimulated or inhibited the growth of the pigmented macules.

To investigate whether inhibition of 5α-reductase is the primary mode of action of γ-LA, the ability of γ-LA to inhibit T and 5α-DHT-induced growth of the hamster flank organ was compared γ-LA was tested at dosages from 0.01 to 2 mg/flank organ/day for their ability to inhibit the growth of the pigmented macule stimulated by T (0.5 µg/flank organ/day). γ-LA was found to be effective at a dosage of 0.2 mg or higher and a maximal inhibition (50%) was reached by 1 mg. γ-LA (0.2 to 1 mg/flank organ/day) was tested for its ability to inhibit T and DHT induced growth of the pigmented macule and the results are shown in Table 6. These results indicate that T-induced growth of the pigmented macule was preferentially inhibited by γ-LA. There is no statistically significant inhibition of 5α-DHT-induced growth by γ-LA although the average values were reduced by higher dosages of γ-LA.

TABLE 5

EFFECTS OF SELECTED FATTY ACIDS ON TESTOSTERONE-STIMULATED GROWTH OF THE PIGMENTED MACULE

| Fatty Acid | Pigmented macule | | Percent Inhibition | p |
| --- | --- | --- | --- | --- |
| | Left (mm$^2$) | Right (+T) (mm$^2$) | | |
| None | 4.8 ± 1.1 | 49.6 ± 8.3 | — | — |
| Undecylenic acid (C11:1,10) | 4.7 ± 1.2 | 41.7 ± 10.7 | — | N.S.* |
| Palmitic acid (C16:0) | 5.1 ± 2.9 | 37.2 ± 6.3 | 25% | <0.05 |
| Oleic acid (C18:1,cis-9) | 4.7 ± 0.5 | 28.1 ± 8.3 | 43% | <0.005 |
| Elaidic acid | 4.9 ± 1.1 | 47.0 ± 5.9 | — | N.S. |

TABLE 5-continued

EFFECTS OF SELECTED FATTY ACIDS ON
TESTOSTERONE-STIMULATED GROWTH OF THE
PIGMENTED MACULE

| Fatty Acid | Pigmented macule | | | |
|---|---|---|---|---|
| | Left (mm$^2$) | Right (+T) (mm$^2$) | Percent Inhibition | p |
| (C18:1,trans-9) Linolenic acid (C18:2,cis-9-12) | 5.4 ± 1.6 | 23.9 ± 5.0 | 52% | <0.001 |
| Linolelaidic acid (C18:2,trans-9,12) | 4.1 ± 0.7 | 46.6 ± 8.7 | — | N.S. |
| α-Linolenic acid (C18:3,cis-9,12,15) | 4.1 ± 1.2 | 27.6 ± 8.2 | 44% | <0.005 |
| γ-Linolenic acid (C18:3,cis-6,9,12) | 4.4 ± 1.6 | 17.0 ± 6.4 | 66% | <0.001 |
| Arachidonic acid (C20:4,cis-5,8,11,14) | 4.7 ± 1.6 | 35.7 ± 7.9 | 28% | <0.05 |
| Erucic acid (C22:1,cis-13) | 4.6 ± 1.5 | 35.4 ± 4.6 | 29% | <0.02 |
| Nervonic acid (C24:1,cis-15) | 4.0 ± 1.5 | 39.9 ± 5.4 | — | N.S. |

*N.S. = not significant
The right flank organ was treated topically with 5 μl solution containing either testosterone (0.5 μg) or testosterone plus a fatty acid (1 mg). The left flank organ received same solution as the right flank organ except that testosterone was omitted. The treatments were once a day for 21 days. Five animals per treatment group.

TABLE 6

DIFFERENTIAL EFFECT OF γ-LA ON TESTOSTERONE-
AND 5α-DHT-INDUCED GROWTH OF PIGMENTED
MACULES AND SEBACEOUS GLANDS OF FLANK ORGANS

| Treatment | Pigment Macule (mm$^2$) | P | Sebaceous Gland (mm$^2$) | P |
|---|---|---|---|---|
| T$_{0.5\mu g}$ | 32.9 ± 2.6 | — | 45.8 ± 4.1 | — |
| T + γ-LA$_{0.2mg}$ | 22.7 ± 4.3 (−31%) | <0.005 | 32.2 ± 6.0 (−30%) | <0.005 |
| T + γ-LA$_{0.4mg}$ | 24.9 ± 5.8 (−24%) | <0.02 | 32.2 ± 17.2 | N.S. |
| T + γ-LA$_{0.6mg}$ | 18.0 ± 3.4 (−45%) | <0.001 | 22.6 ± 3.0 (−51%) | <0.001 |
| T + γ-LA$_{0.8mg}$ | 22.3 ± 2.3 (−32%) | <0.001 | 34.5 ± 8.4 (−25%) | <0.005 |
| T + γ-LA$_{1.0mg}$ | 21.6 ± 2.3 (−34%) | <0.001 | 20.4 ± 3.0 (−55%) | <0.001 |
| DHT$_{0.5\mu g}$ | 33.7 ± 8.6 | — | 30.3 ± 4.5 | — |
| DHT + γ-LA$_{0.2mg}$ | 32.1 ± 3.1 | N.S. | 39.5 ± 6.9 | N.S. |
| DHT + γ-LA$_{0.4mg}$ | 28.9 ± 3.2 | N.S. | 35.8 ± 13.1 | N.S. |
| DHT + γ-LA$_{0.6mg}$ | 27.0 ± 3.9 | N.S. | 39.7 ± 10.7 | N.S. |
| DHT + γ-LA$_{0.8mg}$ | 24.9 ± 5.3 | N.S. | 30:3 ± 12.9 | N.S. |
| DHT + γ-LA$_{1.0mg}$ | 24.7 ± 3.0 | N.S. | 33.3 ± 11.9 | N.S. |

The right flank organs of castrated immature male hamsters were treated topically with a 5 μl solution ethanol containing testosterone (T) or 5α-dihydrotestosterone (5α-DHT) alone or a combination of T and γ-linolenic acid (γ-LA) or 5α-DHT and γ-LA. The treatment was once a day for 19 days. The data shown are for the right (treated) flank organ. The left organ was not treated. The amount of androgens and γ-LA used each day are indicated.

Table 6 also shows differential effects of γ-LA on the T- and 5α-DHT-induced growth of the sebaceous glands, recognizable as palpable mass, in the flank organs. The sebaceous glands are directly underneath the pigmented macule, but extend beyond the pigmented area after T treatment. γ-LA also inhibited T-induced growth of the sebaceous glands, but it did not significantly affect the growth of the sebaceous glands stimulated by 5α-DHT treatment.

Figure 29:
FIG. 29. γ-Linolenic acid applied to the right flank organ of intact male hamster produced a localized inhibition of the growth of the pigmented macule stimulated by endogenous androgens. The right flank organs of intact male hamsters, 4 weeks old, were treated for 156 days as described in Table 7. The treatment consisted of topical solutions of vehicle (ethanol) alone (C) or γ-LA (1 mg/flank organ/day). The fight flank organs of 2 representative hamsters are shown.
Figure 30:
FIG. 30. γ-Linolenic acid topically applied to the right flank organ of intact hamsters inhibited only the application site and not the contralateral (left) flank organ. A representative intact hamster treated with 1 mg γ-LA from group 3 of the study described in Table 7 is shown.

It was determined whether γ-LA could inhibit the growth of the pigmented macule stimulated by endogenous androgens as intact male hamsters developed from a sexually immature to mature status. The right flank organs were treated daily with vehicle alone or γ-LA (0.5 and 1 mg). The left flank organs of animals in all three groups received vehicle alone. At the beginning of treatment, the pigmented macules of all groups were small, approximately 4 mm$^2$. After 15 days of stimulation by endogenous androgens, the pigmented macules of the control group grew 6-fold, with no difference between the right and left side. γ-LA treatment significantly inhibited the growth of the pigmented macule (Table 7). FIG. 29 shows one of these specimens. The inhibition by γ-LA treatment was local since the growth of the contralateral pigmented macules was not affected (FIG. 30 and Table 4). γ-LA treatment also inhibited hair growth of the treated flank organ.

Figure 31:
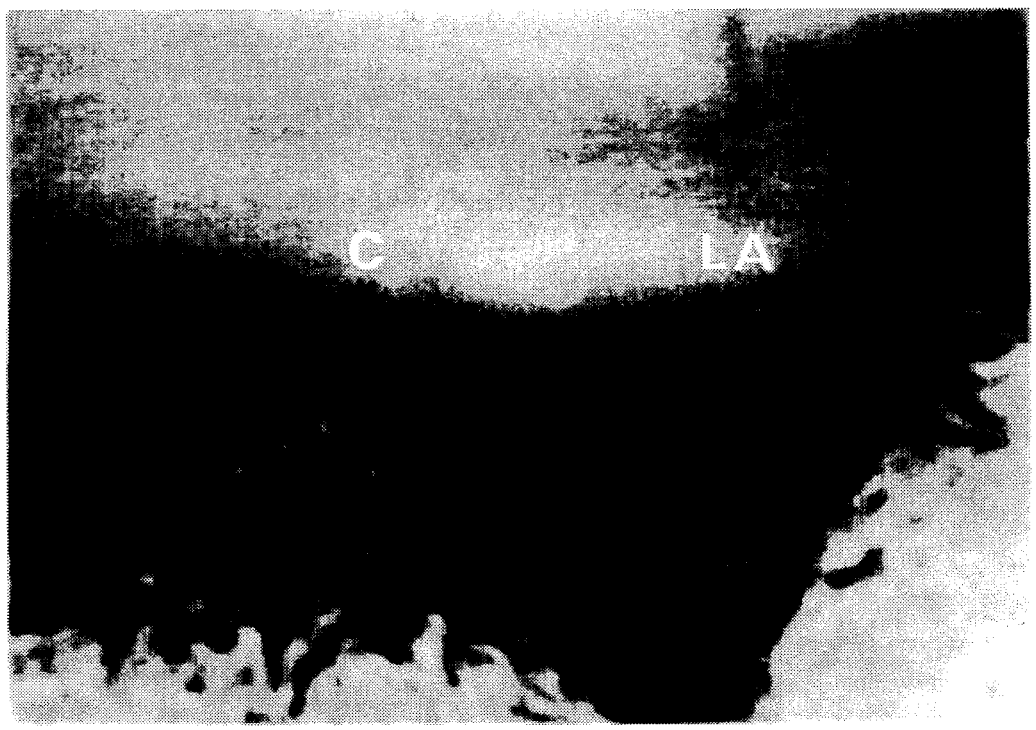
FIG. 31. γ-Linolenic acid reduced the pigmentation and the length of the hair in the flank organ. The hamsters shown here are the same animals shown in Table 7. The picture represents the hair growth on the flank organ during the last two days. The hair of the flank organ of the group treated with 1 mg γ-LA/5 μl ethanol/day (A) was markedly lighter in color and shorter in length than the vehicle (C) treated hamsters.
Figure 32:
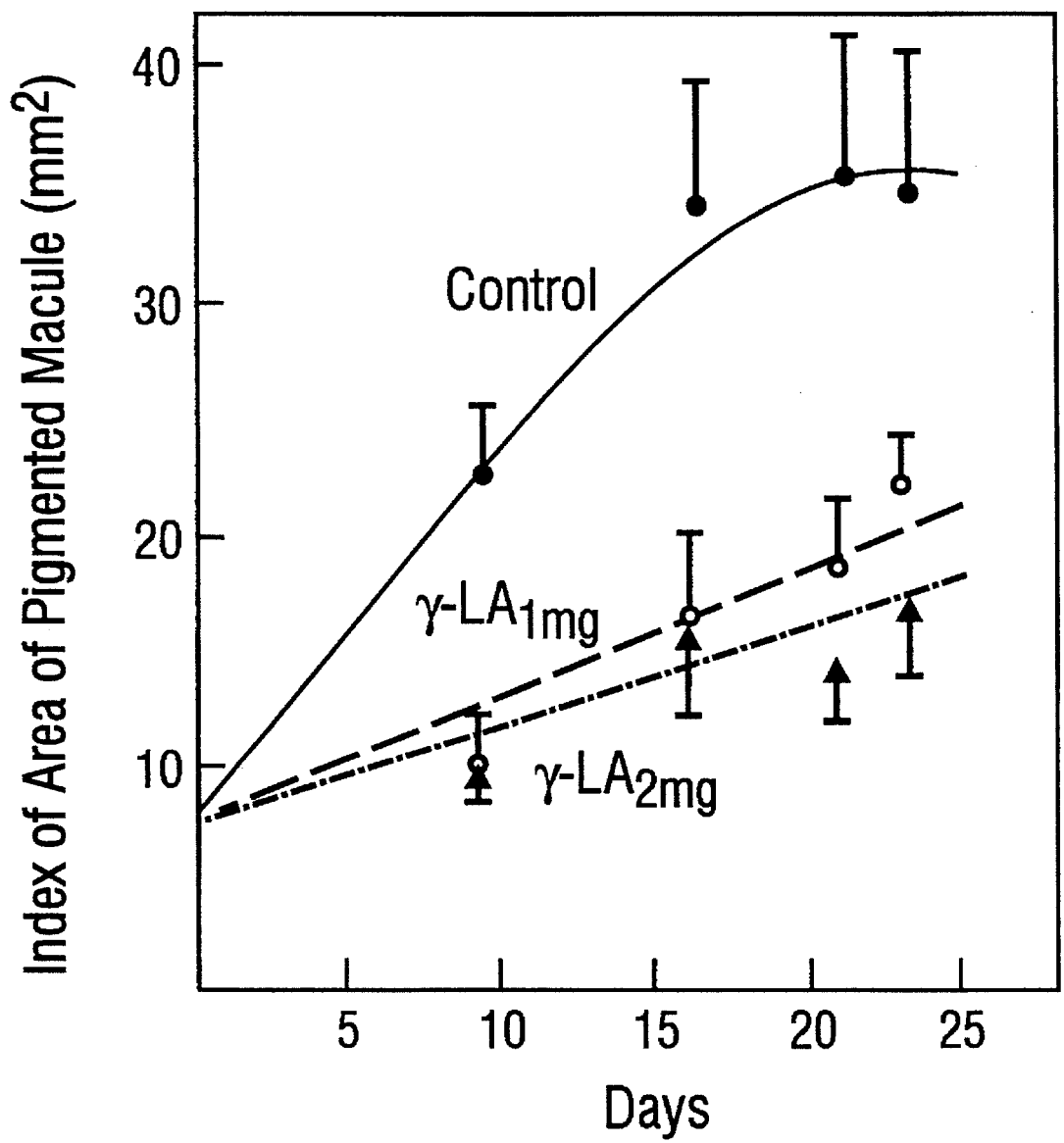
FIG. 32. The effect of γ-linolenic acid treatment on the growth rate of the pigmented macules from intact male hamsters. The right flank organs of intact prepubertal male hamsters, 4 weeks old, were treated topically with vehicle alone (control), γ-LA 1 mg or 2 mg/5 μl ethanol/flank organ/day. Them were 10 animals per treatment group. The index of the area of the pigmented macules was determined at the beginning (Day 0) and after various days of treatment. The left flank organs received vehicle only. The growth rates of the pigmented macules of the left flank organs of all 3 groups were similar to that of the right flank organ of the control group.

FIG. 31 shows the representative examples which indicate that the hair in the γ-LA treated flank organ was lighter in color and shorter in length than those of the control. In another study, the right flank organs of intact immature male hamsters received daily treatment with vehicle alone (control), 1 mg γ-LA, and 2 mg γ-LA. The areas of the pigmented macules were calculated from periodic measurement to demonstrate the inhibition of the growth rate of the pigmented macule by γ-LA treatment. FIG. 32 shows that the pigmented macules of the control animals grew linearly until day 16, but this growth was dramatically reduced by γ-LA treatment. The growth rates of the pigmented macules of the left flank organs were similar among all three groups, indicating that the inhibitory effect of γ-LA treatment was local.

TABLE 7

INHIBITION OF GROWTH OF THE PIGMENTED
MACULE IN INTACT MALE HAMSTERS BY γ-LA

| Animal | Left flank organ | | Right flank organ | |
|---|---|---|---|---|
| | Treatment | Pigmented macule (mm$^2$) | Treatment | Pigmented macule (mm$^2$) |
| Group 1 | vehicle | 24.7 ± 2.1 | vehicle | 23.5 ± 3.8 (N.S.)# |
| Group 2 | vehicle | 28.6 ± 4.0 (N.S.)* | γ-LA$_{0.5mg}$ | 19.0 ± 3.6 (−34%, p < 0.001)# (−19%, p < 0.0252)* |

TABLE 7-continued

INHIBITION OF GROWTH OF THE PIGMENTED
MACULE IN INTACT MALE HAMSTERS BY γ-LA

| Animal | Left flank organ | | Right flank organ | |
|---|---|---|---|---|
| | Treatment | Pigmented macule (mm$^2$) | Treatment | Pigmented macule (mm$^2$) |
| Group 3 | vehicle | 29.2 ± 4.8 (N.S.)* | γ-LA$_{1.0mg}$ | 10.8 ± 2.7 (−63%, p < 0.001)# (−54%, p < 0.001)* |

The right flank organs of intact male hamsters at 4 weeks of age were treated with a topical solution containing either 5 μl ethanol or 5 μl ethanol containing 0.5 or 1.0 mg γ-LA every day for 15 days. The left flank organ of all groups received ethanol only. There were 10 animals/group. The results of the γ-LA treated groups were compared either with that of group 1 or with the left flank organ of the same group.

C. DISCUSSION

Topical applications of certain unsaturated fatty acids such as γ-LA can inhibit androgen action in the hamster flank organ. Several lines of evidence suggest that inhibition of 5α-reductase may be the primary mode of action for γ-LA. First, in the cell-free systems, γ-LA is a potent inhibitor of 5α-reductase in liver or prostate from humans and rats (Liang and Liao, 1992). Second, in castrated hamsters γ-LA inhibits the growth of the pigmented macule induced by T, but not that induced by 5α-DHT. Third, the structural requirements for fatty acids to inhibit T-induced growth of the pigmented macules and to inhibit 5α-reductase are very similar. In addition to its ability to inhibit T-induced growth of the pigmented macule, γ-LA also inhibits T-induced growth of other structures of the flank organ e.g., the sebaceous glands and hair. This suggests that γ-LA acts on 5α-reductase, which is a common step in androgen action in all three structures. This demonstrates specific effect of unsaturated fatty acids on androgen action in vivo.

Topically applied γ-LA did not completely abolish the growth of the pigmented macule in castrated hamsters treated topically with T. The maximum inhibition (50 to 66%) was reached with the daily dose of 1 to 2 mg γ-LA. Several factors may contribute to this incomplete inhibition. First, the penetration of γ-LA may be a limiting factor. Second, T can affect androgen action by binding to androgen receptors, although with lower receptor binding affinity than that of 5α-DHT (Liao et al., 1973).

γ-LA, an essential fatty acid (Horrobin, 1992), and the active unsaturated fatty acids shown in this study are normal components in human tissue, e.g., skin (Schafer and Kragballe, 1991). Therefore, they should be safe to use in humans. Since γ-LA applied topically produced a localized effect without systemic action, γ-LA and its analogues are desirable for topical application and treatment of androgen-dependent skin conditions such as acne, androgenetic alopecia, female hirsutism, sebaceous hyperplasia, and seborrhea.

EXAMPLE 6

Effects of γ-Linolenic Acid Injection to Hamsters on the Growth of Various Organs 1. γ-LA Inhibits Growth of Flank Organs Before treatments, the areas of pigmented spots of flank organs were similar between the two groups. The right flank organ was 5.9±1.2 mm$^2$ for the control group and was 6.6±2.0 for the γ-LA group. The left flank organ was 6.2±1.4 for the control group and was 6.2±2.1 for the γ-LA group. γ-LA injections inhibited the growth of the flank organ, both the right and the left.

Thus, the right flank organ was 14.6±1.5 mm$^2$ for the control group and was 9.8±2.5 for the γ-LA group (p<0.001). The left flank organ was 12.9±2.2 for the control group and was 9.9±2.4 for the γ-LA group (p<0.02).

2. γ-LA Inhibits Growth of Seminal Vesicles and Prostate

These two tissues were weighed together because the prostates were hard to separate from the seminal vesicles. The seminal vesicles and prostates were 0.156±0.026 g for the control group and were 0.106±0.022 for the γ-LA group (p<0.001).

3. γ-LA Does Not Inhibit Growth of Kidneys, Adrenal or Spleen

The weights for each of these organs were: kidney (1.060±0.086 g for the control group vs. 1.121±0.073 for γ-LA group), adrenal (0.022±0.004 g for control vs. 0.021±0.004 for γ-LA), or spleen (0.157±0.027 for control vs. 0.1867±0.048 for γ-LA). None of the differences between the control and γ-LA groups are statistically significant.

γ-LA given to hamsters by subcutaneous injections inhibited the growth of androgen-dependent tissues: the flank organs, seminal vesicles and prostates. γ-LA treatments did not affect the kidney, adrenal, or spleen. These tissues are known not requiring androgen to grow. Thus, γ-LA administered subcutaneously can inhibit androgen actions.

EXAMPLE 7

Topical Effects of Polyunsaturated Fatty Acids and Other Compounds on Hair Loss and Growth The stamptail macaque monkey develops baldness in a pattern resembling human androgenetic alopecia. The balding process begins shortly after puberty (approximately 4 years of age). This occurs in nearly 100% of the animals, males and females, and is androgen dependent. This is a useful animal model for human androgenetic alopecia and is contemplated to be useful in demonstrating the effects of polyunsaturated fatty acids on hair loss. The following describes a protocol for testing (Rittmaster et at., 1987; Diani et al. 1992)

Male stamptailed macaques (4 years of age) are divided into groups of 3 to 5 animals. A defined area of the scalp involving the frontal and vertex areas is marked, e.g., by tattoo. Hairs in the marked area are shaved. The solutions of a testing compound in different dosages and combinations are evenly applied to the shaved areas once or twice a day. Control animals receive the same volume of the solvent (e.g., ethanol or other organic solvent, or a cream). The same area of the scalp is shaved every 4 to 6 weeks and the weights of hairs shaved are determined. The treatments may last for 6 months to 2 years. 4-MA (17-N,N-diethylcarbamoyl-4-methyl-4-aza-5-androstan-3-one), a 5α-reductase inhibitor known to prevent baldness in this animal is included as a positive control. Biopsies of the scalp (4 mm punch) are obtained before and at the end of the treatments. The specimens are analyzed for 5α-reductase activity and examined histologically for evidence of alopecia.

EXAMPLE 8

Effects of Catechins and Their Derivatives on 5α-Reductase Activity

By enzymatic assay, tea catechin gallates are potent inhibitors of the type 1 but not type 2 5α-reductase. The IC$_{50}$ for (−)Epigallocatechin-3-gallate and (−)epicatechin-3-gallate for the type 1 human 5α-reductase are about 10 µM. (−)Epicatechin and (−)epigallocatechin are not active for either types of the enzyme. Unlike 4-azasteroids and many other nonsteroidal inhibitors, these gallates do not contain heterocyclic nitrogen rings and do not compete with testosterone or NADPH for binding to 5α-reductase.

A. MATERIALS AND METHODS

1. Materials

Various biochemicals and polyphenolic compounds were obtained from Sigma Chemical Co. (4-$^{14}$C)-testosterone (60 mCi/mmol) was a products of New England Nuclear. (1,2-$^3$H) 17β-N,N-diethylcarbamoyl-4-methyl-4-aza-5α-androstan-3-one ([$^3$H]4-MA) (60 Ci/mmol) was prepared as previously described (Liang et al., 1983). Purified catechins were obtained from Funakoshi Co. (Tokyo, Japan) or from Sigma Chemical Co. The purity of individual catechins was at least 98% pure based on the NMR and HPLC analyses. Various catechins were also purified in the inventor's laboratory from green tea (*Camellia sinensis*) as described below.

2. Isolation and Purification of Catechins from Green Tea

Dried green tea (50 g) was extracted twice with 500 ml of 90° C. $H_2O$ for 15–30 min. The combined water extract was freeze dried. The dried powder was dissolved in 50 ml of water and extracted with an equal volume of $CHCl_3$. catechins in the aqueous layer were extracted twice with ethyl acetate. After removal of ethyl acetate, the dried powder (1 g) was dissolved in 10 ml of 95% ethanol and loaded onto a Sephadex LH-20 column (5×35 cm). The column was eluted with 95% ethanol and the effluent was monitored by UV absorption at 280 nm. The identity and purity of isolated catechins (FIG. 21) were assessed by NMR spectrum analyses and HPLC. HPLC was performed by using a C18 reversed phase column (4.6 mm×250 mm, 5µ, Alltech Co.) isocratically with acetonitrile/ethyl acetate/0.05% $H_3PO_4$ in water (12:2:86) as the mobile phase.

3. Preparation of Rat 1A Cells Expressing Human 5α-Reductases

The cDNAs for the human type 1 and 2 5α-reductases were isolated from human prostate λZAP II™ cDNA libraries using the published sequence of the 5α-reductases, PCR™ and standard library screening techniques (Sambrook et al., 1989). The type 1 and 2 cDNAs correspond to nucleotides 31–870 and 28–829, respectively, of the published sequences for these 5α-reductases (Anderson and Russell, 1990; Anderson et al., 1991). The type 1 and 2 cDNAs were subcloned into the retroviral expression vector pMV7 (Kirschmeier et al., 1988) and high titer stocks of virus containing the type 1 and 2 cDNAs were generated using the packaging cells BOSC 23 293 (Kirschmeier et al., 1988). Rat.-1A cells (Pear et al., 1993) were infected with virus (Topp, 1981) and cells containing integrated retrovirus were selected for G418-$SO_4$ resistance, (Brown and Scott, 1987).

4. [$^3$H]4-MA Binding and Enzymatic Assays for Microsomal 5α-Reductase

Microsomes were prepared as described previously (Liang and Liao, 1992) from the liver of adult Sprague-Dawley female rats or Rat-1A cells expressing a specific type of human 5α-reductase. Each study was carried out in duplicate or triplicate which were usually within 10% of each other. Several studies were preformed to assure that the results shown are representative. The data presented was based on the rate of reaction. The compounds showing less than 10% inhibition were considered not active (NA) at the indicated concentrations.

[$^3$H]4-MA binding assay were described in detail previously (Liang and Liao, 1992; Liang et al., 1983). The assay solution, in a final volume of 0.15 ml, contained 0.08 µCi of [$^3$H]4-MA, 0.1 mM NADPH, 0.1 mM dithiothritol and 50 mM potassium phosphate, pH 7.0, with or without a test compound. The reaction was started by the addition of 25 µl of microsomes (25 µg protein). After 30–60 min incubation at 0° C., the [$^3$H]4-MA bound to microsomes was collected on a Whatman GF/F glass fiber, washed and radioactivity determined (Liang and Liao, 1992).

The enzymatic assay was based on the measurement of 5α-DHT production from testosterone in the presence of microsomes (Liang and Liao, 1992; Liang et al., 1983). The assay mixture, in the final volume of 0.25 ml, contained 2.8 µM 4-[$^{14}$C] testosterone, 0.1 mM NADPH, 1 mM dithiothreitol, and 100 mM potassium phosphate, pH 6.0, with or without a test compound. The reaction was started by the addition of 25 µl of microsomes (25 µg protein). The mixture was incubated at 37° for 30–60 min and stopped by addition of 0.5 ml of ethyl acetate and mixing for 1 min. The organic solvent extract was removed under vacuum. The cried extract was dissolved in 25 µl of ethyl acetate and applied to a silica gel 60 TLC plate which was developed in a solvent system consisting of methylene chloride:ethyl acetate:methanol (85:15:3). conversion of testosterone to a 5α-reduced metabolites was measured by scanning the TLC plate on an AMBIS radioanalytical scanner. 5α-DHT was the predominant metabolite (>95%) with little or no conversion of testosterone to androstanediols, androstandione, 4-androstenedione or thermetabolites.

B. RESULTS AND DISCUSSION

Most of the 5α-reductase activity is lost during the solubilization and purification of 5α-reductase from microsomal or nuclear membranes. The 5α-reductase activity, therefore, has been characterized by measuring the rate of conversion of testosterone to 5α-DHT by whole cells or by microsomal preparations in the presence of NADPH. The 5α-reductase activity of rat liver which contains only the type 1 5α-reductase (Russell and Wilson, 1994; Normington and Russell, 1992) can also be reliably assayed by following NADPH-dependent noncovalent binding of a potent radioactive inhibitor, such as [$^3$H]4-MA, which strongly competes with testosterone for binding to the reductase (Liang et al., 1983).

Based on the [$^3$H]4-MA binding assay (Table 8) or enzymatic assay EGCG, ECG and CG but not (+)catechin, (±)catechin, (−)gallocatechin, (−)epicatechin, or (−)epigallocatechin are potent inhibitors of the type 1 5α-reductase of rat liver microsomes. The $IC_{50}$ for EGCG, ECG, and CG were 3 µM, 12 µM and 18 µM, respectively. Since the presence of the gallate moiety in the catechin molecule appeared to be important for the inhibitory activity, a number of compounds having the gallate structure were tested. Gallic acid and a number of alkyl gallates were not active even at 200 µM. Several compounds having a gallolyl (3,4,5-trihydroxy benzene) group were also not inhibitory (Table 8).

TABLE 8

INHIBITION OF [³H]4-MA BINDING TO 5α-REDUCTASE OF RAT LIVER MICROSOMES BY TEA CATECHINS AND RELATED COMPOUNDS

| Test Compounds | % Inhibition of [³H]4-MA binding Concentration of test compounds (μM) | | | | |
|---|---|---|---|---|---|
| | 5 | 10 | 20 | 40 | 200 |
| (+)Catechin | NA | NA | NA | NA | NA |
| (±)Catechin | NA | NA | NA | NA | NA |
| (−)Gallocatechin | NA | NA | NA | NA | NA |
| (−)Epicatechin | NA | NA | NA | NA | NA |
| (−)Epigallocatechin | NA | NA | NA | NA | NA |
| (−)Catechin-3-gallate | 12 | 31 | 53 | 73 | 91 |
| (−)Epicatechin-3-gallate | 25 | 44 | 74 | 88 | 92 |
| (−)Epigallocatechin-3-gallate | 61 | 74 | 79 | 88 | 93 |

No inhibitory activity was found with the above compounds having gallolyl (3,4,5-trihydroxybenzene) or gallate groups at concentrations up to 200 μM: pyrogallol, 3,4,5-trimethoxy benzoic acid, 3,4,5-trimethoxy phenylacetic acid, 3,4,5-trihydroxy-benzamide, 3-[3,4,5-trimethoxyphenyl] propionic acid, gallic acid, methyl gallate, n-propyl gallate, isopropyl gallate, n-octylgallate, and n-dodecyl gallate. Among other compounds having a similar structure but are inactive are: quercetin, α-naphthaflavone, β-naphthaflavone, rutin, 4[4-chlorophenylmethyl]-6,7-dimethoxy-isoquinoline methanesulfonate. Caffeine, a major compound in the tea extract was also not active at concentrations up to 200 μM.
NA: not active.

By the [³H]4-MA assay (Table 9) or the enzymic assay (Table 10), (−)epicatechin, and (−)epigallocatechin were not active inhibitors for either type 1 or 2 human microsomal 5α-reductase that were genetically engineered and expressed in Rat-1A cells. By the [³H]4-MA binding assay (Table 9), ECG and EGCG, were active inhibitors of both isozymes but exhibited some preferential inhibition of the type 1 isozyme at concentrations below 30 μM. However, by the enzymic assay (Table 10), ECG and EGCG, at concentrations below 30 μM, did not inhibit the Type 2 isozyme but were potent inhibitors for the Type 1 isozyme. The $IC_{50}$ values for the two gallates were about 10 μM. As expected, finasteride which has been shown to selectively inhibit type 2 human isozyme (2) inhibited the type 2 isozyme expressed in Rat-1A cells. In comparison, γ-LA inhibited both types of human isozymes, either based on the [³H]4-MA binding assay (Table 9) or by the enzymic assay (Table 10).

TABLE 9

INHIBITION OF [³H]4-MA BINDING TO HUMAN 5α-REDUCTASE ISOZYMES BY VARIOUS COMPOUNDS

| Test compound | Isozyme type | % Inhibition of [³H]4-MA binding Concentration of test compound (μM) | | | | |
|---|---|---|---|---|---|---|
| | | 1 | 3 | 10 | 30 | 100 |
| (−)Epicatechin | 1 | NA | 13 | NA | NA | 18 |
| (−)Epicatechin | 2 | NA | NA | NA | NA | NA |
| (−)Epigallocatechin | 1 | NA | NA | NA | NA | 23 |
| (−)Epigallocatechin | 2 | NA | NA | NA | 13 | 14 |
| (−)Epicatechin-3-gallate | 1 | 34 | 47 | 79 | 87 | 79 |
| (−)Epicatechin-3-gallate | 2 | 17 | 17 | 45 | 76 | 80 |
| (−)Epigallocatechin-3-gallate | 1 | 29 | 47 | 77 | 88 | 86 |
| (−)Epigallocatechin-3-gallate | 2 | NA | 12 | 55 | 72 | 89 |
| γ-Linolenic acid | 1 | 20 | 54 | 65 | 79 | 85 |
| γ-Linolenic acid | 2 | 22 | 49 | 63 | 72 | 88 |
| Finasteride# | 1 | NA | NA | NA | NA | NA |
| Finasteride# | 2 | NA | NA | 22 | 44 | 67 |

Concentration in nM

With the enzymatic assay or the [³H]4-MA binding assay, ECG and EGCG inhibited the rate and extent of the reaction by type 1 isozyme of the rat liver or Rat-1 cells. These gallates did not appear to compete with testosterone or NADPH for their binding to microsomal 5α-reductase since the inhibition could not be overcome by increasing the concentration of NADPH or testosterone. These gallates did not induce NADPH oxidation during the incubation of the reaction mixtures in the presence of microsomes.

Most of the known 5α-reductase inhibitors are steroid derivatives (Russell and Wilson, 1994; Faller et al., 1993). Finasteride, is a therapeutic agent for treatment of benign prostate hyperplasia (BPH) (McConnel et al., 1992). 4-MA and finasteride are 4-azasteroids that are effective in preventing male pattern baldness in experimental animals (Rittmaster et al., 1987; Rittmaster, 1994). LY191704, a selective inhibitor of the type 1 5α-reductase, shares the structural feature of 4-azasteroids but lacks the fourth ring of a steroid (Hirsch et al., 1994). ONO-3805 (Russell and Wilson, 1994) is one of several benzoylaminophenoxybutanoic acid derivatives that posses the 5α-reductase inhibitory activity. 4-azasteroids, LY191704, and ONO-3805 contain amino groups that may play a role in their interaction with 5α-reductase. In contrast, unsaturated fatty acids may act by perturbation of the lipid matrix of the membranes and, therefore, are not selective inhibitors of 5α-reductase isozymes (Russell and Wilson, 1994). The isozyme-dependent effect of tea gallates suggests that the galloyl group can interact with a specific group in the type 1 5α-reductase. Since many alkyl gallates were not active (Table 8), other structural features in the epicatechin molecules may be also important for inhibition.

It has been was shown that γ-LA can inhibit the conversion of testosterone to 5α-DHT by human prostate cancer (PC3 and LNCaP) cells in culture; EGCG also reduced 5α-DHT production by these cells in culture. EGCG administered to male rats also was able to reduce the weight of ventral and dorsolateral prostates, coagulating glands, seminal vesicles, and preputial glands without affecting the weight of testis or kidney.

Some catechins have been shown to inhibit enzymatic activity in vitro. The most sensitive enzyme reported was HIV-1 reverse transcriptase ($IC_{50}$ for EGCG: 40 nM) (Nakane et al., 1994). However, this inhibition is apparently non-specific (Moore & Pizza, 1992). Soybean lipoxygenase is also inhibited by EGCG ($IC_{50}$:10 μM), ECG ($IC_{50}$:18 μM), and EGC ($IC_{50}$:21 μM). α-Amylase of human saliva, rat small intestinal sucrase and maltase are less sensitive to EGCG inhibition ($IC_{50}$:50–500 μM) (Honda et al., 1994).

Various tea catechin gallates and related compounds have anticarcinogenic activity against cancer of the esophagus, skin, colon and other organs (Yang and Wang, 1993). ECG and EGC account for about 65% of solid matter in the hot water extract of green tea. Their concentrations in green tea beverage are about 5–10 mM.

TABLE 10

INHIBITION OF 4-[$^{14}$C]TESTOSTERONE REDUCTION BY HUMAN 5α-REDUCTASE ISOZYMES BY VARIOUS COMPOUNDS

| Test compound | Isozyme type | % Inhibition of 5α-reduction Concentration of test compound (μM) | | | | |
|---|---|---|---|---|---|---|
| | | 1 | 3 | 10 | 30 | 100 |
| (−)Epicatechin | 1 | NA | 13 | NA | NA | 14 |
| (−)Epicatechin | 2 | NA | NA | NA | NA | NA |
| (−)Epigallocatechin | 1 | NA | NA | NA | NA | 15 |
| (−)Epigallocatechin | 2 | NA | NA | NA | NA | MA |
| (−)Epicatechin-3-gallate | 1 | 20 | 27 | 47 | 90 | 99 |
| (−)Epicatechin-3-gallate | 2 | NA | NA | NA | NA | 82 |
| (−)Epigallocatechin-3-gallate | 1 | 22 | 23 | 34 | 89 | 98 |
| (−)Epigallocatechin-3-gallate | 2 | NA | NA | NA | NA | 73 |
| γ-Linolenic acid | 1 | 31 | 52 | 89 | 99 | 99 |
| γ-Linolenic acid | 2 | 30 | 48 | 60 | 88 | 99 |

EXAMPLE 9

Effects of Fatty Acids and Catechins on Sebum Production in a Human Model

Topical antiandrogenic activity of several fatty acid and catechin was first evaluated in the hamster flank organ assay or the rat assay. To further confirm the effectiveness of antiandrogenic compounds and suitability for human use, tests were performed on a human male subject. The ideal compounds for human treatment are those that are topically and locally active but do not show systemic antiandrogenic activity, especially in the cases involving young males. In the following example, two classes of compounds were tested by measuring sebum secretion from the forehead of an adult male treated topically.

A. METHODS

1. Determination of Forehead Sebum Production

A 63-year old Asian male volunteer was used to test and analyze sebum production from the forehead region. The forehead was washed thoroughly by soap twice and cleaned by 70% isopropyl alcohol twice. Sebum production was measured 30 to 60 minutes later by a sebum meter (Courage/Khazaka Electronic GmbH, Germany). The sebum meter tape probe (7 mm×8 mm) covered 56 mm$^2$ area in each measurement. Ten measurements were made within the 4 cm square area (16 cm$^2$) located at the middle of the left or right side forehead between the eyebrow and the hair line.

The sebum meter detected the difference in the transparency of the tape before and after the tape was placed on the forehead for 30 seconds and expressed the difference in an arbitrary number (S-value) between 0 to 300 (or higher). S-values of sebum accumulated on the foreheads of men are usually 200 to 300. Skin surface on hands usually showed a very low number (5 to 20). The S-value for forehead immediately after washing was less than 5. For men, the S-value gradually increased to about 50 within 30 minutes after washing and reached 100 to 200 in 45 minutes to 55 minutes.

To determine the rate of sebum production, the left and the right forehead areas were measured alternatively and each time at the comparable areas on the two sides. Ten measurements on each side (i.e., 20 measurements for two sides) could take about 15–20 minutes and the sebum-values ranged between 30 to 200. The S-values were different considerably at different areas of the forehead and could be influenced by environmental, including weather, diet, and physiological conditions. However, the ratio of the total S-value (the sum of 10 measurements) for the left and the total S-value for the right forehead was constant. For the Asian male tested in this experiment, the L/R ratios measured over a six month's period was within 1.15 to 1.38 if the S-values were determined 30 to 50 minutes after the forehead was washed thoroughly. Therefore, compounds applied to the left forehead that reduced the L/R ratio to lower than 1.1 were considered as topically active agents for suppression of sebum production.

B. RESULTS

1. γ-LA Inhibition of Human Forehead Sebum

Figure 24:
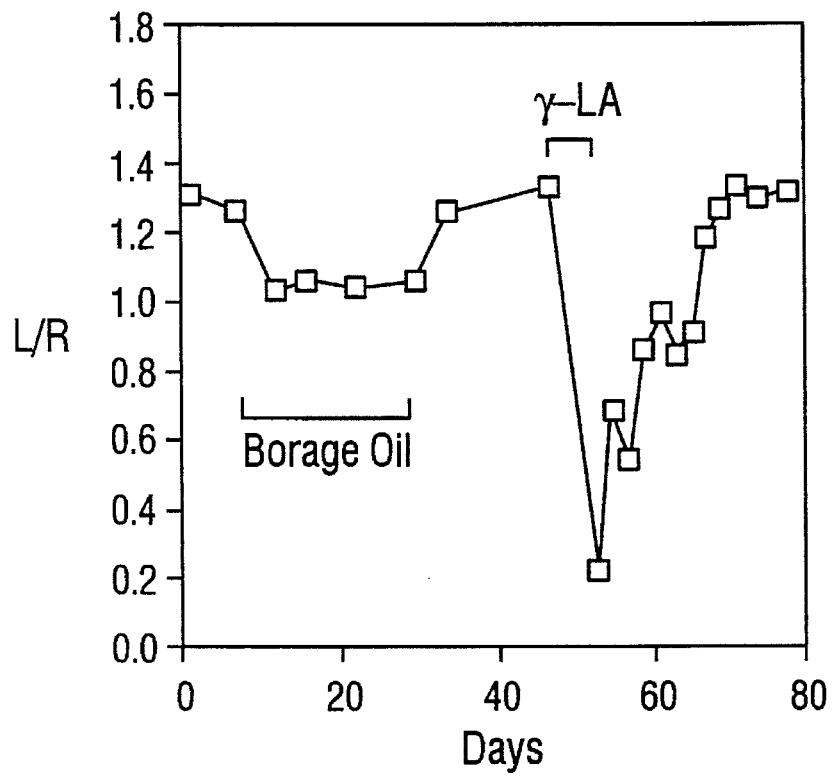
FIG. 24. γ-Linolenic acid inhibition of forehead sebum production in a human male.

In the experiment shown in FIG. 24, 0.2 ml of borage oil (containing 18% of γLA) in a gel capsule was applied to the left forehead twice daily for 23 days. During this period, L/R ratio reduced from 1.28±0.03 down to 1.05±0.01. After the borage oil treatment was stopped, the L/R ratio returned to 1.20±0.14. The effect of borage oil on the sebum production on the left forehead was relatively small, possibly due to the fact that most γLA in the borage oil was in the form of triglyceride that did not inhibit 5α-reductase (see Table 2). Free acid released from the glyceride by nonenzymic or enzymic action was probably responsible for the effect.

After the borage oil application was stopped and the L/R ratio recovered to 1.33, 20 mg of pure γ-LA was applied to the left forehead twice each day for 6 days. The L/R ratio decreased to 0.22 during this period. After the γ-LA application was stopped, the L/R ratio recovered slowly to 1.20±0.14 over the period of 16 days. The finding clearly showed that γ-LA was superior than borage oil in quickly suppressing sebum production from forehead of a human male subject.

2. Catechin Inhibition of Human Forehead Sebum Production

Figure 25:
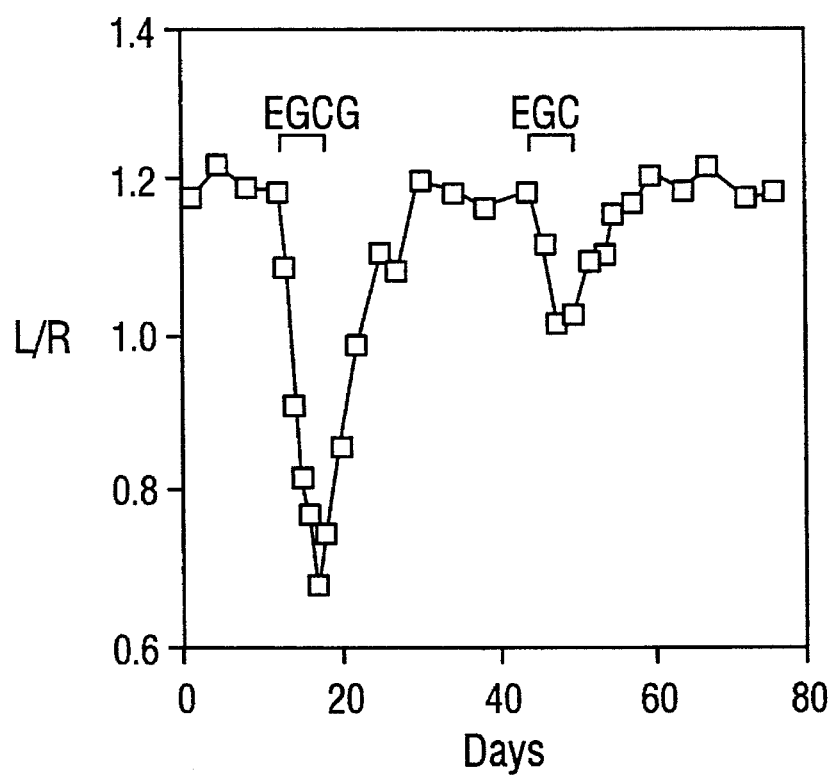
FIG. 25. Catechin inhibition of forehead sebum production in a human male.

Twenty mg of (−)epigallocatechin gallate (EGCG) in 0.2 ml 70% ethanol was applied to the left forehead twice a day for 6 days (FIG. 25). The L/R ratio decrease from 1.20±0.02 to 0.71±0.04 during this period. After the EGCG treatment was stopped, the L/R ratio gradually recovered to 1.19±0.02 within 16 days. Subsequent treatment of the left forehead with 20 mg (−)epicatechin in 0.2 ml 70% ethanol twice a day for 6 days reduced the L/R ratio to 1.02±0.1. After the application was stopped, the L/R ratio gradually increased to the normal value of 1.21±0.01 in 10 days. Clearly EGCG was more effective in reducing the sebum production from forehead than (−)epicatechin.

EXAMPLE 10

Effects of Catechins on Body Weight and Androgen-Dependent Organs in Rats

Male Sprague-Dawley rats (body weight 180 g±10 g) were used. Each group had 5 rats. EGCG (15 mg/0.1 ml 30% ethanol/rat/day) was intraperitoneally injected into rats in one group each day for 7 days. Rats in the control group received 0.1 ml 30% ethanol. The results of this study is presented in Table 11.

1. Effects of γ-LA and Catechins on Body Weight and Growth of Prostate and Preputial Organ in Small Rats Male Sprague-Dawley rats, 60±5 g body weight, were used. Each group had 6 rats, and all were castrated. On the day of castration, and thereafter, (−)epicatechin (EC), (−)epigallocatechin gallate (EGCG), or γ-LA (5 mg each in 0.1 ml of 30% ethanol containing 10 μg testosterone) was injected intraperitoneally every day for 14 days. The control rats received 0.1 ml of 30% ethanol containing 10 μg testosterone daily.

TABLE 11

EFFECT OF EPIGALLOCATECHIN GALLATE ON BODY WEIGHT AND MALE ACCESSORY REPRODUCTIVE ORGANS, AND PREPUTIAL ORGANS OF RATS

|  | Control | EGCG[a] | % of Control Final[b] | Increase[c] |
| --- | --- | --- | --- | --- |
| Final body weight (g) | 238.2 ± 10.6 | 191.8 ± 12.0 | 80.5 | 20.3 |
| Ventral prostate (mg) | 201.9 ± 36.2 | 142.2 ± 10.7 | 70.4 | 62.0 |
| Seminal Vesicle (mg) | 234.3 ± 11.7 | 164.9 ± 30.4 | 70.4 | 52.3 |
| Coagulating gland (mg) | 78.0 ± 5.9 | 45.5 ± 11.7 | 58.3 | 39.8 |
| Preputial gland (mg) | 126.8 ± 24.8 | 76.1 ± 33.1 | 60.0 | (−)28.2[d] |

[a]15 mg/day.
[b]Based on the full weight.
[c]Based on the increase in the weight.
[d]Reduced from the control weight.

The results showed that γ-LA and EGCG but not EC reduced the weights of ventral prostate and preputial organ by about 10 to 35%. EGCG but not EC or γ-LA reduced the body weight increase by about 35%. It appears that γ-LA and EGCG will be useful in reducing the prostate size where as EGCG may be useful in the control of body weight increase. Rats injected with EGCG or γ-LA appeared to be as healthy as rats in other groups. When various organs were examined by eyes, there was no obvious infection, necrosis or changes in the color or the size of organs such as adrenal, spleen, liver, kidney, thymus, pancreas, etc. Fat content under the skin appeared less in the rats injected with EGCG. EGCG effect on the prostate weight or body weight increase may be specific, at least in part, due to the modulation of androgen-dependent growth of prostate, muscle growth or cellular fat production.

2. Catechins Affect Body Weight and Growth of Prostate and Preputial Organ in Large Rats Male Sprague Dawley rats, 172±20 g body weight, were used. Each group had 5 rats. EC, EGC, ECG, or EGCG, (15 mg each in 0.3 ml of 30% ethanol) was injected intraperitoneally every day for 7 days. The control rats received 0.3 ml of 30% ethanol.

The results showed that while the normal rats gained body weight, during the 7 days of experiment, from 172±20 g to 232±10 g (about 35% increase), the body weight of rats receiving EGCG decreased to an average of 147±14 g (about 15% decrease). Thus, rats in the EGCG group were about 36% smaller than the normal rats at the end of the study. The effect of ECG and other catechins on the body weights was less than 10%. At the end of the study, the organ weights of rats in the EGCG group in compared to those of normal rats were significantly decreased: (% of organ weight in normal rats): preputial gland (35%), ventral prostate (46%), dorsolateral prostate (46%), seminal vesicle (41%), coagulating gland (34%), testis (84%), and kidney (74%). The results indicated that EGCG is effective in reducing lipid or sebum producing organ such as preputial gland and male hormone-sensitive organs, such as ventral and dorsolateral prostate gland, coagulating gland and seminal vesicles. Since ECG that are structurally very similar to EGCG (ECG has one —OH group less than EGCG) are considerably less effective than EGCG, the EGCG effect on lipid production or organ weights may be dependent on a highly specific EGCG interaction with a macromolecule(s) that can be considered a specific receptor for EGCG or a protein complex which regulate enzyme activities, gene expression and organ growth. Regulation or modulation, by natural or synthetic compounds, of the interaction or the function of the EGCG-receptor (or protein) complex may be utilized to control the lipid synthesis or the growth and function of androgen-dependent organs such as prostates.

3. Effect of EGCG on Body Weight and Androgen-Dependent Growth of Prostate and Preputial Glands of Rats Male Sprague-Dawley rats, 60±5 g body weight, were used. Rats were divided into 6 groups. Each group had 5 rats. Groups 1 and 2 were normal rats while the other 4 groups had rats castrated on the first day. On the first day and every day thereafter, Groups 3 and 4 received 100 μg testosterone/day and Groups 5 and 6 received 100 μg 5α-DHT/day. In addition Groups 2, 4, and 6 received 5 mg EGCG each day. Androgens and/or EGCG were dissolved in 0.1 ml of 30% ethanol and injected intraperitoneally daily for 7 days. The control rats (Group 1) received 0.1 ml of 30% ethanol.

The results showed that EGCG reduced the prostate weight of normal rats by about 30% and the prostate weight of castrated rats injected with testosterone by about 23% during the 7-day study period. There was no reduction of the prostate weight of castrated rats injected with 5α-DHT suggesting that, at least in part, the EGCG effect on the prostate weight loss was due to inhibition of 5α-DHT formation from testosterone.

EGCG also reduced the body weight of normal and castrated rats injected with either testosterone or 5α-DHT by 8±1% during the 7 days period. Unlike the prostate weight loss there was no androgen specificity for the EGCG effect on body weight loss. EGCG appeared to affect the weight loss by a mechanism that reduced fat accumulation. A thorough examination of various organs and blood by a veterinary pathologist did not reveal any abnormal growth or pathogenic effects of EGCG.

4. Selective Reduction of Fresh Organ Weights and Body Weight by EGCG

Figure 37:
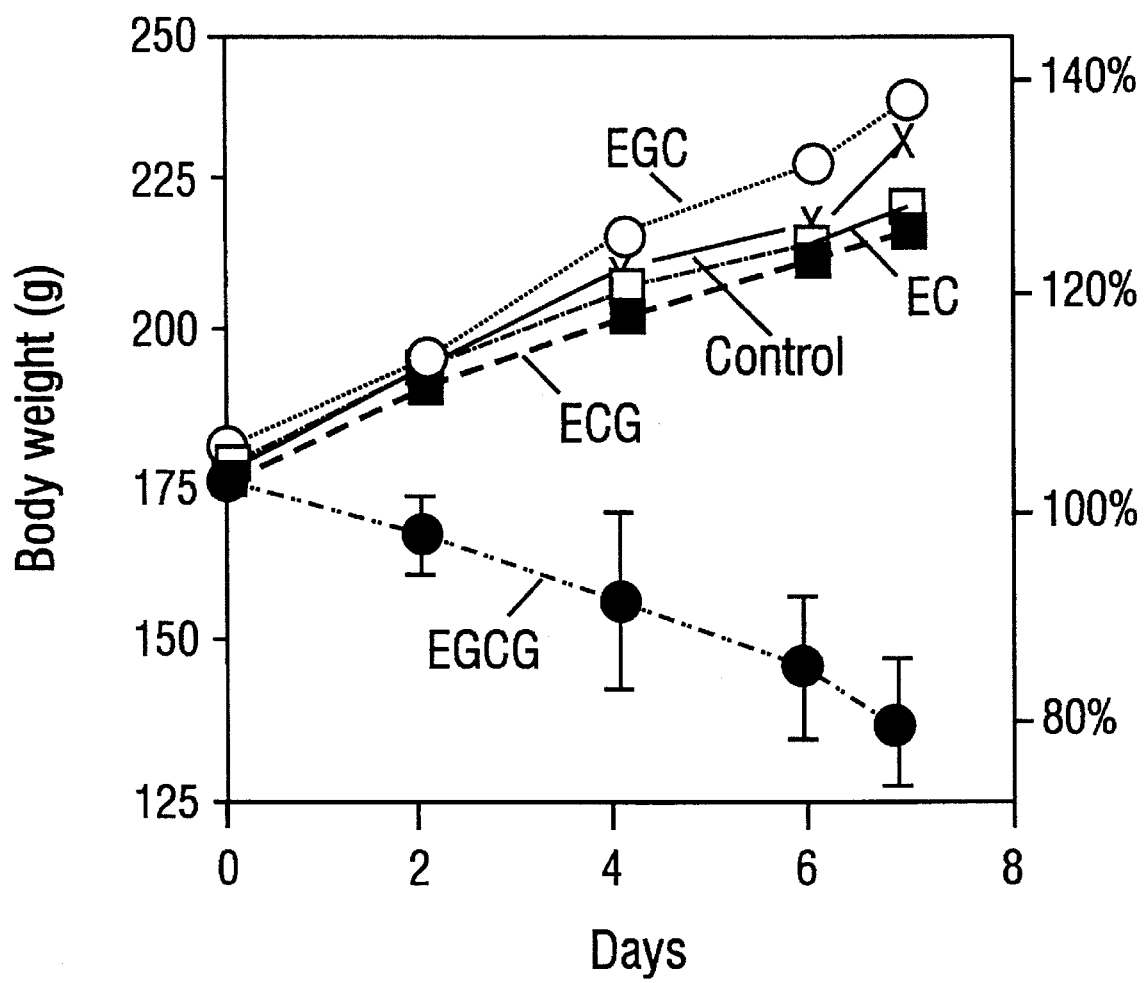
FIG. 37. Effects of EC, ECG, EGC and EGCG on body weight gain in rats.

Sprague-Dawley male rats, body weight 175 g±5 g and 5 rats per group, were injected with 0.3 ml of 30% ethanol containing 10 mg or 15 mg of one of the following catechins obtained from green tea: EC, ECG, EGC, EGCG. The control rats were injected with 0.3 ml of 30% ethanol. With EGCG, the body weight reduction was about 10% at the dose of 10 mg per day and about 25% at 15 mg per day. No significant effect on the body weight was seen with ECG and EGC at up to 15 mg per day (FIG. 37).

Figure 35:
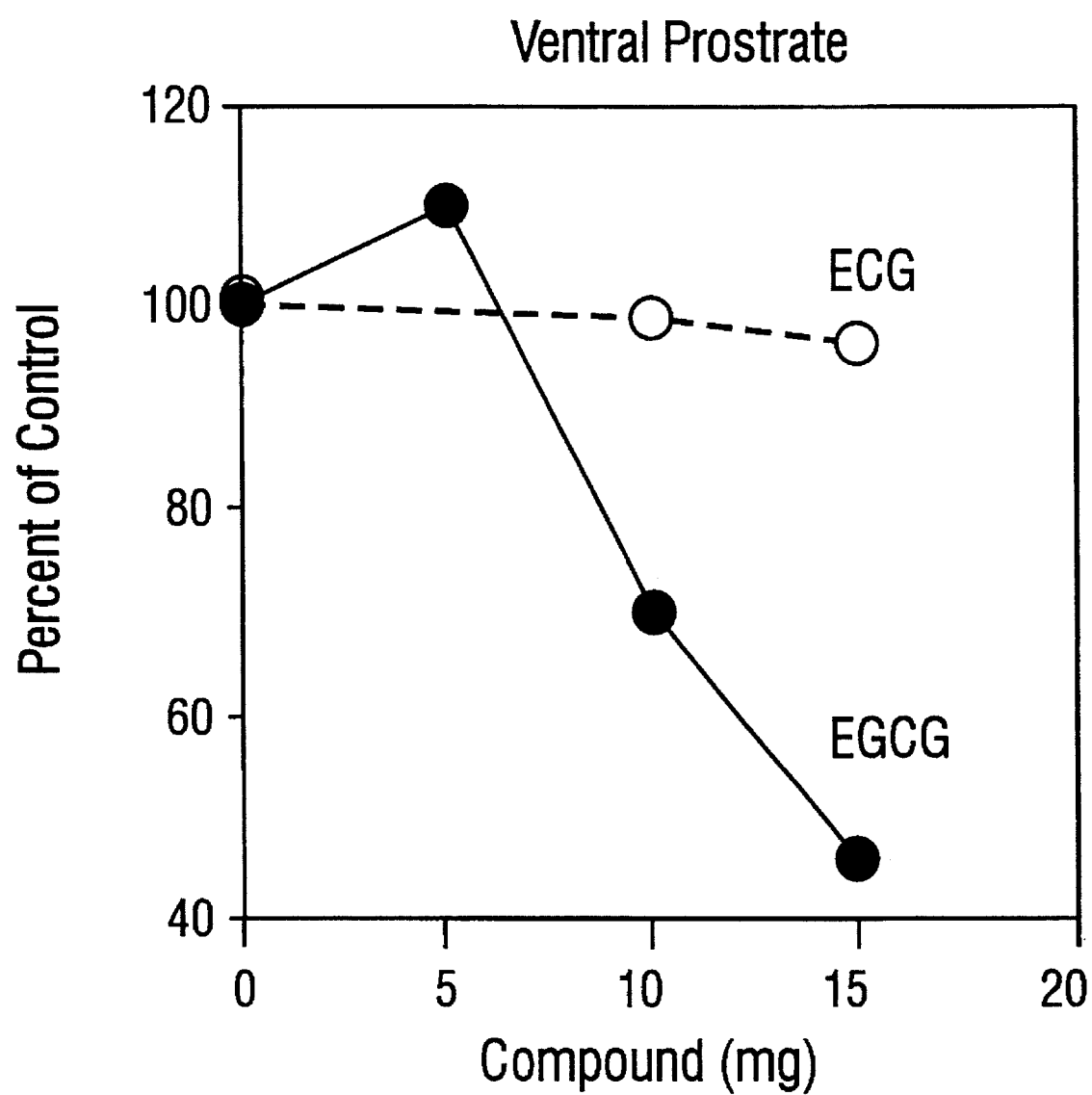
FIG. 35. Effects of ECG and EGCG on hamster ventral prostate size.
Figure 36:
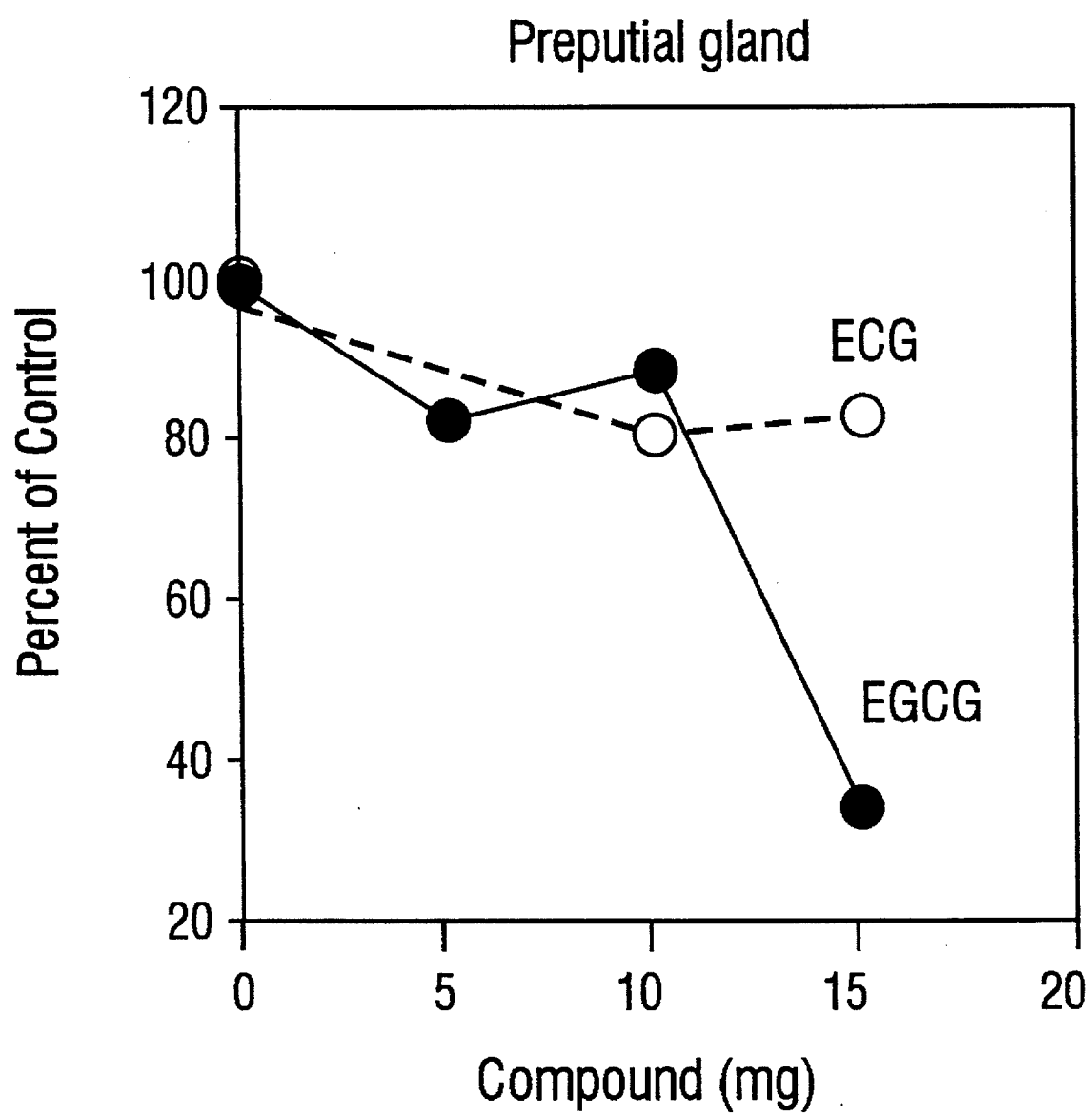
FIG. 36. Effects of ECG and EGCG on hamster preputial gland size.

EGCG, at 10 mg per day, resulted in about 30% reduction in the weight of ventral prostate (FIG. 35), dorsolateral prostate, and coagulating glands. The weight loss for seminal vesicles and preputial glands was about 20 to 25% (FIG. 36). At 15 mg per day, EGCG reduced the weight for all of these organs by 60% or more. The EGCG effect on the weights of testis and kidney was not significant with EGCG at 10 mg per day and was about 10% or less at 15 mg per day. ECG effect, if any, at 10 and 15 mg per day was less than 20% for all organs examined.

The fact that, at 10 mg per day dose of EGCG, the body weight loss was less than 10% while the prostate weight loss was more than 30% indicated that the prostate weight loss may not be the direct consequence of the body weight loss. However, for both the body weight and the organ weight loss, the structural preference for one —OH group in EGCG that is not in the ECG molecule is very important. The loss in the body weight and the organ weights may be due to EGCG interference of a common step that is required for the body and organ weight gain.

Since it appeared that the loss in the body fat weight may be responsible for the whole body weight loss, EGCG may interact and interfere with a receptor macromolecule (probably containing a protein) that can modulate specific lipid synthesis or accumulation. Lipids can modulate gene expression, cell development and differentiation, and organ growth. Specific interference of the role of lipids in the cells and organs may control the growth of organs, such as, prostate, sebaceous organs, preputial organs, and other secretory organs. Benign or abnormal growth or cancer of these organs can therefore, be chemoprevented or treated by EGCG and related compounds.

Theses studies demonstrate that the body weight was reduced significantly only by EGCG. Moreover, ECG (containing 7 OH groups) that contains one less OH group than EGCG (containing 8 OH groups) was not very active or not active at all.

Figure 38:
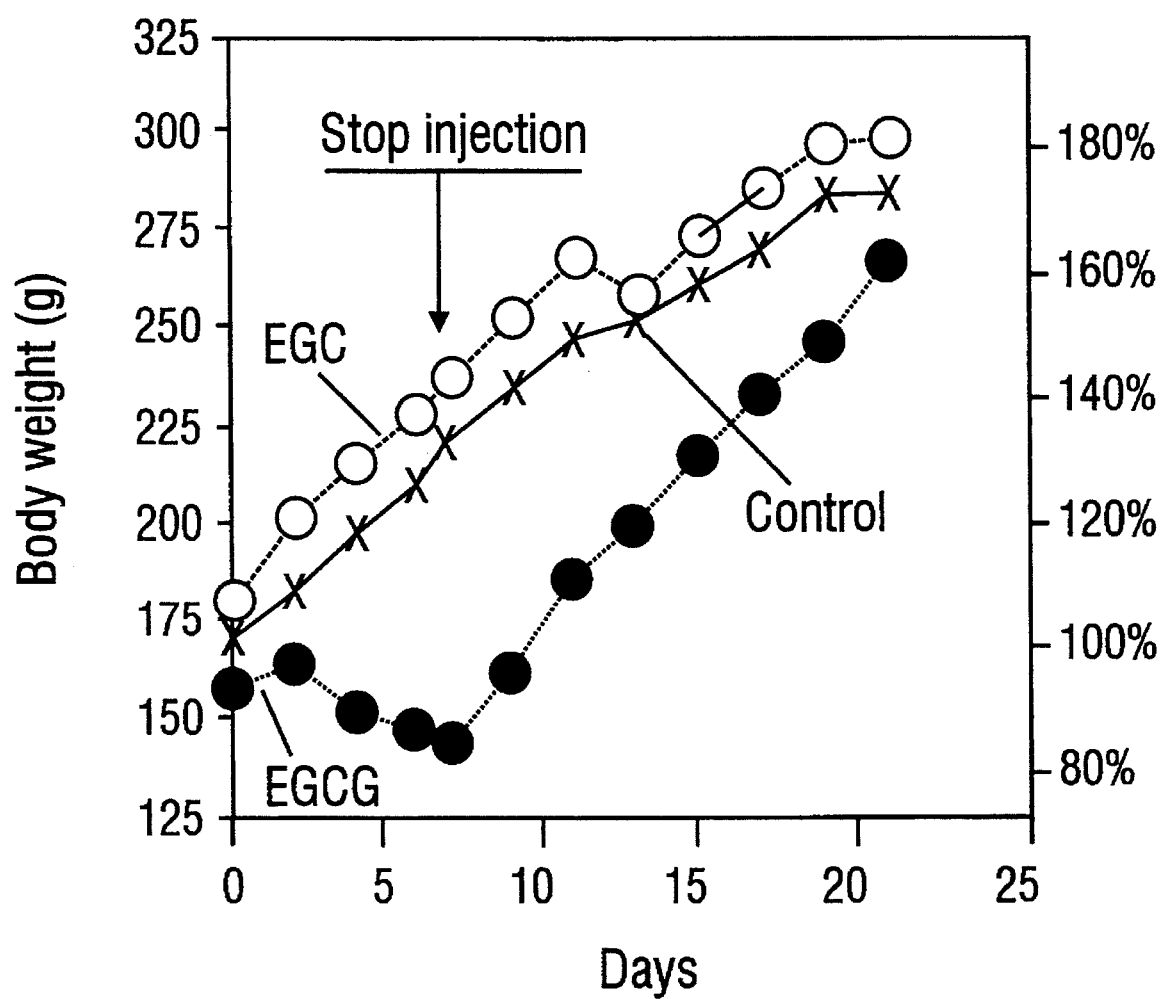
FIG. 38. Restoration of normal body weight gain following cessation of EGC and EGCG treatment in rats.

When the EGCG application was stopped, the body weight recovered to about the same weight as for the control animal, indicating that he effect of EGCG was reversible. The results demonstrated that EGCG does not cause a permanent toxicity or damage to the rats (FIG. 38).

Similar effects of EGCG was found with the organ weight for preputial organ, ventral prostate, dorsolateral prostate, coagulating gland, and seminal vesicles. EGCG effect on kidney and testis was not as significant as these androgen-sensitive organs. The EGCG effect could be observed clearly at 10 mg/rat but ECG was much less active at 10 mg/rat. Androgen sensitive male accessory organs (ventral and dorsolateral prostates, seminal vesicles, and other organs were affected to a greater extent than testis of kidney.

EXAMPLE 11

Prostate and Breast Cancer Growth in Nude Mice

Human prostate cancer PC-3 cells were grown in culture medium. About one million cells were injected into male nude mice and the growth of tumors were followed. Within two weeks, the tumor grew to about 100 $mm^3$. Three tumor bearing mice were injected with 1 mg EGCG in 0.1 ml water each day. The 3 controls received water only.

Figure 33:
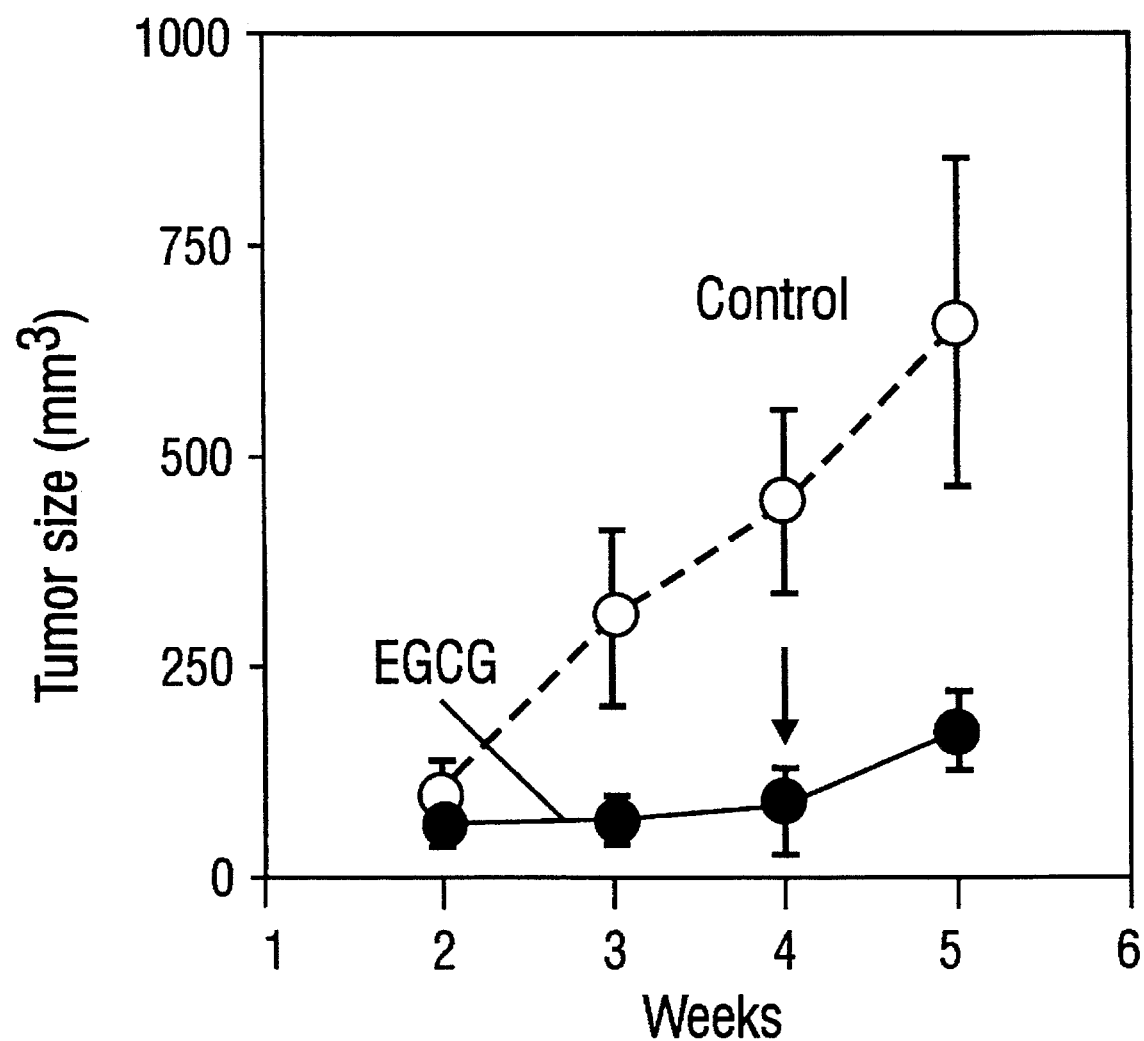
FIG. 33. Tumor size suppression by EGCG in nude mice.

Tumors in the EGCG injected mice did not grow during the following two weeks and the size of tumors were smaller than 100 $mm^3$ (FIG. 33). Tumors in the control mice (not injected with EGCG grew to about 450 $mm^3$ in two weeks and to about 650 $mm^3$ in three weeks. When EGCG injection was stopped two weeks later (arrow) tumors in the EGCG injected mice showed new growth.

Figure 34:
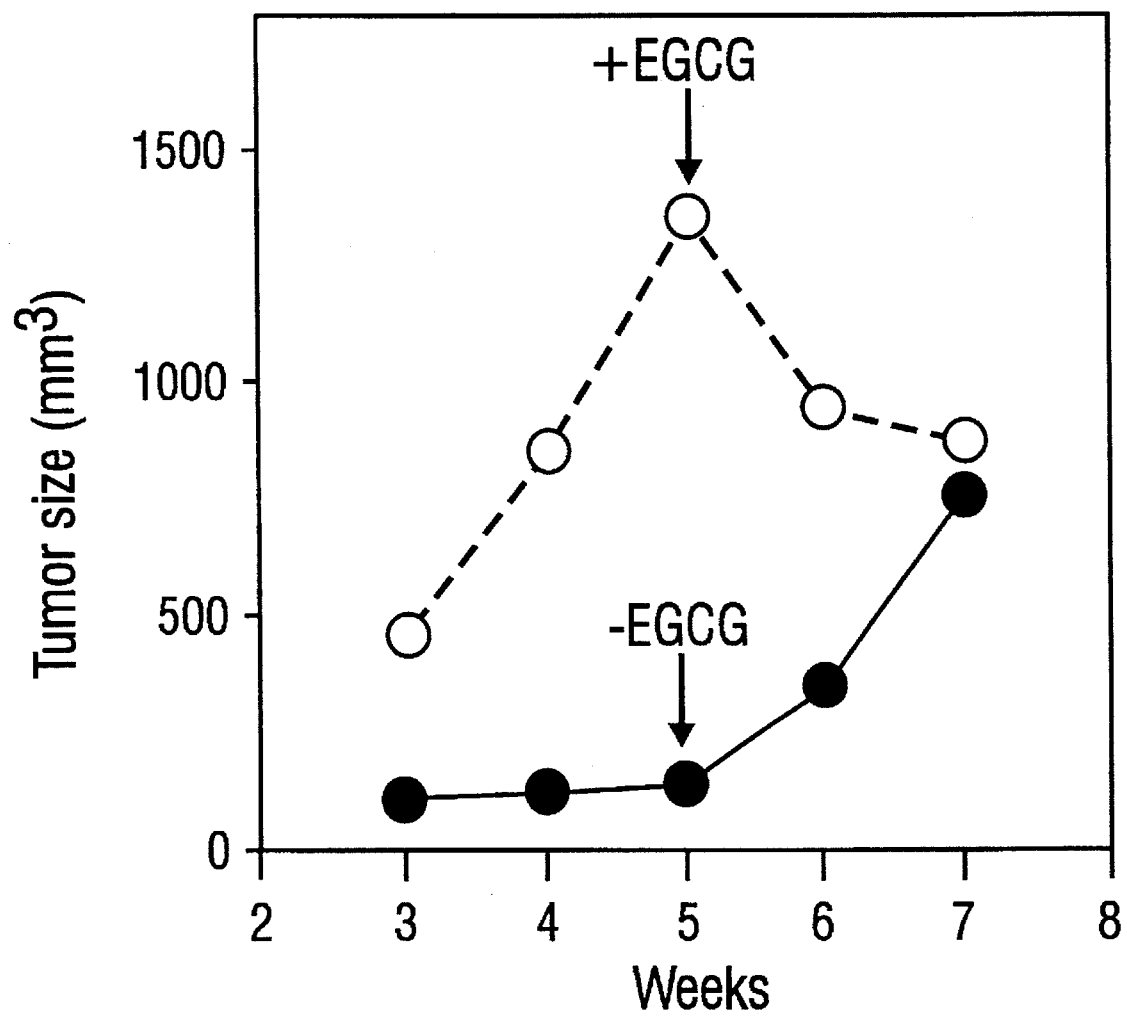
FIG. 34. Reduction of tumor size in nude mice following EGCG therapy.

This was also observed in another study (FIG. 34). The tumor in the control (not injected with EGCG) mouse grew to about 1400 $mm^3$ within 2 weeks. EGCG was then administered at this time. The tumor size reduced during the next 2 weeks to about 850 $mm^3$ and was about 500 $mm^3$ within another 2 weeks.

The tumor in the EGCG injected mouse was about 100 $mm^3$ during the 2 week injection. When EGCG injection was stopped, the tumor size started to grow to about 800 $mm^3$ within 2 weeks and was over 1200 $mm^3$ within 3 weeks. The results showed that EGCG was effective in chemoprevention and chemotherapy of the human prostate cancer. For breast tumor studies, human breast tumor cell line, MDF-7 (1 million cells) was injected into female nude mice. After 5 weeks, the tumor was over 1000 $mm^3$. EGCG (1 mg/mouse/day) injection for 2 weeks reduced the tumor by 50%).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below and all references cited herein are incorporated herein by reference to the extent that they supplement, explain, provide a background for, or teach methodology, techniques, and/or compositions employed herein.

American Cancer Society, Cancer Facts and Figures, 1994.
Anderson and Liao, "Selective retention of dihydrotestosterone by prostatic nuclei," *Nature*, 219:277–279, 1968.
Anderson and Russell, *Proc. Natl. Acad. Sci. U.S.A.*, 87:3640–3644, 1990.
Anderson et al., "Deletion of steroid 5α-reductase 2 gene in male pseudohermaphroditism," *Nature*, 354:159–161, 1991.
Anderson et at., *J. Biol. Chem.*, 264:16249–16255, 1989.
Baba et al., *J. Neurochem.*, 42:192, 1984.
Beato, *Cell*, 56:335, 1989.
Begin, *Proc. Nutrition Soc.*, 49:261, 1990.
Berman and Russell, "Cell-type-specific expression of rat steroid 5α-reductase isozymes," *Proc. Natl. Acad. Sci. U.S.A.*, 90:9359–9363, 1993.
Berry et al., "The development of human benign prostatic hyperplasia with age," *J. Urol.*, 132:474–479, 1984.
Bingham and Shaw, *J. Endocr.*, 57:111, 1973.
Blohm et al., *Biochem. Biophy. Res. Commun.*, 95:273, 1989.
Blohm et al., *Endocrinology*, 119:959, 1986.
Brandt et al., *J. Steroid Biochem. Mol. Biol.*, 37:575, 1990.
Brooks et at., *Endocrinology*, 109:830, 1981.
Brooks et al., *Proc. Soc. Exp. Biol. Med.*, 169:67, 1982.
Brooks et al., *The Prostate*, 3:35, 1982.
Brown and Scott, In: *DNA Cloning, A Practical Approach*, Glover, D. M. ed., IRL Press, Oxford, Vol. 3, 1987.
Bruchovsky and Wilson, "The conversion of testosterone to 5α-androstan-17β-ol-3-one by rat prostate in vivo and in vitro," *J. Biol. Chem.*, 243:5953–5960, 1968.
Carter and Coffey, *The Prostate*, 16:39–48, 1990.

Chakrabarty et al., "Mechanism of action of 17α-propyltestosterone in inhibiting hamster flank organ development," 74:5–8, 1980.
Chang and Liao, *J. Steroid Biochem.*, 27:123, 1987.
Cooke and Robaire, *J. Biol. Chem.*, 260:7489, 1985.
Dell and Severson, *Biochem. J.*, 258:171, 1989.
Diani et at., "Hair growth effects of oral administration of finasteride, asteroid 5α-reductase inhibitor, alone and in combination with topical minoxidil in the balding stamptail macaque," *J. Clin. Endocrinol. Metab.*, 74:345–350, 1992.
Downing et al., *J. Am. Acad. Dermatology*, 14:221, 1986.
Ehrmann and Rosenfield, *J. Clin. Endocrinol. Metab.*, 71:1, 1990.
Evans, *Science*, 240:889, 1989.
Faller et al., *Biochemistry*, 32:5705–5710, 1993.
Fang and Liao, *Mol. Pharmacol.*, 5:428, 1969.
Frost and Gomez, *Adv. Biol. Skin.*, 12:403, 1972.
Frost et al., "Biodynamic studies of hamster flank organ growth: hormonal influences," *J. Invest. Dermatol*, 61:159–167, 1973.
Gent and Ho, *Biochemistry*, 17:3023, 1978.
Gent et al., *Biophys. J.*, 33:211, 1981.
George et al., *Endocrinology*, 119:959, 1989.
Gershan and Parmegiani, *J. Med. Chem.*, 10:186, 1967.
Giovannucci, *Cancer*, 75:1766–1777, 1995.
Gittes, *New England J. Medicine*, 324:236, 1991.
Gomez and Hsia, "In vitro metabolism of testosterone-4-$^{14}$C and Δ-4-androstene-3,17-dione-4-$^{14}$C in human skin," *Biochem.*, 7:24–32, 1968.
Gormley et al., *J. Clin. Endocrinol. Metab.*, 70:1136, 1990.
Gorski, et al., *Ann. Rev. Physiol.*, 42:17, 1976.
Halgunset et al., *J. Steroid Biochem.*, 28:731, 1983.
Hall, *New Phytol.*, 71:855, 1972.
Hamilton, "Male hormone stimulation is prerequisite and incitant in common baldness," *Am. J. Anat.*, 71:451–481, 1942.
Hamilton and Montagna, "The sebaceous glands of the hamster. I. Morphological effects of androgens on integumentary structure," *Am. J. Anat.*, 86:191–233, 1950.
Hammerstein et al., *J. Steroid Biochem.*, 19:591, 1983.
Harris et al., "Identification and selective inhibition of an isozyme of steroid 5α-reductase in human scalp," *Proc. Natl. Acad. Sci. U.S.A.*, 89:10787–10791, 1992.
Herold and Kinsella, *Am. J. Clin. Nutr.*, 43:566, 1986.
Hilpakka and Liao, In:Endocrinology, 3rd ed., (DeGroot, L. I., ed.) W.B. Saunders Co., Philadelphia, 2336–2351, 1995.
Hirsch et al., *Proc. Natl. Acad. U.S.A.*, 90:5277–5281, 1994.
Honda et al., In: *Food Phytochemicals for Cancer Prevention II*, ACS Symp. Ser. 547:84–89, American Chemical Society, Washington, D.C., 1994.
Horrobin, "Nutritional and medical importance of gamma-linolenic acid," *Prog. Lipid Res.*, 31:163–194, 1992.
Horszewicz et al., *Cancer Res.*, 43:1809, 1983.
Huggins and Hodges, *Cancer Res.*, 1:293, 1940.
Ichihara and Tanaka, *Biochem. Biophys. Res. Comm.*, 149:482, 1981.
Imperato-McGinley et al., *J. Clin. Endocrinol. Metab.*, 70:777, 1990.
Imperato-McGinley, *Trend Genet*, 2:130, 1986.
Isaacs, *J. Clin. Endocrinol. Metab.*, 56:139, 1983.
Jensen et al., *Proc. Nat'l Acad. Sci. (U.S.A.)*, 59:632, 1968.
Kaighn et al., *Invest. Urol.*, 17:16, 1979.
Karmali et al., *J. Natl. Cancer Inst.*, 73:457, 1984.
Kato, *J. Steroid Biochem.*, 34:219, 1989.
Khan et al., *Febs Letter*, 292:98, 1991.
Kirschmeier et al., *DNA*, 7:219–225, 1988. 1987.
Kwok et al., *J. Am. Chem. Soc.*, 109:3684, 1987.
Lands, *Ann. Rev. Biochem.*, 34:313, 1965.
Liang and Heiss, *J. Biol. Chem.*, 256:7998, 1981.
Liang and Liao, "Inhibition of steroid 5α-reductase by specific aliphatic unsaturated fatty acids," *Biochem. J.*, 285:557–562, 1992.
Liang et al., *Endocrinology*, 115:2311, 1984.
Liang et al., *J. Biol. Chem.*, 260:4890, 1985.
Liang et al., *J. Steroid Chem.*, 19:385, 1983.
Liang et al., "Species differences in prostatic steroid 5α-reductases of rat, dog and human," *Endocrinol.*, 117:571–579, 1985.
Liang et al., *Endocrinology* (Baltimore), 112:1460–1468, 1983.
Liang et al., *J. Biol. Chem.*, 260:4890, 1985.
Liao and Fang, *Vitamins and Hormones*, 27:17, 1969.
Liao et al., *Endocrinology*, 94:1205, 1974.
Liao et al., "Androgen receptors: structures, mutations, antibodies, and cellular dynamics," *J. Steriod Biochem.*, 34:41–51, 1989.
Liao et al., "Steroid structure and androgenic activity: specificity involved in the receptor binding and nuclear retention of various androgens," *J. Biol. Chem.*, 248:6154–6162, 1973.
Liao et at., *Steroid Biochemistry*, 34:41–51, 1989.
Liao, *Int. Rev. Cytology*, 41:87, 1975.
Luderschmidt et al., "Influence of photoperiodism in testicular function and sebaceous glands in Syrian hamster," *J. Invest. Dermatol.*, 83:157–160, 1984.
McConnel et al., *J. Clin. Endocrinol. Metab.*, 74:505–508, 1992.
Mock et al., *J. Pediatrics*, 106:762, 1985.
Moguilewsky and Bouton, *J. Steroid Biochem.*, 31:699, 1988.
Mooradian et al., *Endocrine Rev.*, 8:1, 1987.
Moore and Pizza, *Biochem. J.*, 288:717, 1992.
Morello et al., *Invest. Dem.*, 66:319, 1976.
Munnich et at., *Lancet*, 2:1080, 1980.
Nakane et al., In: *Food Phytochemicals for Cancer Prevention II*, ACS Symp. Ser. 547:56–64, American Chemical Society, Washington, D.C., 1994.
Nalboone et al., *Lipids*, 25:301, 1990.
Needleman et al., *Ann. Rev. Biochem.* 55:69, 1986.
Normington and Russell, "Tissue distribution and kinetic characteristics of rat steroid 5α-reductase isozymes: evidence for distinct physiological functions," *J. Biol. Chem.*, 267:19548–19554, 1992.
O'Malley, *Mol. Endocrinol.*, 4:363, 1990.
Pattison and Buchanan, *Biochem. J.*, 92:100, 1964.
Pear et at., *Proc. Natl. Acad. Sci. U.S.A.*, 90:8392–8396, 1988.
Phillipson et al., *Eng. J. Med.*, 312:1210, 1985.
Pincus, "Anatomy and histology of skin. In: Dermatopathology," J. H. Graham, W. C. Johnson and E. B. Hewig, editors, Harper and Row, Hagerstown, 1–24, 1987.
Pochi and Strauss, "Endocrinologic control of the development and activity of the human sebaceous gland," *J. Invest. Dermatol.*, 62:191–201, 1974.
Pochi, *Ann. Rev. Med.*, 41:187, 1990.
Rasmusson et al., *J. Med. Chem.*, 29:2298, 1986.
Rittmaster et al., *J. Androl.*, 10:259, 1989.
Rittmaster et al., *J. Clin. Endocrinol. Metab.*, 65:188–193, 1987.
Rittmaster, *New Eng. J. Med.*, 330:120–125, 1994.
Russell and Wilson, *Annu. Rev. Biochem.*, 63:25–61, 1994.
Sambrook et al., *Molecular Cloning: A Laboratory Manual*, Cold Spring Harbor Laboratory Press, Cold Spring Harbor, 1989.

Sansone and Reisner, *J. Invest. Dermat.*, 56:366, 1971.
Schafer and Kragballe, "Abnormalities in epidermal lipid metabolism in patients with atopic dermatitis," *J. Invest. Dermatol.*, 96:10–15, 1991.
Schweikert and Wilson, *Clin. Endocrinol. Metab.*, 38:811, 1974.
Serafini and Lobo, *Fert Steril*, 43:74, 1985.
Siiteri and Wilson, *J. Clinical Invest.*, 49:1737, 1970.
Silverberg and Lubera, *Cancer Statistics*, 40:9, 1990.
Stoll et al., *J. Lipid Res.*, 32:843, 1991.
Stoner and the Finasteride Study Group, "The clinical effects of a 5α-reductase inhibitor, finasteride, on benign prostatic hyperplasia," *J. Urol.*, 147:1298–1302, 1992.
Strauss and Yesalis, *Annu. Rev. Med.*, 42:499, 1991.
Synder, *Ann. Rev. Med.*, 35:207, 1984.
Szepsesi et al., *J. Nutr.*, 119:161, 1989.
Takayasu and Adachi, "The in vivo and in vitro conversion of testosterone to 17β-hydroxy-5α-androstan-3-one (dihydrotestosterone) by sebaceous gland of hamsters," *Endocrinology*, 90:73–79, 1972.
Tesoriere et al., *J. Neurochem.*, 51:704, 1988.
Topp, *Virology*, 113:408–411, 1981.
Tosaki and Hearse, *Basic Res. Cardiol.*, 83:158, 1988.
Vallette et at., *J. Steroid Biochem.*, 263:3639, 1988.
Vermeulen et al., *The Prostate*, 14:45, 1989.
Voigt and Hsia, "The antiandrogenic action of 4-androsten-3-one-17β-carboxylic acid and its methylester on hamster flank organ," *Endocrinol.*, 92:1216–1222, 1973.
Voigt et al., *J. Biol. Chem.*, 260:4890, 1985.
Weissmann et al., "Antiandrogenic effects of topically applied spironolactone on the hamster flank organ," *Arch. Dermatol.*, 121:57–67, 1985.
Weissmann et al., "Morphometric studies of the hamster flank organ: and improved model to evaluate pharmacologic effects on sebaceous glands," *J. Invest. Dermatol.*, 82:522–525, 1984.
Wenderoth and George, *Endocrinology*, 113:569, 1983.
Williams G. M., "Clinical Significance of Esterases in Man", *Clinical Pharmacokinetics*, 10:392–403, 1985.
Wilson, *Am. J. Med.*, 68:745, 1980.
Wright, *Prostaglandins, Leukotrienes and Essential Fatty Acids*, 38:229, 1989
Wuest and Lucky, "Differential effect of testosterone on pigmented spot, sebaceous glands and hair follicles in the Syrian hamster flank organ," *Skin Pharmacol.*, 2:103–113, 1989.
Wynder et at., *Nutr. Cancer*, 22:1–10, 1994.
Yang and Wang, *J. Natl. Cancer Inst.*, 85:1038–1049, 1993.
Ziboh and Miller, *Annu. Rev. Nutr.*, 10:433, 1990.
Zuniga et al., *J. Nutr.*, 119:152, 1989.

What is claimed is:

1. A method of reducing weight in an animal comprising administering to the animal an amount of a compound in a pharmaceutically acceptable vehicle, the compound having the structure

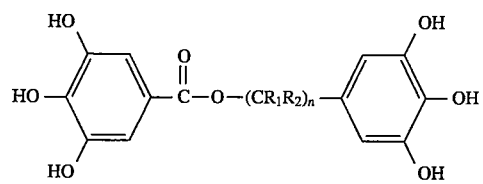

and isomers thereof where $n=1$ or 2; $R_1$ and $R_2$ are independently H, halogen, lower alkyl, OH, or $OR_3$, where $R_3$ is lower alkyl, and pharmaceutically acceptable salts thereof.

2. The method of claim 1, wherein the compound has the structure shown in FIG. 20A.

3. The method of claim 1, wherein the compound is epicatechin-3-gallate or epigallocatechin-3-gallate.

4. The method of claim 3, wherein the compound is (−)epicatechin-3-gallate or (−)epigallocatechin-3-gallate.

5. The method of claim 1, wherein administering the compound produces a decrease in weight of an androgen sensitive organ.

6. The method of claim 5, wherein the androgen sensitive organ is identified as a prostate gland, coagulating gland, seminal vesicle or a preputial gland.

7. A method of arresting or reducing prostate cancer cell growth comprising treating an animal having or susceptible to prostate tumor growth with a pharmaceutically acceptable composition that includes epigallocatechin-3-gallate.

8. The method of claim 7, wherein the epigallocatechin-3-gallate is the (−)epigallocatechin-3-gallate isomer.

* * * * *

UNITED STATES PATENT AND TRADEMARK OFFICE
CERTIFICATE OF CORRECTION

PATENT NO. : 5,605,929
APPLICATION NO. : 08/442055
DATED : February 25, 1997
INVENTOR(S) : Shutsung Liao and Tehming Liang Page 1 of 1

It is certified that error appears in the above-identified patent and that said Letters Patent is hereby corrected as shown below:

On the Title page item [75] should read
[75]    Inventors: Shutsung Liao, Chicago Ill.

Signed and Sealed this

Third Day of February, 2009

JOHN DOLL
*Acting Director of the United States Patent and Trademark Office*